United States Patent
Makings et al.

(10) Patent No.: US 8,263,605 B2
(45) Date of Patent: *Sep. 11, 2012

(54) MODULATORS OF MUSCARINIC RECEPTORS

(75) Inventors: Lewis R. Makings, Encinitas, CA (US); Miguel Garcia-Guzman Blanco, San Diego, CA (US); Dennis J. Hurley, San Marcos, CA (US); Ioana Drutu, Watertown, MA (US); Gabriel Raffai, Tucson, AZ (US); Daniele M. Bergeron, La Mesa, CA (US); Akiko Nakatani, San Diego, CA (US); Andreas P. Termin, Encinitas, CA (US); Alina Silina, San Diego, CA (US)

(73) Assignee: Vertex Pharmaceutical Incorporated, Cambridge, MA (US)

( * ) Notice: Subject to any disclaimer, the term of this patent is extended or adjusted under 35 U.S.C. 154(b) by 667 days.

This patent is subject to a terminal disclaimer.

(21) Appl. No.: 12/224,270

(22) PCT Filed: Feb. 22, 2007

(86) PCT No.: PCT/US2007/004745
§ 371 (c)(1),
(2), (4) Date: Feb. 16, 2009

(87) PCT Pub. No.: WO2007/100670
PCT Pub. Date: Sep. 7, 2007

(65) Prior Publication Data
US 2009/0227614 A1    Sep. 10, 2009

Related U.S. Application Data

(60) Provisional application No. 60/775,501, filed on Feb. 22, 2006, provisional application No. 60/775,524, filed on Feb. 22, 2006.

(51) Int. Cl.
*A61K 31/44* (2006.01)
*C07D 401/00* (2006.01)
*C07D 451/00* (2006.01)
*C07D 453/00* (2006.01)

(52) U.S. Cl. .......................... 514/278; 546/18
(58) Field of Classification Search .................. 514/278; 546/18
See application file for complete search history.

(56) References Cited

U.S. PATENT DOCUMENTS

| | | |
|---|---|---|
| 3,654,287 A | 4/1972 | Dykstra |
| 3,666,764 A | 5/1972 | Campbell et al. |
| 3,959,475 A | 5/1976 | Bauer et al. |
| 3,962,259 A | 6/1976 | Bauer et al. |
| 4,233,307 A | 11/1980 | Ono et al. |
| 4,349,549 A | 9/1982 | Roszkowski et al. |
| 4,558,049 A | 12/1985 | Bernardi et al. |
| 4,612,121 A | 9/1986 | Hermansson |
| 5,091,387 A | 2/1992 | Evans et al. |
| 5,219,860 A | 6/1993 | Chambers et al. |
| 5,324,733 A | 6/1994 | Billington et al. |
| 5,457,207 A | 10/1995 | Efange et al. |
| 5,576,321 A | 11/1996 | Krushinski, Jr. et al. |
| 5,578,593 A | 11/1996 | Chen et al. |
| 5,614,523 A | 3/1997 | Audia et al. |
| 5,627,196 A | 5/1997 | Audia et al. |
| 5,652,235 A | 7/1997 | Chen et al. |
| 5,658,921 A | 8/1997 | Perregaard et al. |
| 5,665,725 A | 9/1997 | Moltzen et al. |
| 5,741,789 A | 4/1998 | Hibschman et al. |
| 5,789,402 A | 8/1998 | Audia et al. |
| 5,817,679 A | 10/1998 | Shen et al. |
| 5,885,999 A | 3/1999 | Elliott et al. |
| 6,013,652 A | 1/2000 | Maccoss et al. |
| 6,130,217 A | 10/2000 | Arnold et al. |
| 6,166,040 A | 12/2000 | Fairhurst et al. |

(Continued)

FOREIGN PATENT DOCUMENTS

CN    1535967    10/2004

(Continued)

OTHER PUBLICATIONS

Bymaster, F., "Xanomeline: A Selectve Muscarinic Agonist for the Teament of Azheimer's Disease", Drug Development Research, 40 (1997), pp. 158-170.

Chambers, M., "Spiropiperidines as High-Affinity, Selective σ Ligands", J. Med. Chem., 35(11) (1992), pp. 2033-2039.

Chiaverelli, S., "Ricerche nella serle della 4-feniipiperidina. Nota v. Derivati della 4,4'-spiro-(1"metilpiperidin)-1,2,3,4,-tetraidroisochinolina", Gazzette Chimica Italiana, 90, 189 (1960), CN1535967.

Custers, F., "Vesamicol and Some of its Derivatives: Questionable Ligands for Selectively Labelling Acetylcholine Transporters in Rat Brain", Eur. Jour. of Pharm., 338 (1997), pp. 177-183.

(Continued)

*Primary Examiner* — Paul Zarek
(74) *Attorney, Agent, or Firm* — Honigman Miller Schwartz and Cohn LLP; Christopher C. Forbes; Jonathan P. O'Brien

(57) ABSTRACT

The present invention relates to modulators of muscarinic receptors of formula (I). The present invention also provides impositions comprising such modulators, and methods therewith for treating muscarinic receptor mediated diseases.

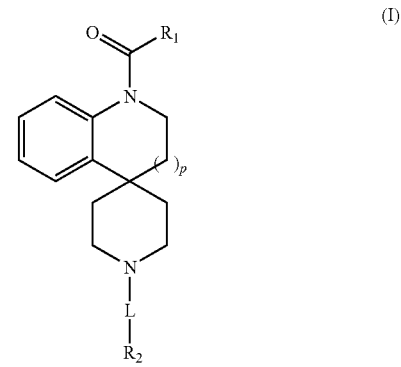

18 Claims, No Drawings

U.S. PATENT DOCUMENTS

| | | | |
|---|---|---|---|
| 6,291,672 B1 * | 9/2001 | Bichon et al. | 540/597 |
| 6,326,375 B1 | 12/2001 | Fukami et al. | |
| 6,436,962 B1 | 8/2002 | Hoffman et al. | |
| 6,566,367 B2 | 5/2003 | Bakthavatchalam et al. | |
| 6,713,487 B2 | 3/2004 | Yu et al. | |
| 6,720,324 B2 | 4/2004 | Marzabadi et al. | |
| 6,828,440 B2 | 12/2004 | Goehring et al. | |
| 6,869,960 B2 | 3/2005 | Ito et al. | |
| 6,943,199 B2 | 9/2005 | De Lombaert et al. | |
| 7,045,527 B2 | 5/2006 | Chen et al. | |
| 7,205,417 B2 | 4/2007 | Fukami et al. | |
| 2002/0188124 A1 | 12/2002 | Fukami et al. | |
| 2003/0036652 A1 | 2/2003 | Bakthavatchalam et al. | |
| 2003/0158219 A1 | 8/2003 | Ito et al. | |
| 2004/0054177 A1 | 3/2004 | Otake et al. | |
| 2004/0072847 A1 | 4/2004 | Bakthavatchalam et al. | |
| 2004/0122074 A1 | 6/2004 | Dow et al. | |
| 2004/0142956 A1 | 7/2004 | Chen et al. | |
| 2004/0204397 A1 | 10/2004 | Chaturvedula et al. | |
| 2005/0033048 A1 | 2/2005 | Bakthavatchalam et al. | |
| 2005/0153998 A1 | 7/2005 | Ito et al. | |
| 2005/0176703 A1 | 8/2005 | Gabriel et al. | |
| 2005/0215576 A1 | 9/2005 | Degnan et al. | |
| 2005/0261332 A1 | 11/2005 | Distefano et al. | |
| 2006/0040964 A1 | 2/2006 | Bakthavatchalam et al. | |
| 2006/0111380 A1 | 5/2006 | Otake et al. | |
| 2006/0173027 A1 | 8/2006 | Marzabadi et al. | |
| 2006/0183904 A1 | 8/2006 | Guo et al. | |
| 2006/0211722 A1 | 9/2006 | Jiao et al. | |
| 2006/0217372 A1 | 9/2006 | Blanco-Pillado et al. | |
| 2006/0281746 A1 * | 12/2006 | Kehler et al. | 514/235.2 |
| 2007/0043023 A1 | 2/2007 | Makings et al. | |

FOREIGN PATENT DOCUMENTS

| | | |
|---|---|---|
| DE | 3342164 | 11/1983 |
| EP | 0065864 | 12/1982 |
| EP | 0070171 | 1/1983 |
| EP | 0414289 | 2/1991 |
| EP | 0444945 | 9/1991 |
| EP | 0486280 | 5/1992 |
| EP | 0533243 | 3/1993 |
| EP | 0615977 | 9/1994 |
| GB | 1575800 | 10/1980 |
| GB | 2131021 | 11/1983 |
| GB | 2308064 | 6/1997 |
| GB | 2355264 | 9/2000 |
| GB | 2355456 | 9/2000 |
| JP | 59059685 | 4/1984 |
| JP | 2001/278886 | 10/2001 |
| JP | 2002/316987 | 10/2002 |
| WO | WO 94/19367 | 9/1994 |
| WO | WO 94/22846 | 10/1994 |
| WO | WO 95/11029 | 4/1995 |
| WO | WO 95/14025 | 5/1995 |
| WO | WO 95/28389 | 10/1995 |
| WO | WO 97/41878 | 11/1997 |
| WO | WO 97/41879 | 11/1997 |
| WO | WO 99/06434 | 2/1999 |
| WO | WO 99/32489 | 7/1999 |
| WO | WO 99/64002 | 12/1999 |
| WO | WO 00/06146 | 2/2000 |
| WO | WO 00/06153 | 2/2000 |
| WO | WO 00/06545 | 2/2000 |
| WO | WO 00/38720 | 7/2000 |
| WO | WO 01/02386 | 1/2001 |
| WO | WO 01/22919 | 4/2001 |
| WO | WO 01/29027 | 4/2001 |
| WO | WO 01/45707 | 6/2001 |
| WO | WO 01/64213 | 9/2001 |
| WO | WO 02/48152 | 6/2002 |
| WO | WO 02/094825 | 11/2002 |
| WO | WO 03/014083 | 2/2003 |
| WO | WO 03/037271 | 5/2003 |
| WO | WO 03/064425 | 8/2003 |
| WO | WO 03/095427 | 11/2003 |
| WO | WO 03/104236 | 12/2003 |
| WO | WO 03/106457 | 12/2003 |
| WO | WO 2004/010942 | 2/2004 |
| WO | WO 2004/010943 | 2/2004 |
| WO | WO 2004/011427 | 2/2004 |
| WO | WO 2004/028459 | 4/2004 |
| WO | WO 2004/050652 | 6/2004 |
| WO | WO 2004/074273 | 9/2004 |
| WO | WO 2004/089307 | 10/2004 |
| WO | WO 2005/016884 * | 2/2005 |
| WO | WO 2005/016913 | 2/2005 |
| WO | WO 2005/063254 | 7/2005 |
| WO | WO 2005/065779 | 7/2005 |
| WO | WO 2005/075484 | 8/2005 |
| WO | WO 2005/100360 | 10/2005 |
| WO | WO 2006/001958 | 1/2006 |
| WO | WO 2006/028239 | 3/2006 |
| WO | WO 2006/058303 | 6/2006 |
| WO | WO 2007/077122 | 7/2007 |

OTHER PUBLICATIONS deLaszlo, S., "A Nonpeptidic Agonist Ligand of the Human C5A Receptor: Synthesis, Binding Affinity Optimization and functional Characterization", Bioorganic and Medicinal Chem. Lett., 7(2) (1997), pp. 213-218.

Dhar, T.G., "Design and Synthesis of Novel α1a Adrenoceptor-Selective Antagonists. 2. Approaches to Eliminate Opioid Agonist Metabolites via Modification of Linker and 4-Methoxycarbonyl-4-phenylpiperidine Moiety1.2", J. Med. Chem, 42 (1999), pp. 4778-4793.

Efange, S., "(+)-p-([18F]Fluorobenzyl)Spirotrozamicol {(+)-[18F]Spiro-FBT}: Synthesis and Biological Evaluation of a High-Affinity Ligand for the Vesicular Acetylcholine Transporter (VAChT)", Nuclear Medicine and Biology, vol. 26 (1999), pp. 189-192.

Efange, S., "Comparative Tissue Distribution of conformationally Restricted Radioiodinated Vesamicol Receptor Ligands", Nuclear Medicine and Biology, 22(4) (1995), pp. 437-444.

Efange, S., "Molecular Determinants of Selectivity at the Vesamicol Receptor", Biochem. Phar., 49(6) (1995), pp. 791-797.

Efange, S., "N-Hydoxyalkyl Derivatives of 3β-Phenyltopane and Methylspio[1H-indoline-3,4'-piperidine]: Vesamicol Analogues with Affinity or Monoamine Transporters", J. Med. Chem, 40 (1997), pp. 3905-3914.

Efange, S., "Spirovesamicols: Conformationally Restricted Analogs of 2-(4-Phenylpiperidino)cyclohexanol (Vesamicol, AH5183) as Potential Modulators of Presynaptic Cholinergic Function", J. Med. Chem, 37 (1994), pp. 2574-2582.

Evans, B., "Orally Active, Nonpeptide Oxytocin Antagonists", J. Med. Chem., 35(21) (1992), pp. 3919-3927.

Freireich, et al., "Quantitative Comparison of Toxicity of Anticancer Agents in Mouse, Rat, Hamster, Dog, Monkey and Man," Cancer Chemother. Rep., 50: 219 (1966).

Kim, D., Dooseop, et al., "Discovery of Human CCR5 Antagonists Containing Hydantoins for the Treatment of HIV-1 Infection", Bioorganic and Medicinal Chem. Lett., 11 (2001, pp. 3099-3102.

Malmstrom, R., "Pharmacology of H 394/84, a dihydropyridine neuropeptide Y Y1 Receptor Antagonist, in Vivo", Eur. Jour. of Pharm., 418 (2001), pp. 95-104.

Matier, W., "Novel Cyclizations and Ring-Opening Reactions of 3-Phenylindene Derivatives", J. Org. Chem., vol. 36, No. 5 (1971), pp. 650-654.

Moltzen, E., "σ Ligands with Subnanomolar Affinity and Preference for the σ2 Binding Site. 2. Spiro-Joined Benzofuran, Isobenzofuran and Benzopyran Piperidines", J. Med. Chem., 38 (1995), pp. 2009-2017.

Morrow, D., "Synthesis of Some New 17-Spiro-Substituted Steroids", J. Med. Chem., 10(2) (1967), pp. 133-138.

Nargund, R., "Peptidomimetic Growth Hormone Secretagogues: Synthesis and Biological Activities of Analogs Varied at the Indole Nucleus of the Prototypical Spiropiperidine L-162,752", Bioorganic and Medicinal Chem. Lett., vol. 6, No, 14 (1996), pp. 1731-1736.

Nargund, R., "Synthesis and Biological of Camphor-Based Non-Peptide Growth Hormone Secretagogues", Bioorganic and Medicinal Chem. Let., vol. 6, No. 11 (1996), pp. 1265-1270.

Oprea, T., "Is There a Difference between Leads and Drugs? A Historical Perspective", J. Chem. Inf. Comput. Sci., 41 (2001), pp. 1308-1315.

Pasternak, A., "Potent, Orally Bioavailable Somatostatin Agonists: Good Absorption Achieved by Urea Backbone Cyclization", Bioorganic and Medicinal Chem. Lett., 9 (1999), pp. 491-496.

Patchett, A.A., "The Synthesis of 17β-Amino-17 α-(2'-cerboxyethyl)androstane Lacatama1", J. Org. Chem, 27 (1962), pp. 3822-3828.

Pettibone, D.J., "Identification of an Orally Active, Nonpeptidyl Oxytocin Antagonist", Journal of Pharm. and Experimental Therap., 264(1) (1993), pp. 308-314.

Takemoto, T., "Asymmetric Synthesis of Enantiomerically Pure Spiro[((2S)-hydroxy)indane-1,4'-piperidine]", Tetrahedron Asymmetry, 10 (1999), pp. 1787-1793.

Tata, J., "The Synthesis and Activity of Spiroindane Growth Hormone Secretagogues", Bioorganic and Medicinal Chem. Lett, 7(6) (1997), pp. 663-668.

Williams, P., "1-(((7,7-Dimethyl-2(S)-(2(S)-amino-4-(methylsulfonyl)butyramido)bicyclo[2.2.1]-heptan-1(S)-yl)methyl)sulfonyl)-4-2(2-methylphenyl)piperazine (L-368,899): An Orally Bioavailable, Non-Peptide Oxytocin Antagonist with Potential Utility for Managing Preterm Labor", J. Med. Chem, 37 (1994), pp. 555-571.

Yang, L., "Potent 3-Spiropiperidine Growth Hormone Secretagogues", Bioorganic and Medicinal Chem. Lett, 8(1) (1998), pp. 107-112.

Yang, L., "The Design and Synthesis of Non-Peptide Somatostatin Receptor Agonists", Proceedings of the American Peptide Symposium, 16th Minneapolis, MN, Jun. 26-Jul. 1, 1999, (2000), meeting date 1999, 250-252.

Abdel-Magid, A.F., "Reductive Amimation of Aldehydes & Ketones with Sodium Triacetoxyborohydride. Studies on Direct & Indirect . . . ", J. Org. Chem., 61 (1996),n pp. 3849-3862.

Caulfield, M.P., "International Union of Pharmacology. XVII. Classification of Muscarinic Acetylcholine Receptors", Pharmacol. Rev., 50 (1998), pp. 279-290.

Caulfield, M.P., "Muscarinic Receptors—Characterization, Coupling, and Function", Pharmacol. Ther., 58 (1993), pp. 319-379.

Cheng, Y., "Spirosubstituted Azacyclics as Neurokinin Antagonists", Tet. Lett, 38 (1997), pp. 1497-1500.

Delapp, N., "Therapeutic Opportunities for Muscarinic Receptors in the Central Nervous System", J. Med. Chem., 43(23) (200), pp. 4333-4353.

Hulme, E.C., "Muscarinic Receptor Subtypes", Ann. Rev. Pharmacol. Toxicol., 30 (1990), pp. 633-673.

Maligres, P.E., "Spiroindolinepiperidine Derivatives",Tetrahedron, 53 (1997), pp. 10983-10992.

Bignan, G. "Preparation of 3-Spiocyclic Indolin-2-ones as Ligands for the ORL-1 Receptor", Bioorganic and Medicinal Chem. Left, 15 (2005), pp. 5022-5026.

Butera, J., "Recent Approaches to the Treatment of Urinary Incontinence: A Survey of Patent Activity from 1995 to 1998", Expert Opinion on Therapeutic Patents, 8(8) (1998), pp. 1017-1035.

Reimann, E., "Synthese und pharmakologische Prüfung Homologer und hydroxylierter 3,4-Dihydro-1'-methylspiro [naphthalin-(2H),4'-piperidine]", Archiv. Der. Pharmazie, VCH Verlagsgesellschaft MBH, Weinheim, DE, 323 (1990), pp. 35-39.

Rubin, B., "Novel Medications for Asthma: a Look at the Future", Exper. Opinion on Investigational Drugs, 16(6) (2007), pp. 889-897.

\* cited by examiner

MODULATORS OF MUSCARINIC RECEPTORS

CROSS REFERENCE TO RELATED APPLICATIONS

This application is the U.S. National Phase application of PCT Application Serial No. PCT/US2007/004745, filed Feb. 22, 2007, which claims the priority of U.S. Application Ser. No. 60/775,501, filed Feb. 22, 2006, and U.S. Application Ser. No. 60/775,524, filed Feb. 22, 2006. All of these documents are incorporated herein in their entirety.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," J. Med. Chem., 43(23), pp. 4333-4353 (2000); Hulme, E. C. et al., "Muscarinic Receptor Subtypes," Ann. Rev. Pharmacol. Toxicol., 30, pp. 633-673 (1990); Caulfield, M. P. et al., "Muscarinic Receptors-Characterization, Coupling, and Function," Pharmacol. Ther., 58, pp. 319-379 (1993); Caulfield, M. P. et al., International Union of Pharmacology. XVII. "Classification of Muscarinic Acetylcholine Receptors," Pharmacol. Rev., 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors). Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides methods of modulating the activity of a muscarinic receptor (e.g., $M_1$, $M_2$, $M_3$, $M_4$, $M_5$, or combinations thereof) using compounds of formula I:

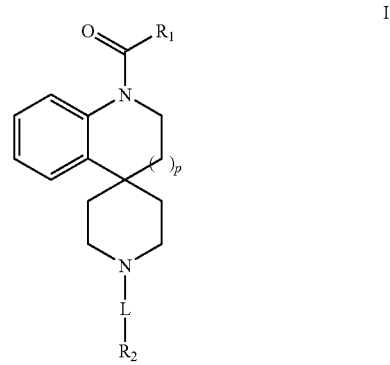

or a pharmaceutically acceptable salt thereof, wherein $R_1$, $R_2$, L, and p are described below.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradycardia, gastric acid secretion, asthma, GI disturbances and wound healing.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or aliphaticsulfonylamino], sulfonyl [e.g., alkyl-$SO_2$—, cycloaliphatic-$SO_2$—, or aryl-$SO_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-$SO_2$—, aliphaticamino-$SO_2$—, or cycloaliphatic-$SO_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as —N($R^X$)—C(O)—$R^Y$ or —C(O)—N($R^X$)$_2$, when used terminally, and —C(O)—N($R^X$)— or —N($R^X$)—C(O)—when used internally, wherein $R^X$ and $R^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —$NR^XR^Y$ wherein each of $R^X$ and $R^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl.

A "cycloalkenyl" group, as used herein, refers to a non-aromatic carbocyclic ring of –10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form a heteroaryl such as tetrahydroisoquinoline.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b] thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1, 2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic) oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl) amino)heteroaryl]; (cyanoalkyl)heteroaryl; (alkoxy)heteroaryl; (sulfamoyl)heteroaryl [e.g., (aminosulfonyl) heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; (((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroalkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—C(O)—NR$^X$R$^Y$ or —NR$^X$—C(O)—O—R$^Z$ wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —C(O)OH, —C(O)OR$^X$, —OC(O)H, —OC(O)R$^X$ when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)—when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to —O.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—C(O)—NR$^Y$R$^Z$ and a "thiourea" group refers to the structure —NR$^X$—C(S)—NR$^Y$R$^Z$ when used terminally and —NR$^X$—C(O)—NR$^Y$— or —NR$^X$—C(S)—NR$^Y$— when used internally, wherein R$^X$, R$^Y$, and R$^Z$ have been defined above.

As used herein, a "guanidine" group refers to the structure —N—C(N(R$^X$R$^Y$))N(R$^X$R$^Y$) wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=(NR$^X$)N(R$^X$R$^Y$) wherein R$^X$ and R$^Y$ have been defined above.

As used herein, "cyclic group" or "cyclic moiety" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03.7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, L and other variables contained herein encompass specific groups, such as alkyl and aryl. Unless otherwise noted, each of the specific groups for the variables $R_1$, $R_2$, $R_3$, and $R_4$, and other variables contained therein can be optionally substituted with one or more substituents described herein. Each substituent of a specific group is further optionally substituted with one to three of halo, cyano, oxo, alkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

II. Compounds

A. Generic Compounds

The present invention provides compounds of formula I and methods of modulating muscarinic receptor activity using compounds of formula I.

One aspect of the present invention provides compounds of formula I:

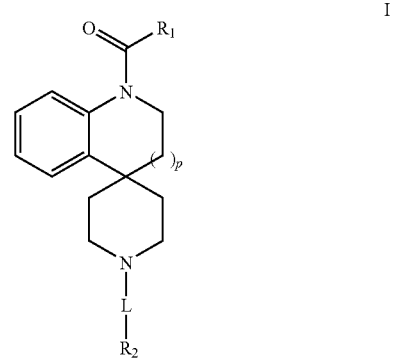

or a pharmaceutically acceptable salt thereof, wherein $R_1$ is an optionally substituted aliphatic or —$NR_6R'_6$. Each of $R_6$ and $R'_6$ is independently hydrogen or an optionally substituted $C_{1-4}$ aliphatic. Alternatively, $R_6$ and $R'_6$ together with the nitrogen atom to which they are attached form an optionally substituted 4-7 membered heterocycloaliphatic.

L is —$(CH_2)_n$—, wherein n is 0-2.

$R_2$ is a cycloaliphatic or a heterocycloaliphatic, each of which is optionally substituted with 1-3 of $R_3$. Each $R_3$ is -$Z^A R_4$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^A$—, $CONR^A NR^A$—, —$CO_2$—, —OCO—, —$NR^A CO_2$—, —O—, —$NR^A CONR^A$—, —$OCONR^A$—, —$NR^A NR^A$—, —$NR^A CO$—, —S—, —SO—, —$SO_2$—, —$NR^A$—, —$SO_2 NR^A$—, —$NR^A SO_2$—, or —$NR^A SO_2 NR^A$—. Each $R_3$ is independently $R^A$, halo, —OH, —$NH_2$, —$NO_2$, —CN, or —$OCF_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

Each p is 0 or 1.

When p is 0, then $R_1$ is a $C_{2-8}$ alkyl, an alkenyl, an alkynyl, N,N-dimethylaminocarbonyl, or $R_6$ and $R'_6$ together with the nitrogen atom to which they are attached form an optionally substituted 4-7 membered heterocycloaliphatic.

Another aspect of the present invention provides a method of modulating a muscarinic receptor comprising the step of contacting said receptor with a compound of formula I or a pharmaceutically acceptable salt thereof.

B. Specific Compounds

1. Substituent $R_1$:

$R_1$ is an optionally substituted aliphatic or —$NR_6R'_6$. Each of $R_6$ and $R'_6$ is independently hydrogen or an optionally substituted $C_{1-4}$ aliphatic. Alternatively, $R_6$ and $R'_6$ together with the nitrogen atom to which they are attached form an optionally substituted 4-7 membered heterocycloaliphatic.

In several embodiments, $R_1$ is an optionally substituted aliphatic. For example, $R_1$ is an alkyl, an alkenyl, or an alkynyl, each of which is optionally substituted. In several examples, $R_1$ is an optionally substituted methyl, ethyl, propyl, isopropyl, or butyl, each of which is optionally substituted. In other examples, $R_1$ is a methyl that is optionally substituted with 1-3 of halo, oxo, cyano, or nitro; or cycloaliphatic, heterocycloaliphatic, aryl, or heteroaryl, each of which is optionally substituted. In other examples, $R_1$ is an unsubstituted aliphatic. In several examples, $R_1$ is an unsubstituted alkyl.

In several embodiments $R_1$ is —$NR_6R'_6$ wherein each of $R_6$ and $R'_6$ is independently hydrogen or an optionally substituted $C_{1-4}$ aliphatic. In several examples, each $R_6$ and $R'_6$ is independently hydrogen or $C_{1-4}$ aliphatic that is that is optionally substituted with 1-3 of hydroxy, halo, cyano, nitro, or optionally substituted cycloaliphatic, optionally substituted heterocycloaliphatic, optionally substituted aryl, optionally substituted heteroaryl, or combinations thereof. In several examples, each $R_6$ and $R'_6$ are independently hydrogen, optionally substituted methyl, optionally substituted ethyl, or optionally substituted propyl. In other examples, both $R_6$ and $R'_6$ are methyl.

In some embodiments, $R_6$ and $R'_6$ together with the nitrogen atom to which they are attached form an optionally substituted 4-7 membered heterocycloaliphatic. For example, $R_6$ and $R'_6$ together with the nitrogen atom to which they are attached form an optionally substituted pyrrolidone-yl, an optionally substituted piperidine-yl, an optionally substituted azepane-yl, an optionally substituted airidine-yl, an optionally substituted azetidine-yl, or morpholine-yl.

In several examples, $R_1$ is one selected from N,N-dimethylamino and methyl.

In several alternative embodiments, $R_1$ is an optionally substituted $C_{3-6}$ cycloalkyl. For example, $R_1$ is an optionally substituted cyclopropyl, an optionally substituted cyclobutyl, an optionally substituted cyclopentyl, or an optionally substituted cyclohexyl.

2. Substituent $R_2$:

Each $R_2$ is a cycloaliphatic or a heterocycloaliphatic, each of which is optionally substituted with 1-3 of $R_3$. Each $R_3$ is -$Z^A R_4$, wherein each $Z^A$ is independently a bond or an optionally substituted branched or straight $C_{1-6}$ aliphatic chain wherein up to two carbon units of $Z^A$ are optionally and independently replaced by —CO—, —CS—, —$CONR^A$—, —$CONR^A NR^A$—, —$CO_2$—, —OCO—, —$NR^A CO_2$—, —O—, —$NR^A CONR^A$—, —$OCONR^A$—, —$NR^A NR^A$—, —$NR^A CO$—, —S—, —SO—, —$SO_2$—, $NR^A$—, —$SO_2 NR^A$—, —$NR^A SO_2$—, or —$NR^A SO_2 NR^A$—. Each $R_3$ is independently $R^A$, halo, —OH, —$NH_2$, —$NO_2$, —CN, or —$OCF_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments, $R_2$ is an optionally substituted cycloaliphatic. For example, $R_2$ is an optionally substituted monocyclic cycloaliphatic, an optionally substituted bicyclic cycloaliphatic, or an optionally substituted tricyclic cycloaliphatic. In several examples, $R_2$ is an optionally substituted monocyclic cycloaliphatic. In other examples, $R_2$ is an optionally substituted 3-9 membered monocyclic cycloaliphatic. In other examples, $R_2$ is cyclopropyl, cyclobutyl, cyclopentyl, cyclohexyl, cycloheptyl, or cyclooctyl, each of which is optionally substituted with 1-3 of halo, optionally substituted aliphatic, optionally substituted cycloaliphatic, optionally substituted heterocycloaliphatic, optionally substituted aryl, optionally substituted heteroaryl, optionally substituted alkoxycarbonyl, optionally substituted cycloalkoxycarbonyl, optionally substituted heterocycloalkoxycarbonyl, or combinations thereof. In several examples, $R_2$ is an optionally substituted bicyclic cycloaliphatic. In other examples, $R_2$ is an optionally substituted 5-10 membered bicyclic cycloaliphatic. In other examples, $R_2$ is bicyclo[2.1.1]hexyl, bicyclo[2.2.1]heptyl, bicyclo[3.1.1]heptyl, bicyclo[2.2.2]octyl, or bicyclo[3.2.1]octyl, each of which is optionally substituted. In other examples, $R_2$ is an optionally substituted tricyclic cycloaliphatic. In other examples, $R_2$ is an optionally substituted adamantyl. In several examples, $R_2$ is a monocyclic cycloaliphatic optionally substituted with a heteroaryl.

In several embodiments, $R_2$ is an optionally substituted heterocycloaliphatic. For example, $R_2$ is a monocyclic heterocycloaliphatic, a bicyclic heterocycloaliphatic, or a tricyclic heterocycloaliphatic. For example, $R_2$ is an optionally substituted monocyclic heterocycloaliphatic that has 1-3 heteroatoms independently selected from N, O, and S. In several examples, $R_2$ is an optionally substituted 5-9 membered monocyclic heterocycloaliphatic having 1 to 3 heteroatoms independently selected from N, O, and S. For example, $R_2$ is pyrrolidine-yl, 1,3-dioxolane-yl, imidazolidine-yl, 2-pyrazoline-yl, pyrazolidine-yl, piperidine-yl, 1,4-dioxane-yl, morpholine-yl, azepane-yl, azocane-yl, or piperazine-yl, each of which is optionally substituted with 1 to 3 of halo, or aliphatic, alkoxy, (aliphatic(oxy))carbonyl, (alkoxy(alkoxy))carbonyl, cycloaliphatic, heterocycloaliphatic, aryl, heteroaryl, acyl, amido, amino, (heterocycloaliphatic)oxy, (heterocycloaliphatic(oxy))carbonyl, each of which is optionally substituted. In other examples, $R_2$ is an optionally substituted bicyclic heterocycloaliphatic that has 1-3 heteroatoms independently selected from N, O, and S. In several examples, $R_2$ is an optionally substituted 7-10 membered bicyclic heterocycloatiphatic having 1 to 3 heteroatoms independently selected from N, O, and S. In other examples, $R_2$ is a bridged bicyclic heterocycloaliphatic or a fused bicyclic heterocycloaliphatic, each of which is optionally substituted. For example, $R_2$ is 5-azabicyclo[2.1.1]hexane-yl, 7-azabicyclo[2.2.1]heptane-yl, or 8-azabicyclo[3.2.1]octane-yl, each of which is optionally substituted with 1-3 of halo, or aliphatic, alkoxy, (aliphatic(oxy))carbonyl, (alkoxy(alkoxy))carbonyl, cycloaliphatic, heterocycloaliphatic, aryl, heteroaryl, acyl, amido, amino, (heterocycloaliphatic)oxy, (heterocycloaliphatic(oxy))carbonyl, each of which is optionally substituted.

In several embodiments, $R_2$ is one selected from: 1-methoxycarbonylpiperidine-4-yl; 1-ethoxycarbonylpiperidine-4-yl; propoxycarbonylpiperidine-4-yl; 1-isopropoxycarbonylpiperidine-4-yl; 1-((2,2-difluoroethoxy)carbonyl)piperidine-4-yl; 1-(2-methoxy(ethoxy)carbonyl)piperidine-4-yl; 1-((3-butynoxy)carbonyl)piperidine-4-yl; 8-(methoxy(carbonyl))-8-azabicyclo[3.2.1]octane-3-yl; 8-(ethoxy(carbonyl))-8-azabicyclo[3.2.1]octane-3-yl; 8-(propoxy(carbonyl))-8-azabicyclo[3.2.1]octane-3-yl; 8-(isopropoxycarbonyl)-8-azabicyclo[3.2.1]octane-3-yl; 8-((2,2-difluoroethoxy)carbonyl)-8-azabicyclo[3.2.1]octane-3-yl; 8-(methoxy(ethoxy)carbonyl)-8-azabicyclo[3.2.1]

octane-3-yl; 8-(3-butynyloxy(carbonyl))-8-azabicyclo [3.2.1]octane-3-yl; 1-(pyrazine-2-yl)piperidine-4-yl; 1-(1,2,4-thiadiazole-5-yl)piperidine-4-yl; 1-(methoxy(carbonyl)) pyrrolidine-3-yl; 1-(ethoxy(carbonyl))pyrrolidine-3-yl; 1-(isopropoxy(carbonyl))pyrrolidine-3-yl; 1-((2,2-difluoroethoxy)carbonyl)pyrrolidine-3-yl; 1-(2-(methoxy(ethoxy)) carbonyl)pyrrolidone-3-yl; 1-(propoxy(carbonyl))pyrrolidine-3-yl; 1-((2,2-difluoroethoxy)carbonyl)pyrrolidone-3-yl; 8-(3-methyl(1,2,4-thiadiazole-5-yl))-8-azabicyclo[3.2.1] octane-3-yl; 8-(3-ethyl(1,2,4-thiadiazole-5-yl))-8-azabicyclo[3.2.1]octane-3-yl; 1-(methoxy(carbonyl)) azepane-4-yl; 1-(ethoxy(carbonyl))azepane-4-yl; 1-(propoxy(carbonyl))azepane-4-yl; 1-(isopropoxy(carbonyl))azepane-4-yl; 1-((2,2-difluoroethoxy)carbonyl) azepane-4-yl; 1-(2-(methoxy(ethoxy))carbonyl)azepane-4-yl; (tetrahydrofuran-3-yl(oxy(carbonyl)))azepane-4-yl; (tetrahydrofuran-3-yl(oxy(carbonyl)))pyrrolidine-3-yl; 4-(3-methyl(1,2,4-thiadiazole-5-yl))cyclohexane-1-yl; 1-(1,2,4-thiadiazole-5-yl)piperidine-4-yl; 1-(3-ethyl(1,2,4-thiadiazole-5-yl))piperidine-4-yl; 1-(6-chloro(pyrazine-2-yl)) piperidine-4-yl; 1-(quinoxaline-2-yl)piperidine-4-yl; 1-(6-methyl(pyrazine-2-yl))piperidine-4-yl; 1-(methoxy (carbonyl))azocane-5-yl; 1-(ethoxy(carbonyl))-4-methylpiperidine-4-yl; 1-(pyrazine-2-yl-(4-methyl)) piperidine-4-yl; 1-(3-methyl-(1,2,4-thiadiazole-5-yl)) pyrrolidine-3-yl; 1-(3-ethyl-(1,2,4-thiadiazole-5-yl)) pyrrolidine-3-yl; 1-((5,6-dimethyl(pyrazine-2-yl))) pyrrolidine-3-yl; 1-((5,6-dimethyl(pyrazine-2-yl))) piperidine-4-yl; 1-(1,2,4-thiadiazole-5-yl)piperidine-4-yl; 1-(thiazole-2-yl)piperidine-4-yl; 1-(4-methyl(thiazole-2-yl)) piperidine-4-yl; 4-(1,2,4-thiadiazole-5-yl)cyclohexane-1-yl; 1-(2-hydroxy-(6-phenyl-(pyrazine-6-yl)))piperidine-4-yl; 1-(6-(2-hydroxyphenyl)pyrazine-2-yl)piperidin-4-yl; 1-(5-methyl(thiazole-2-yl))piperidine-4-yl; 1-(benzo[d]thiazole-2-yl)piperidine-4-yl; 1-(benzo[d]oxazole-2-yl)piperidine-4-yl; 1-(prop-2-ynyl(oxy(carbonyl)))piperidine-4-yl; 1-(pent-2-ynyl(oxy(carbonyl)))piperidine-4-yl; 8-(prop-2-ynyl(oxy (carbonyl)))-8-azabicyclo[3.2.1]octane-3-yl; 8-(but-2-ynyl (oxy(carbonyl)))-8-azabicyclo[3.2.1]octane-3-yl; 1-(prop-2-ynyl(oxy(carbonyl)))pyrrolidine-3-yl; 1-(but-2-ynyl(oxy (carbonyl)))pyrrolidine-3-yl; 1-(pent-2-ynyl(oxy (carbonyl)))pyrrolidine-3-yl; 8-(pyrazine-2-yl)-8-azabicyclo [3.2.1]octane-3-yl; 1-(prop-2-ynyl(oxy(carbonyl)))azepane-4-yl; 1-(but-2-ynyl(oxy(carbonyl)))azepane-4-yl; 1-(pent-2-ynyl(oxy(carbonyl)))azepane-4-yl; 1-(ethoxy(carbonyl)) azocane-5-yl; 1-(pyrazine-2-yl)pyrrolidone-3-yl; and piperidine-4-yl.

3. L Groups and p:

Each L is —(CH$_2$)$_n$—, wherein n is 0-2.

In several embodiments, L is a bond or an unsubstituted methylene group.

p is 0 or 1.

C. Subgeneric Compounds

Another aspect of the present invention provides compounds of formulae Ia and Ib that are useful for modulating the activity and/or activities of muscarinic receptor(s) in accordance to formulae Ia and Ib respectively:

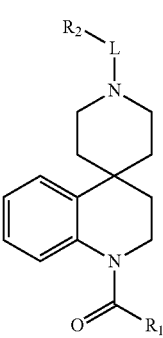

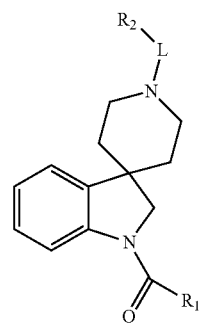

or pharmaceutically acceptable salts thereof, wherein $R_1$, $R_2$, and L are defined in formula I above.

Another aspect of the present invention provides compounds of formula Ic that are useful for modulating the activity and/or activities of muscarinic receptor(s) in accordance to formula Ic:

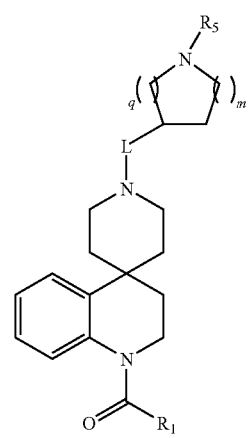

or a pharmaceutically acceptable salt thereof, wherein $R_1$ and L are defined in formula I above.

$R_5$ is -$Z^B R_7$, wherein each $Z^B$ is independently a bond or an optionally substituted branched or straight $C_{1-6}$ aliphatic chain wherein up to two carbon units of $Z^B$ are optionally and independently replaced by —CO—, —OCO—, —COO—, —CONR$^C$—, or —O—. Each $R_7$ is independently $R^C$, halo, —OH, —NH$_2$, —NO$_2$, —CN, or —OCF$_3$. Each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

q+m is 2-5.

In several embodiments, q is 1-3. In other embodiments, m is 1-3. For example, both q and m are 1.

In several embodiments, $R_5$ is an optionally substituted —$CO_2$-alkyl or an optionally substituted —$CO_2$-cycloaliphatic. In several examples, $R_5$ is —$CO_2$—$CH_3$, or —$CO_2$—$CH_2$—$CH_3$.

In additional embodiments, $R_5$ is an optionally substituted aryl or an optionally substituted heteroaryl. For example, $R_5$ is an optionally substituted phenyl. In other examples, $R_5$ is a furan-yl, thiophene-yl, pyridazine-yl, pyrimidine-yl, pyrazine-yl, pyridine-yl, 1,3,4-thiadiazole-yl, or pyrazole-yl, each of which is optionally substituted.

Another aspect of the present invention provides compounds of formula Id that are useful for modulating the activity and/or activities of muscarinic receptor(s) in accordance to formula Id:

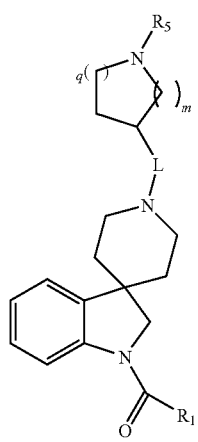

Id or a pharmaceutically acceptable salt thereof, wherein L is defined in formula I and $R_5$, and q and m are defined in formula Ic.

$R_1$ is an optionally substituted $C_{2-8}$ alkyl, alkenyl, alkynyl, N,N-dimethylamino, or —$NR_6R'_6$. Each of $R_6$ and $R'_6$ is independently hydrogen or an optionally substituted $C_{1-4}$ aliphatic. Alternatively, $R_6$ and $R'_6$ together with the nitrogen atom to which they are attached form an optionally substituted 4-7 membered heterocycloaliphatic.

In several embodiments, $R_5$ is an optionally substituted —$CO_2$-alkyl or an optionally substituted —$CO_2$-cycloaliphatic. In several examples, $R_5$ is —$CO_2$—$CH_3$, or —$CO_2$—$CH_2$—$CH_3$.

Another aspect of the present invention provides of formula II that are useful for modulating the activity and/or activities of muscarinic receptor(s) in accordance to formula II:

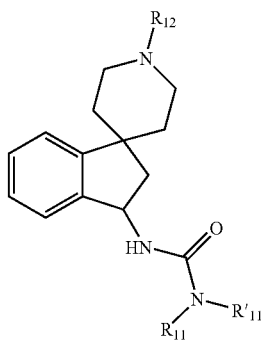

II or a pharmaceutically acceptable salt thereof, wherein

Each $R_{11}$ and $R'_{11}$ is independently hydrogen or aliphatic optionally substituted with 1-3 of halo, cyano, hydroxy, nitro, or combinations thereof; and Each $R_{12}$ is an optionally substituted 7-9 membered bicyclic cycloalkyl.

In several embodiments, each $R_{11}$ and $R'_{11}$ is independently hydrogen or an alkyl optionally substituted with 1-3 of halo, cyano, hydroxy, nitro, or combinations thereof. For example, each $R_{11}$ and $R'_{11}$ is independently methyl, ethyl, propyl, or butyl, each of which is optionally substituted with 1-3 of halo, cyano, hydroxy, nitro, or combinations thereof. In several additional examples, both of $R_{11}$ and $R'_{11}$ are unsubstituted methyl.

In several embodiments, $R_{12}$ is an optionally substituted 7-9 membered bicyclic cycloalkyl. For example, $R_{12}$ is a bicyclo[3.2.1]octane-yl, bicyclo[2.2.2]octane-yl, bicyclo[2.2.1]heptane-yl, or bicyclo[3.1.1]heptane-yl, each of which is optionally substituted. In other examples, $R_{12}$ is an unsubstituted bicyclo[2.2.1]heptane-yl.

C. Combinations of Embodiments

Other embodiments include any combination of the aforementioned substituents $R_1$, $R_2$, L, and p.

D. Specific Embodiments

Specific exemplary compounds of formulae (I, Ia, Ib, Ic, Id, and II) are shown below in Table 1.

TABLE 1

Exemplary compounds of formulae (I, Ia, Ib, Ic, Id, and II).

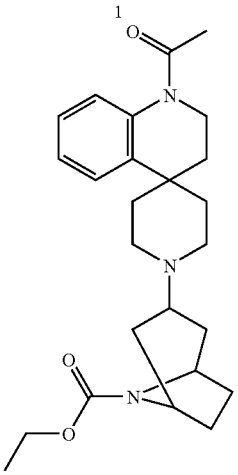

1

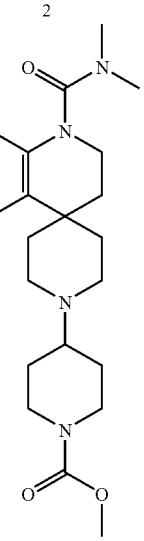

2

TABLE 1-continued
Exemplary compounds of formulae (I, Ia, Ib, Ic, Id, and II).
3
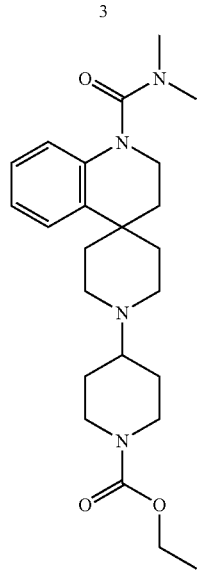
4
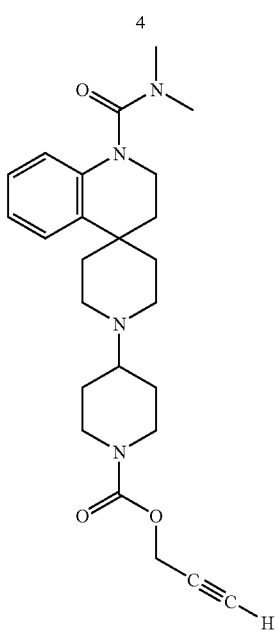
TABLE 1-continued
Exemplary compounds of formulae (I, Ia, Ib, Ic, Id, and II).
5
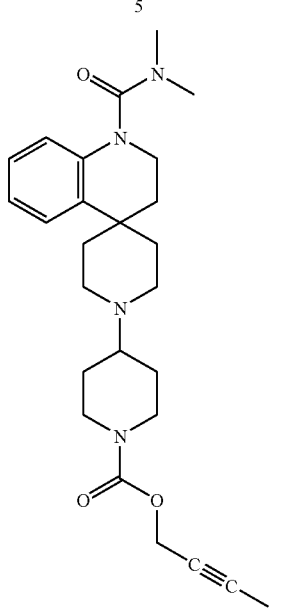
6
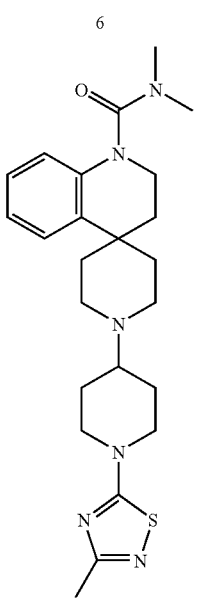

TABLE 1-continued
Exemplary compounds of formulae (I, Ia, Ib, Ic, Id, and II).
7
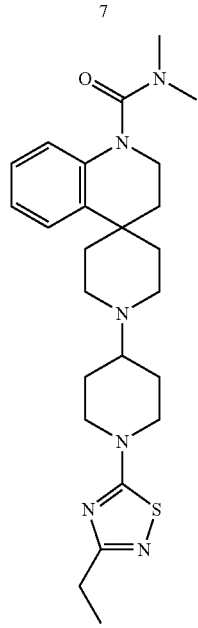
8
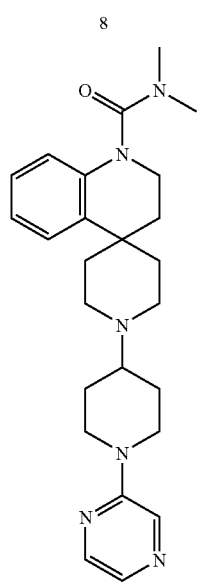
TABLE 1-continued
Exemplary compounds of formulae (I, Ia, Ib, Ic, Id, and II).
9
10
11
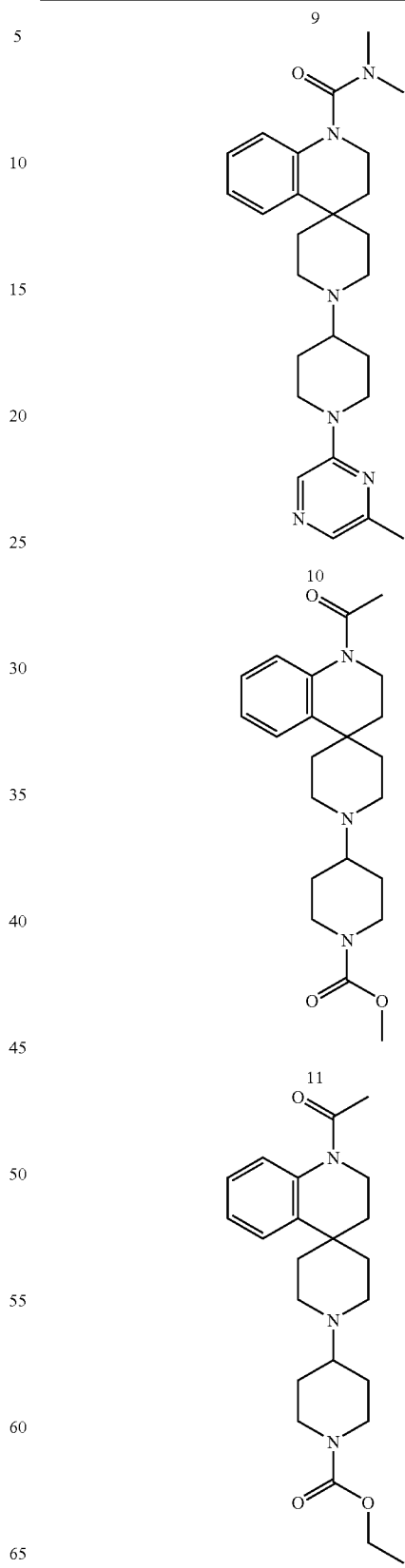

TABLE 1-continued
Exemplary compounds of formulae (I, Ia, Ib, Ic, Id, and II).
12
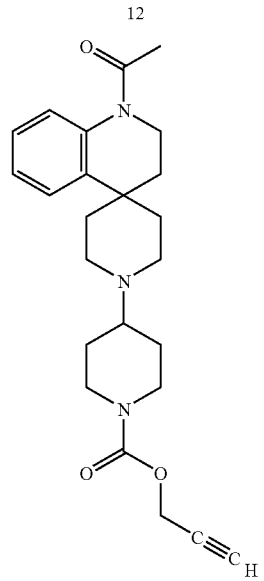
13
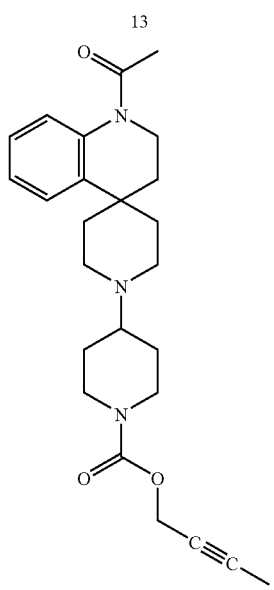
TABLE 1-continued
Exemplary compounds of formulae (I, Ia, Ib, Ic, Id, and II).
14
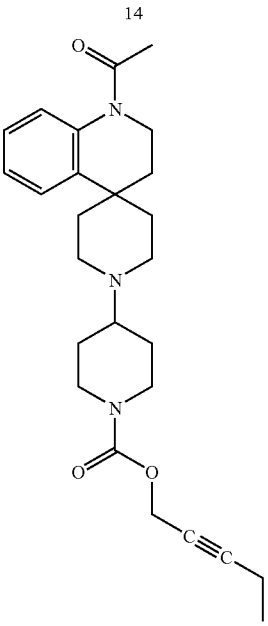
15
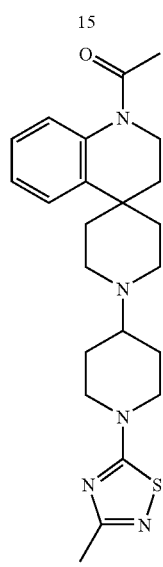

TABLE 1-continued
Exemplary compounds of formulae (I, Ia, Ib, Ic, Id, and II).
16
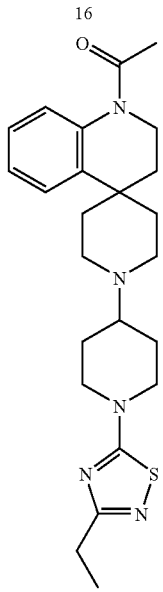
17
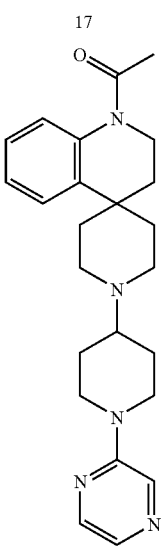
TABLE 1-continued
Exemplary compounds of formulae (I, Ia, Ib, Ic, Id, and II).
18
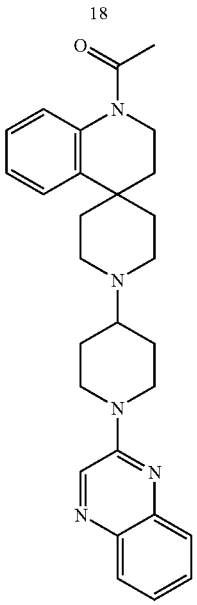
19
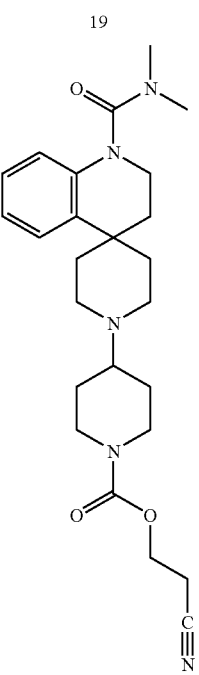

TABLE 1-continued
Exemplary compounds of formulae (I, Ia, Ib, Ic, Id, and II).
20
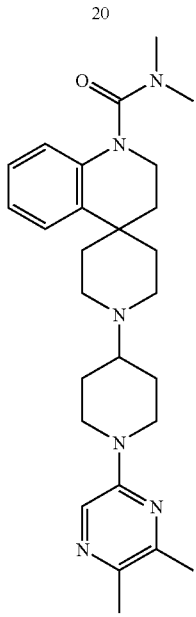
21
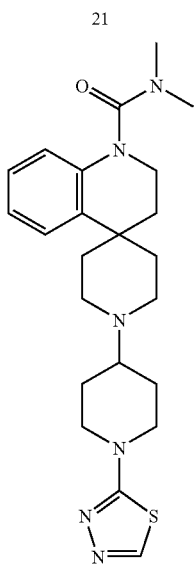
22
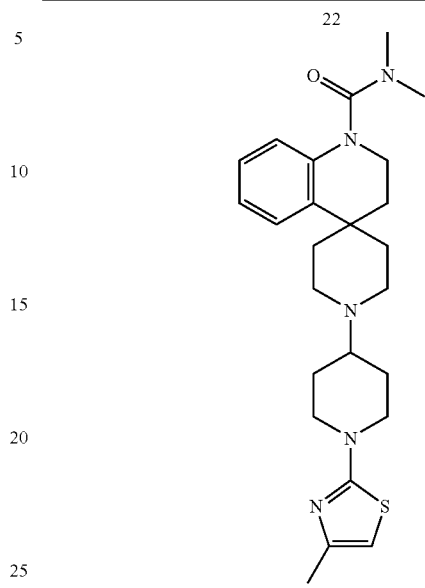
23
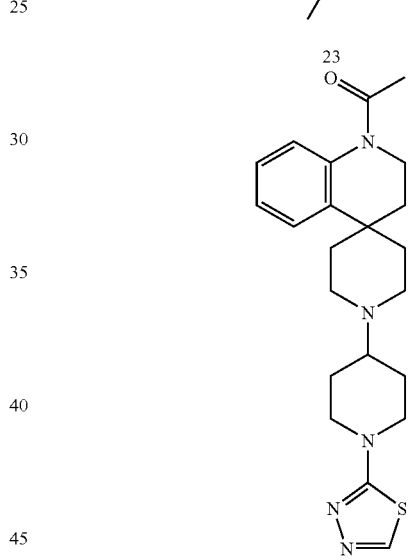
24
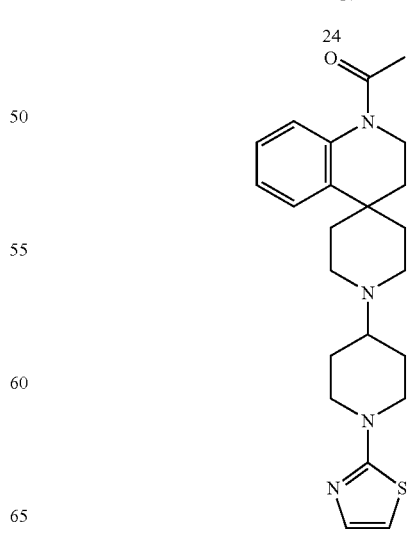

TABLE 1-continued
Exemplary compounds of formulae (I, Ia, Ib, Ic, Id, and II).
25
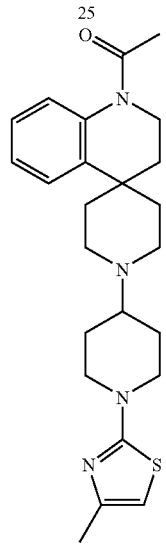
26
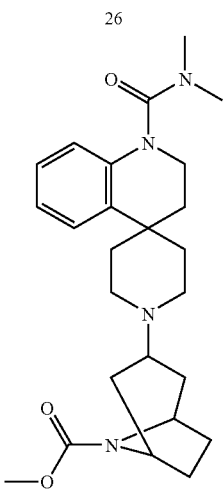
27
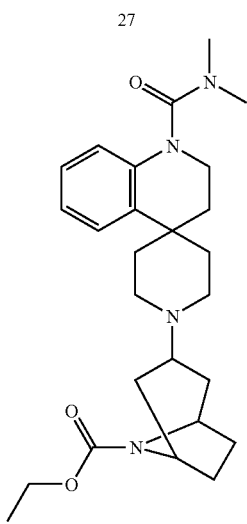
TABLE 1-continued
Exemplary compounds of formulae (I, Ia, Ib, Ic, Id, and II).
28
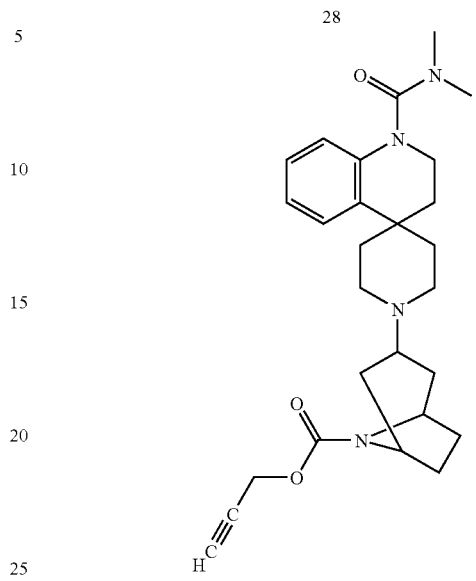
29
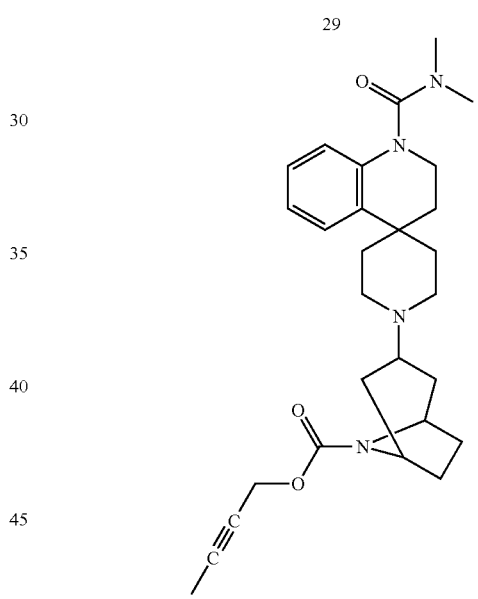
30
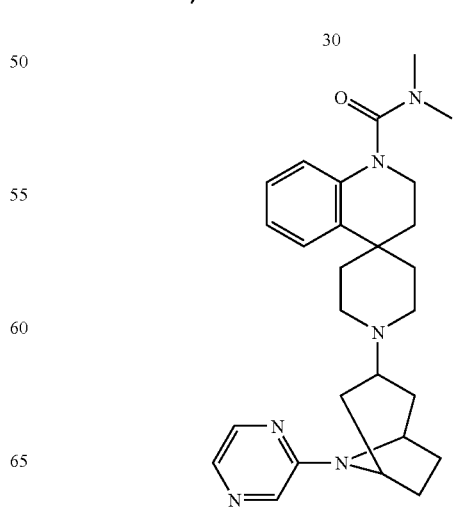

TABLE 1-continued
Exemplary compounds of formulae (I, Ia, Ib, Ic, Id, and II).
31
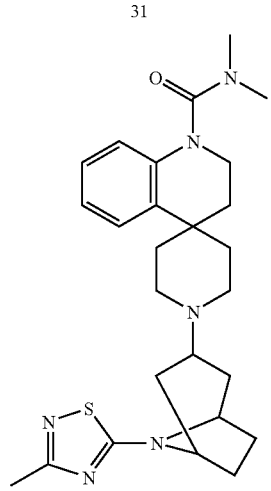
32
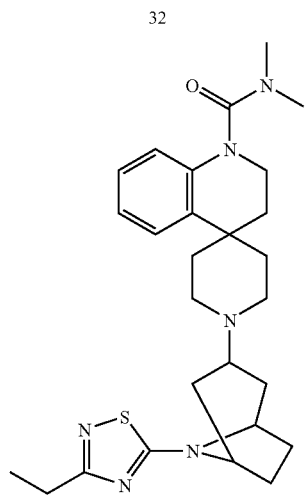
33
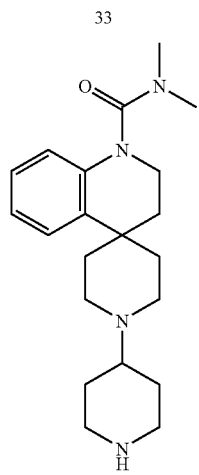
TABLE 1-continued
Exemplary compounds of formulae (I, Ia, Ib, Ic, Id, and II).
34
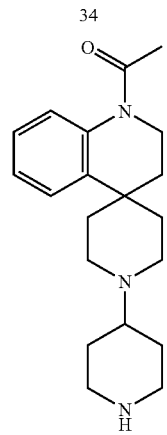
35
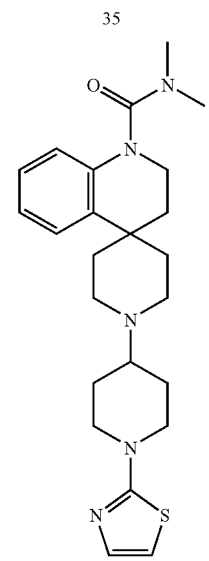
36
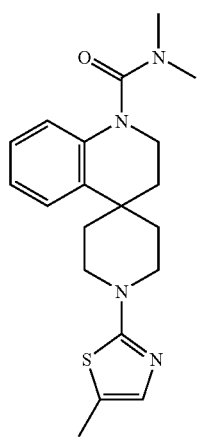

TABLE 1-continued
Exemplary compounds of formulae (I, Ia, Ib, Ic, Id, and II).
37
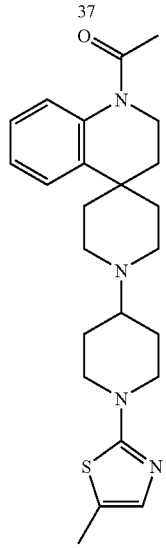
38
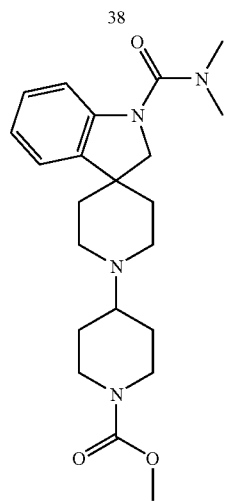
39
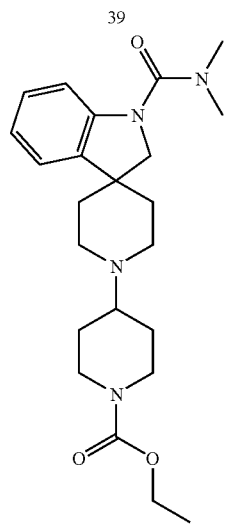
TABLE 1-continued
Exemplary compounds of formulae (I, Ia, Ib, Ic, Id, and II).
40
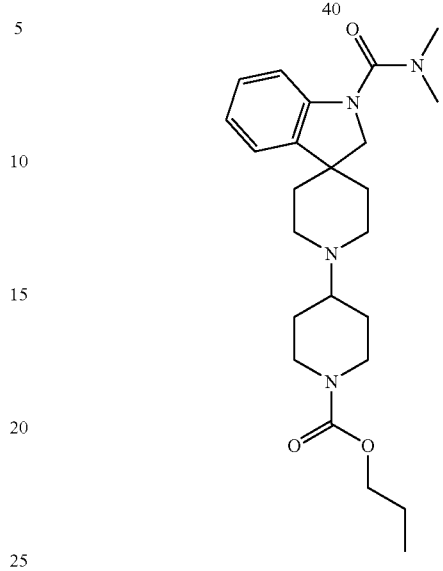
41
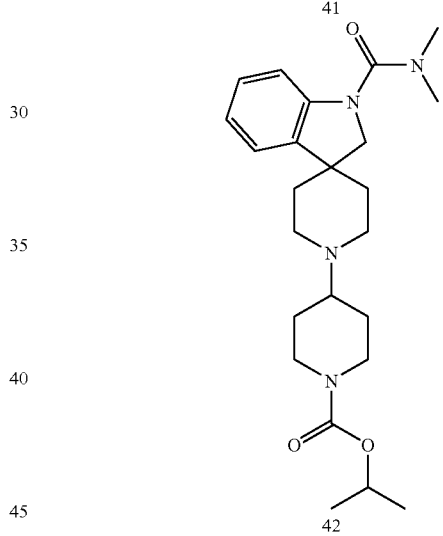
42
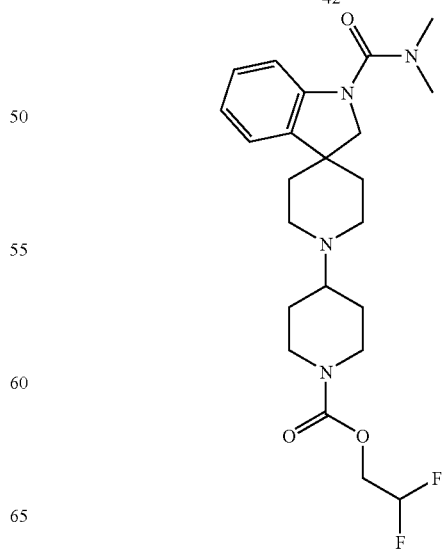

TABLE 1-continued
Exemplary compounds of formulae (I, Ia, Ib, Ic, Id, and II).
43
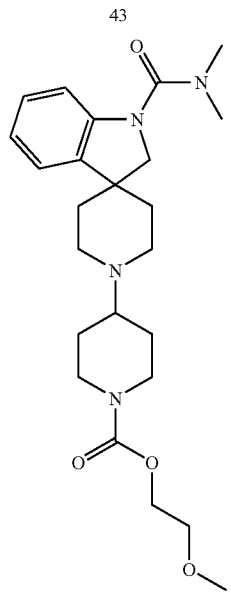
44
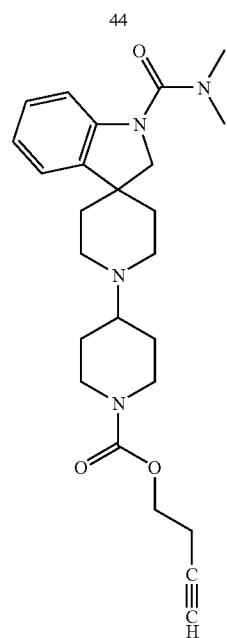
45
46
47
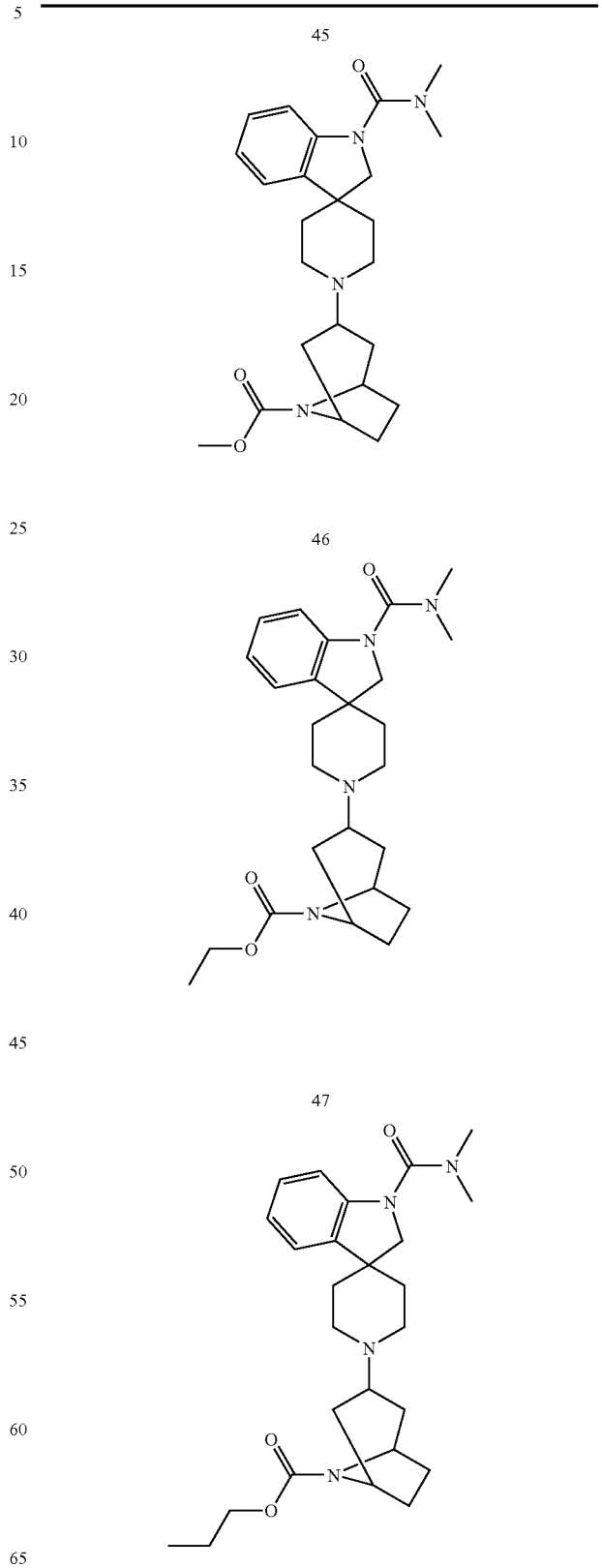

TABLE 1-continued
Exemplary compounds of formulae (I, Ia, Ib, Ic, Id, and II).
48
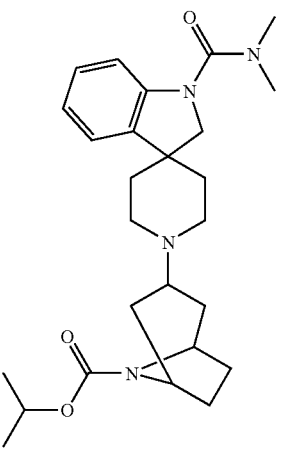
49
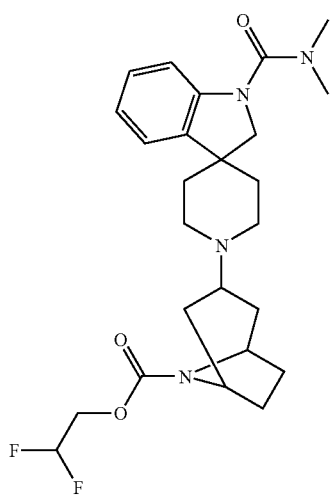
50
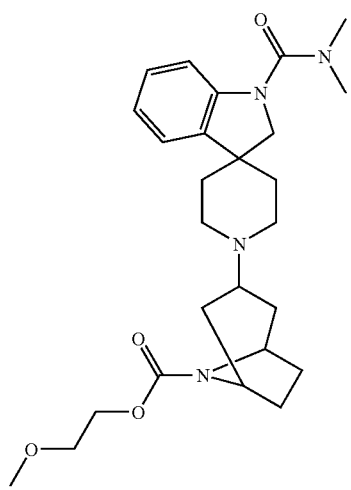
TABLE 1-continued
Exemplary compounds of formulae (I, Ia, Ib, Ic, Id, and II).
51
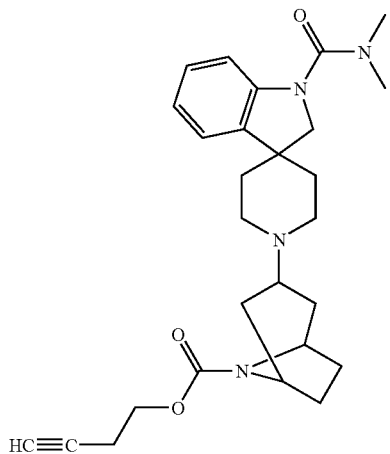
52
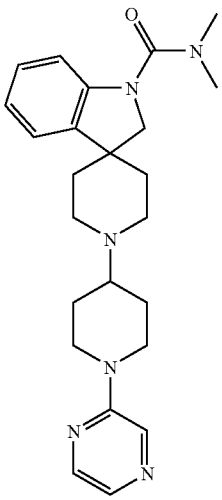
53
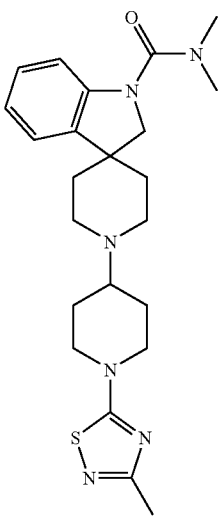

TABLE 1-continued
Exemplary compounds of formulae (I, Ia, Ib, Ic, Id, and II).
54
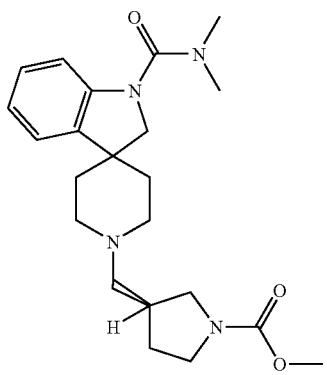
55
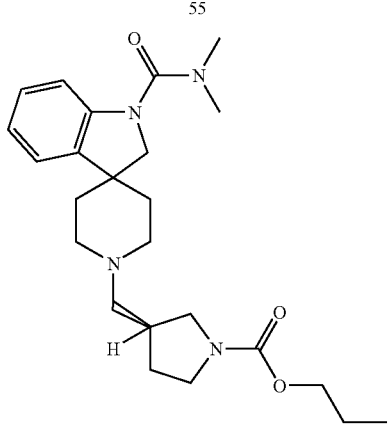
56
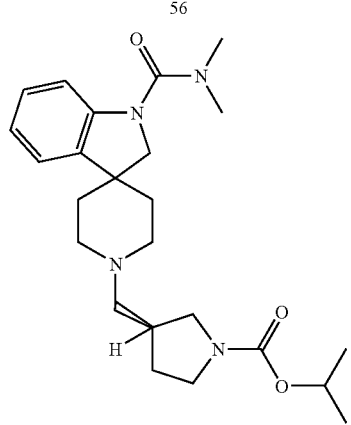
TABLE 1-continued
Exemplary compounds of formulae (I, Ia, Ib, Ic, Id, and II).
57
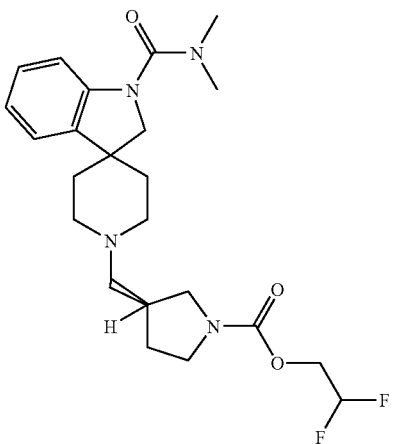
58
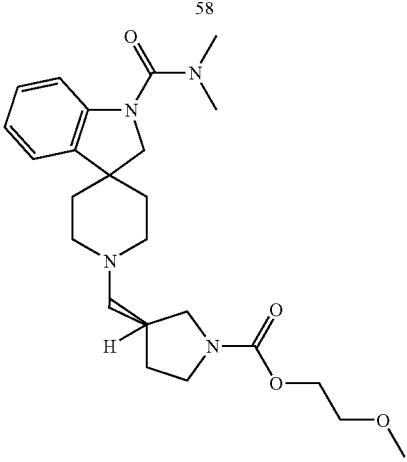
59
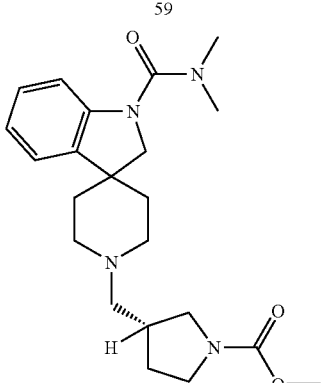

TABLE 1-continued
Exemplary compounds of formulae (I, Ia, Ib, Ic, Id, and II).
60
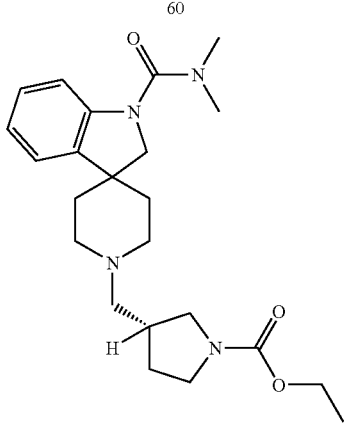
61
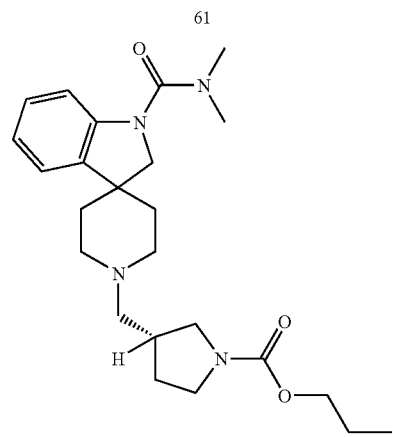
62
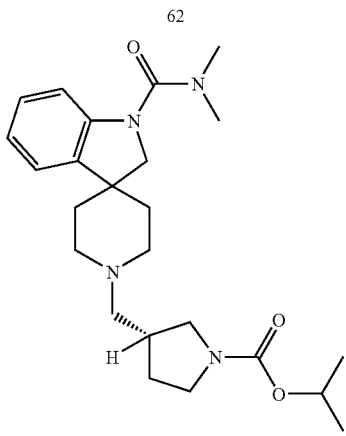
TABLE 1-continued
Exemplary compounds of formulae (I, Ia, Ib, Ic, Id, and II).
63
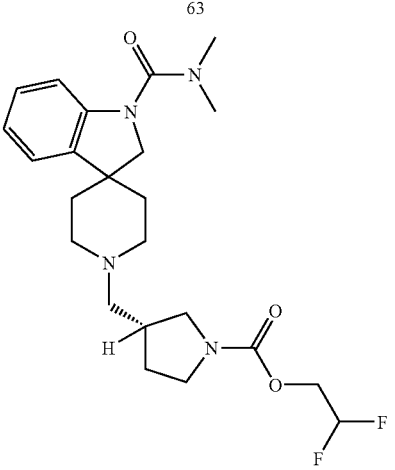
64
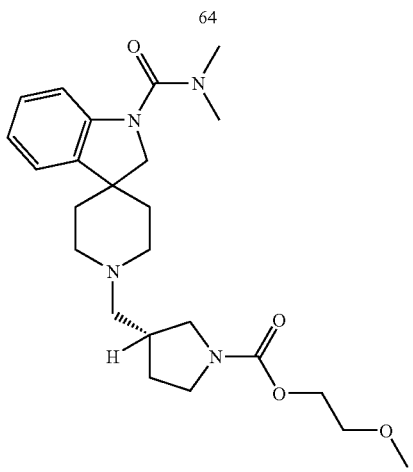
65
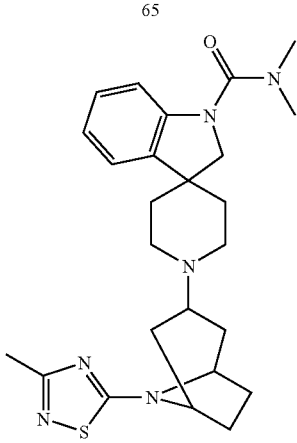

TABLE 1-continued
Exemplary compounds of formulae (I, Ia, Ib, Ic, Id, and II).
66
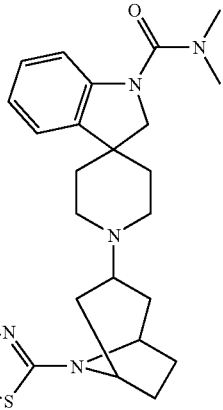
67
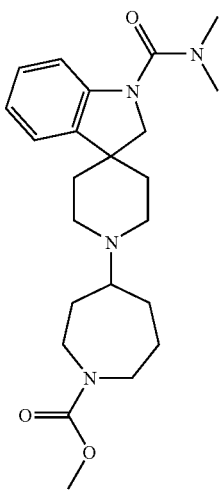
68
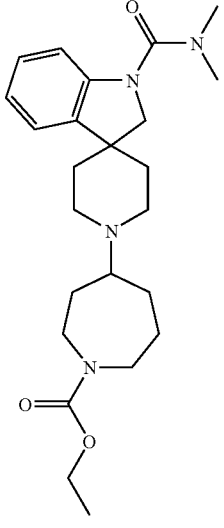
TABLE 1-continued
Exemplary compounds of formulae (I, Ia, Ib, Ic, Id, and II).
69
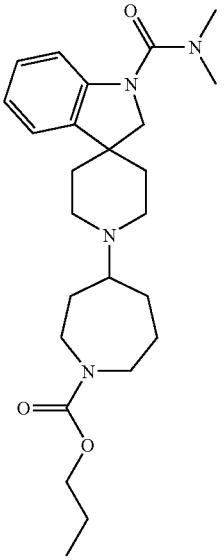
70
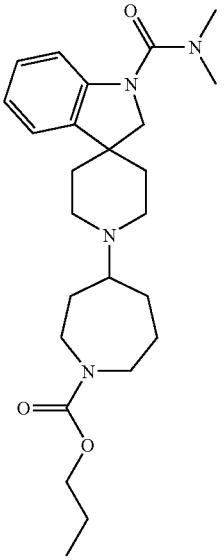

TABLE 1-continued
Exemplary compounds of formulae (I, Ia, Ib, Ic, Id, and II).
71
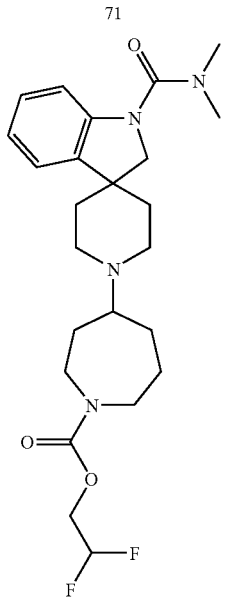
72
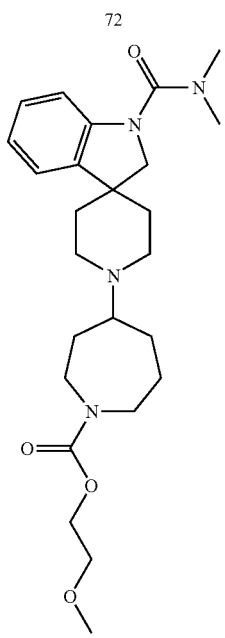
TABLE 1-continued
Exemplary compounds of formulae (I, Ia, Ib, Ic, Id, and II).
73
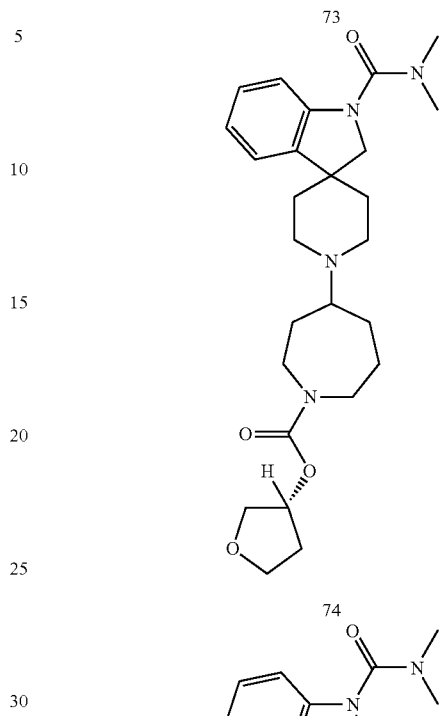
74
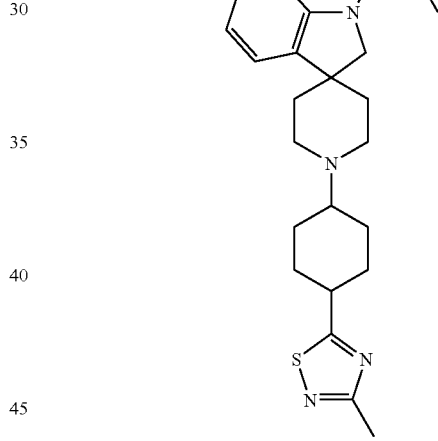
75
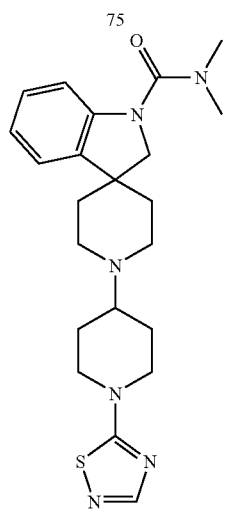

TABLE 1-continued
Exemplary compounds of formulae (I, Ia, Ib, Ic, Id, and II).
76
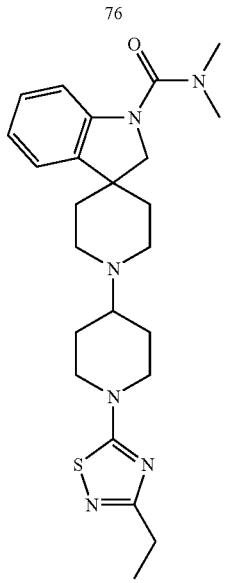
77
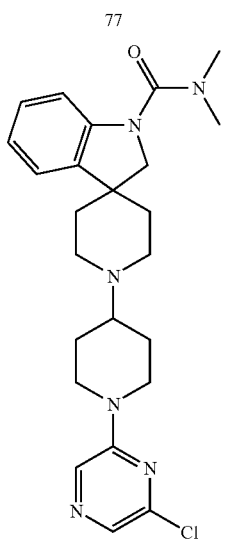
TABLE 1-continued
Exemplary compounds of formulae (I, Ia, Ib, Ic, Id, and II).
78
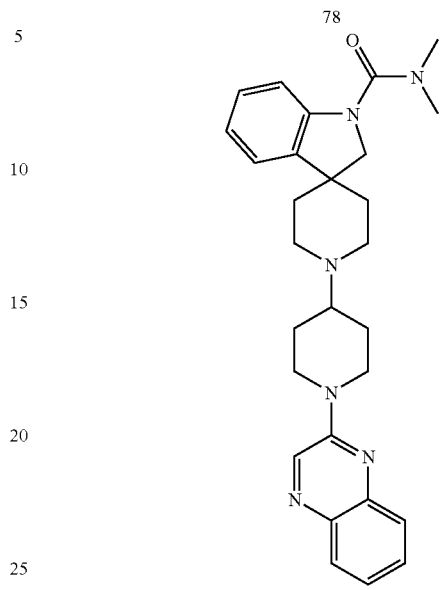
79
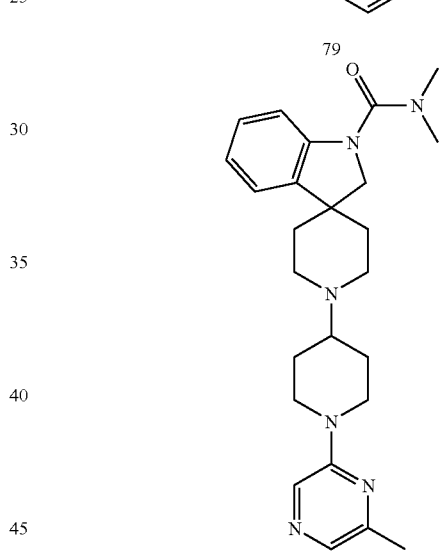
80
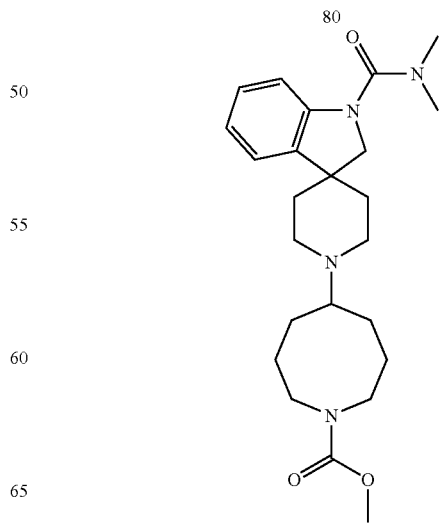

TABLE 1-continued
Exemplary compounds of formulae (I, Ia, Ib, Ic, Id, and II).
81
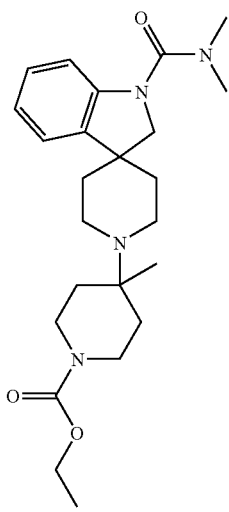
82
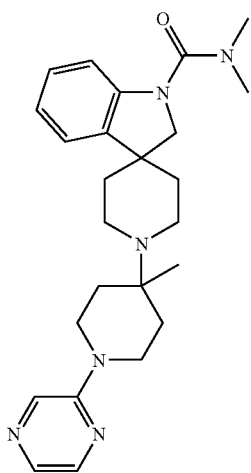
83
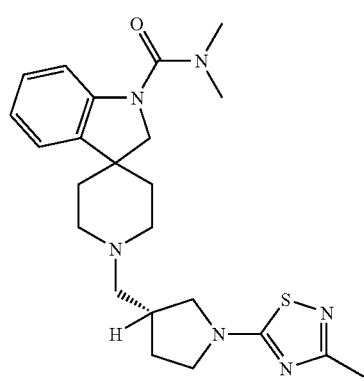
TABLE 1-continued
Exemplary compounds of formulae (I, Ia, Ib, Ic, Id, and II).
84
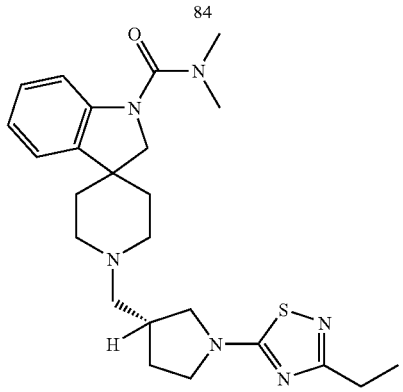
85
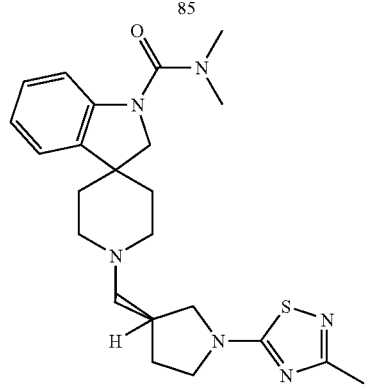
86
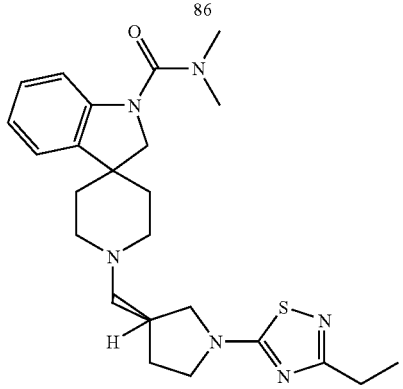
87
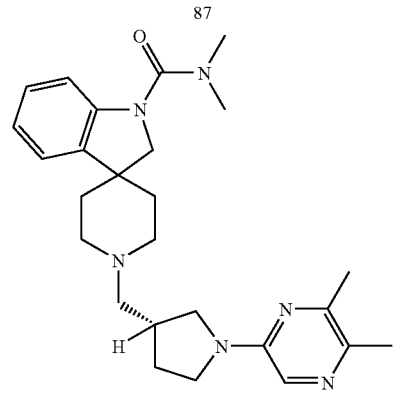

TABLE 1-continued
Exemplary compounds of formulae (I, Ia, Ib, Ic, Id, and II).
88
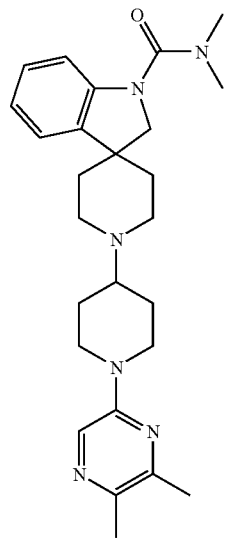
89
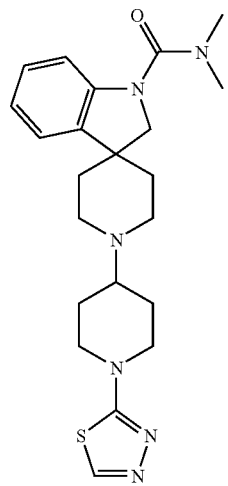
90
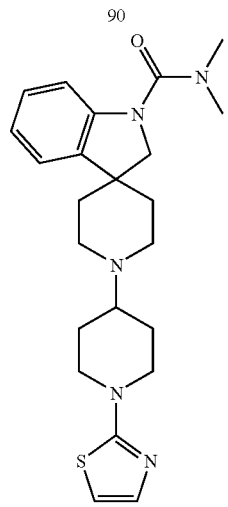
TABLE 1-continued
Exemplary compounds of formulae (I, Ia, Ib, Ic, Id, and II).
91
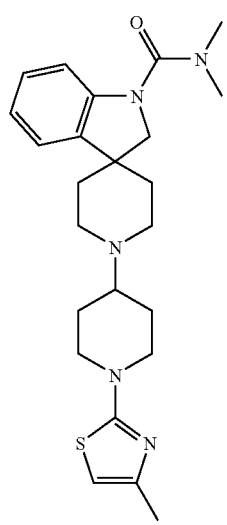
92
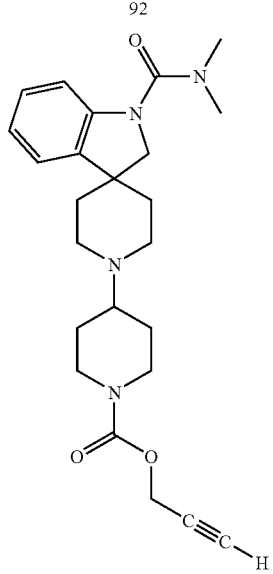

TABLE 1-continued
Exemplary compounds of formulae (I, Ia, Ib, Ic, Id, and II).
93
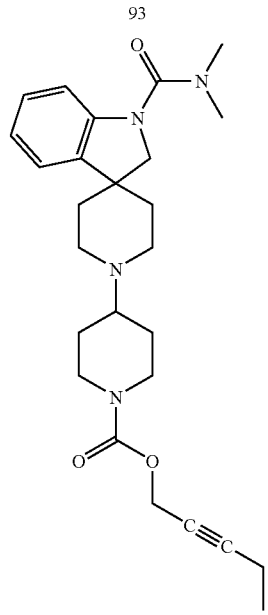
94
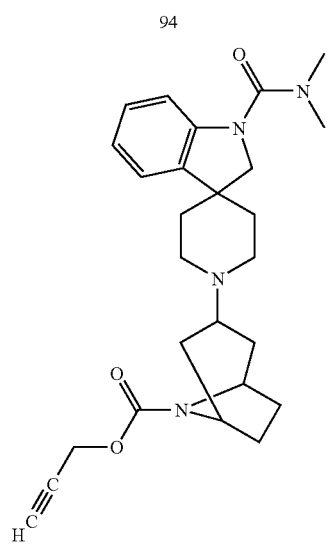
TABLE 1-continued
Exemplary compounds of formulae (I, Ia, Ib, Ic, Id, and II).
95
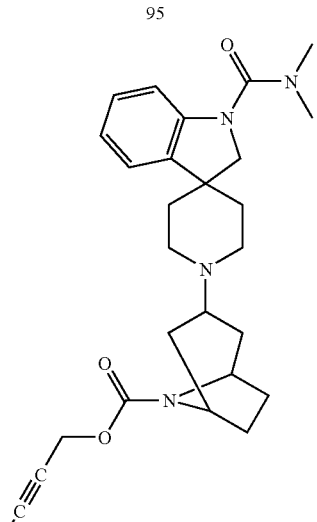
96
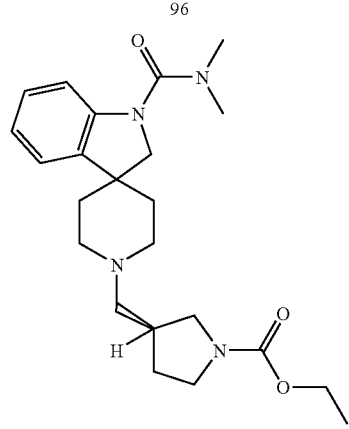
97
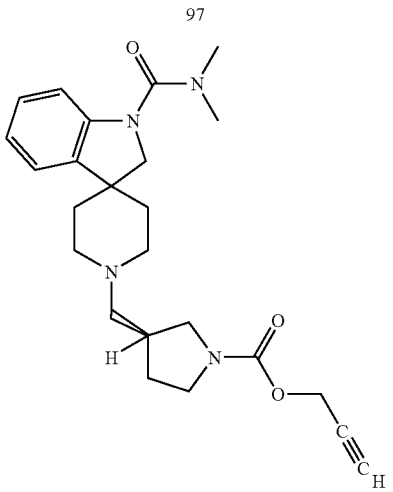

TABLE 1-continued
Exemplary compounds of formulae (I, Ia, Ib, Ic, Id, and II).
98
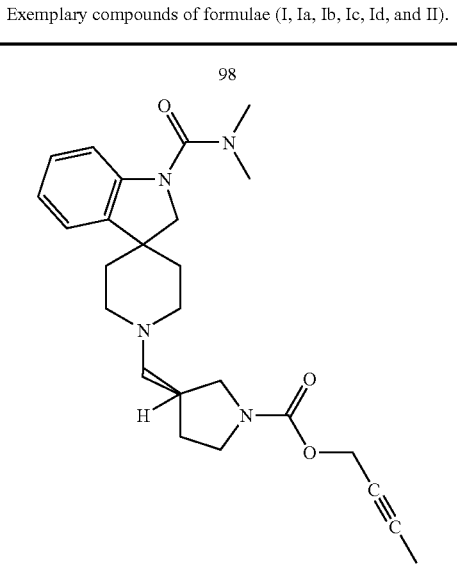
99
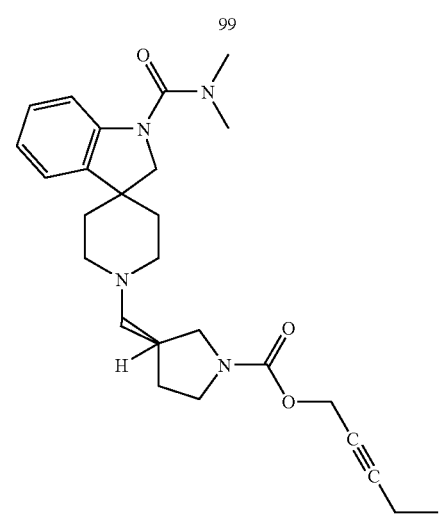
100
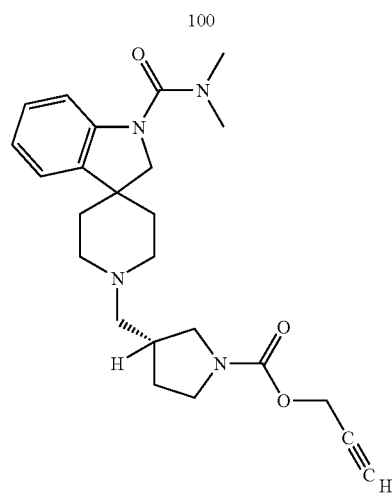
TABLE 1-continued
Exemplary compounds of formulae (I, Ia, Ib, Ic, Id, and II).
101
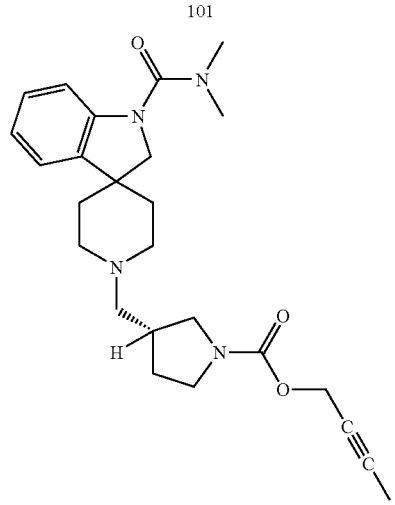
102
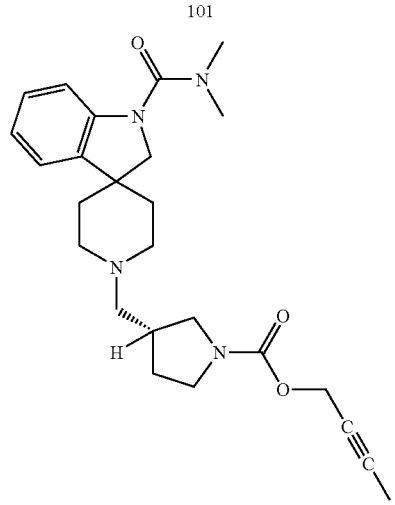
103
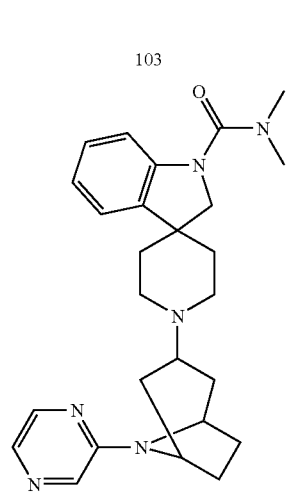

TABLE 1-continued
Exemplary compounds of formulae (I, Ia, Ib, Ic, Id, and II).
104
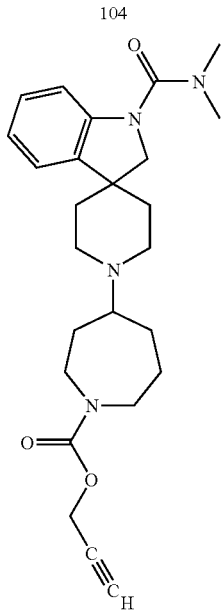
105
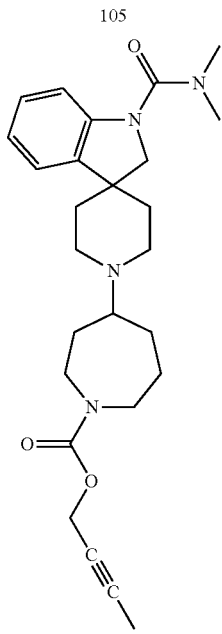
106
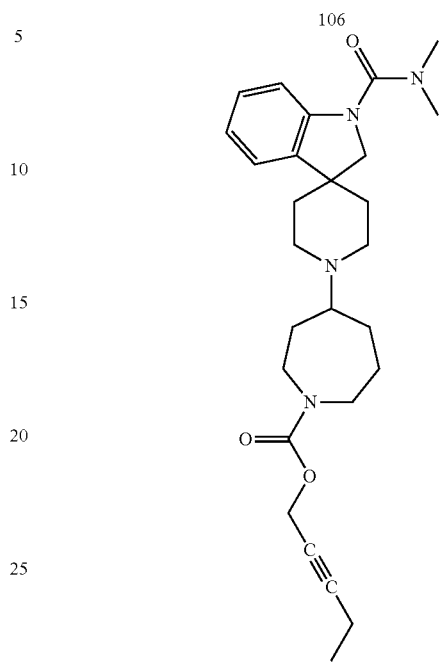
107
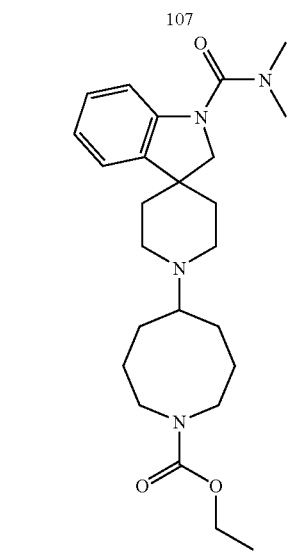
108
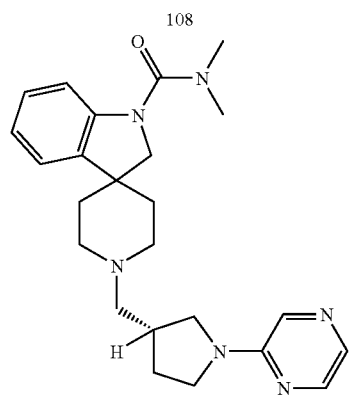

TABLE 1-continued
Exemplary compounds of formulae (I, Ia, Ib, Ic, Id, and II).
109
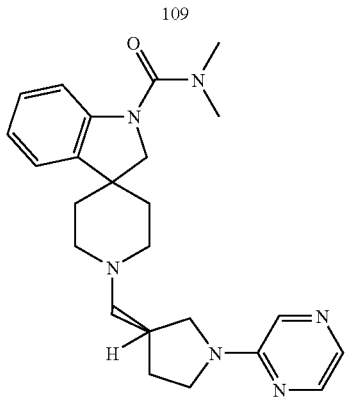
110
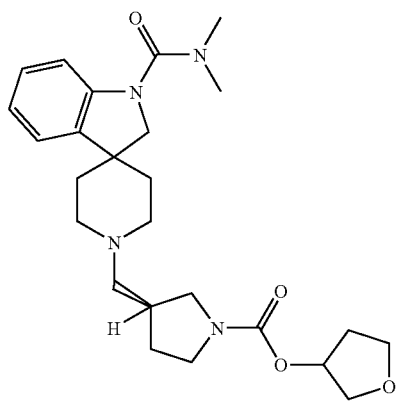
111
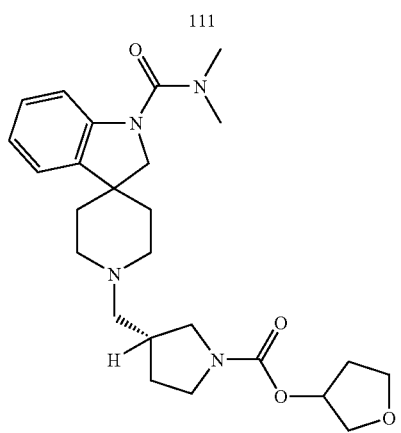
TABLE 1-continued
Exemplary compounds of formulae (I, Ia, Ib, Ic, Id, and II).
112
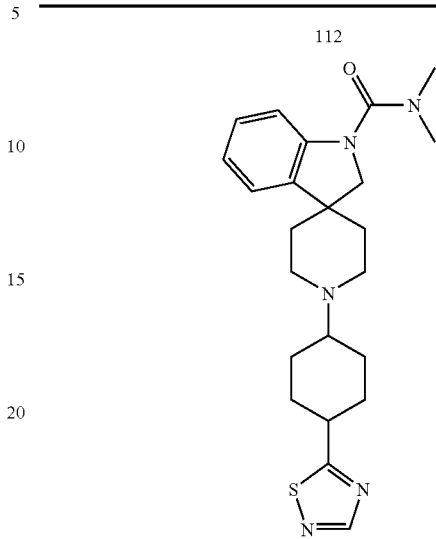
113
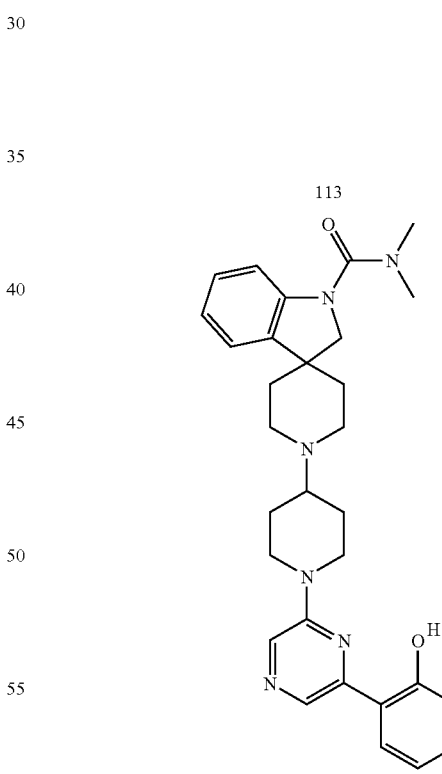

TABLE 1-continued
Exemplary compounds of formulae (I, Ia, Ib, Ic, Id, and II).
114
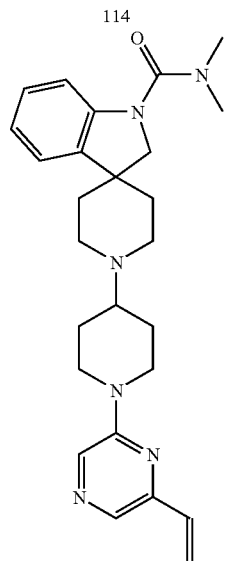
115
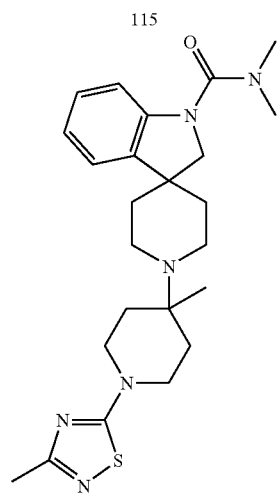
116
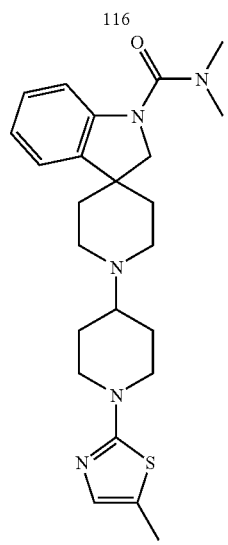
TABLE 1-continued
Exemplary compounds of formulae (I, Ia, Ib, Ic, Id, and II).
117
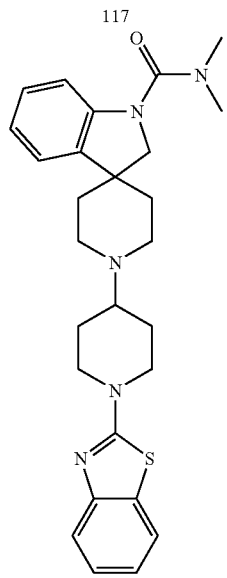
118
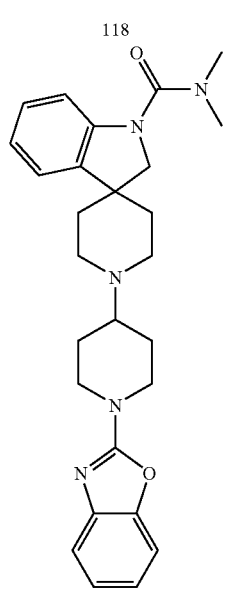
119
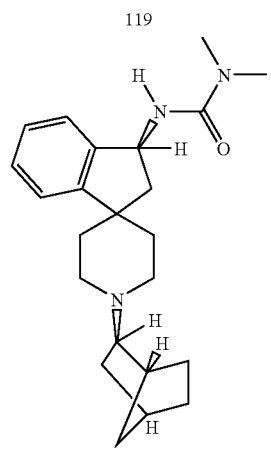

II. Synthetic Schemes

The compounds of formulae (I, Ia, Ib, Ic, Id, and II) may be readily synthesized from commercially available starting materials using methods known in the art. Exemplary synthetic routes to produce compounds of formulae (I, Ia, Ib, Ic, Id, and II), are provided below in Preparations A-O and Schemes 1-5.

Scheme 1 below depicts general conditions for the synthesis of compounds of formula I.

Scheme 1:

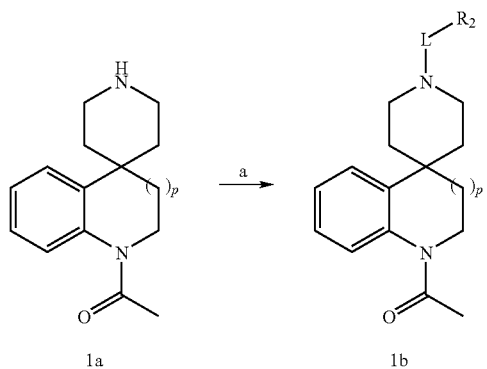

The reaction of amine 1a with an appropriate aldehyde or ketone under reductive amination conditions (step a), typically using $NaBH(OAc)_3$ in DCE/AcOH/TEA at room temperature, may be used to provide the desired compounds of formula 1b. For less reactive ketones, more forcing conditions may be used. For example, the treatment of the amine 1a and the ketone in a neat solution of $Ti(O^iPr)_4$, followed by treatment with $NaBH_4$ in MeOH, may be used to provide the desired compounds of formula I. See Abdel-Magid, A. F. et al., "Reductive Amination of Aldehydes and Ketones with Sodium Triacetoxyborohydride. Studies on Direct and Indirect Reductive Amination Procedures," J. Org. Chem., 61, pp. 3849-3862 (1996) and the references sited therein.

Alternatively, the spiroamine of type 1a may be alkylated with an alkyl halide in the presence of an appropriate base to provide the desired compounds of formula 1b. Typically, the amine 1a is reacted with an alkyl iodide, bromide, or chloride in the presence of an appropriate base to yield compounds of formula 1b. Bases may be organic such as triethylamine, or inorganic such as $Na_2CO_3$ or $Cs_2CO_3$. Typical reaction solvents include but are not limited to DMF, acetone, and acetonitrile.

Scheme 2 illustrates alternative conditions for the synthesis of compounds of formulae (I, Ia, Ib, Ic, Id, and II).

Scheme 2:

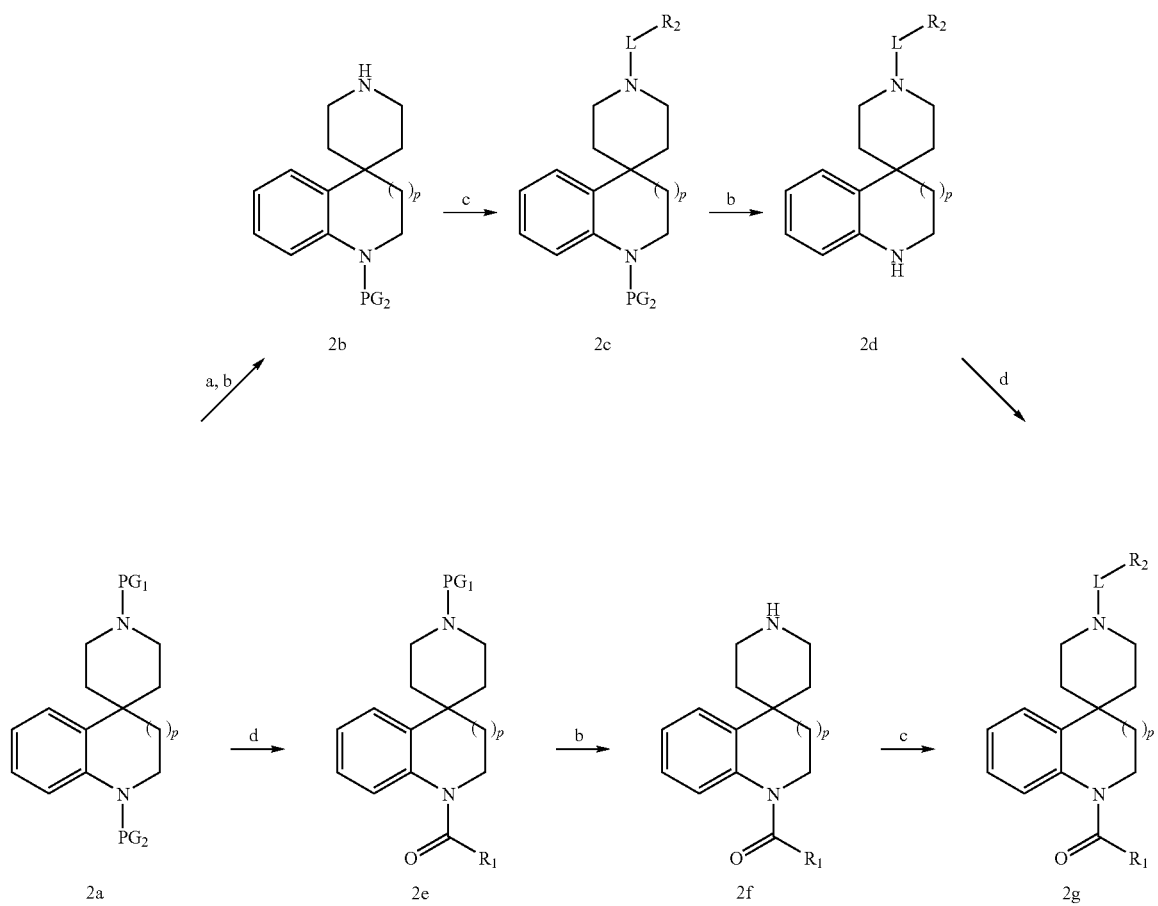

Amines of type 2a in Scheme 2 may be prepared from methods known in the art and by using procedures analogous to those found in the following references: WO 03/106457 "Spiroindolinepiperidine Derivatives"; Maligres, P. E., et al., Tetrahedron, 1997, 53, 10983-10992; Cheng, Y. and Chapman, K. T., Tet. Lett. 1997, 38, 1497-1500; US006013652A "Spiro-substituted azacyclics as neurokinin antagonists". Conditions: (a) amine protection orthoganol to $PG_1$; (b) amine deprotection of $PG_1$ (e.g. $PG_1$=Boc: TFA, $CH_2Cl_2$, −10° C.); (c) $NaBH(OAc)_3$, DCE, AcOH, TEA, appropriate ketone or aldehyde, or i. neat $Ti(OiPr)_4$, appropriate ketone, ii. $NaBH_4$, MeOH, or the appropriate alkyl halide, $Cs_2CO_3$, acetonitrile, heat; (d) $Q_2X$ ($Q_2$ may be, for example, H and aliphatic, X is halogen), $K_2CO_3$, DMF/THF, RT to 60° C.; or electrophile (e.g. $R_1COCl$, where $R_1$ is aliphatic or —$NR_6R'_6$, TEA, $CH_3CN$).

Scheme 3 illustrates alternative conditions as example for the synthesis of compounds of formula I in which the cycloaliphatic or heterocycloaliphatic ring $R_2$ contains or is substituted with a protected functionality that may be either be retained, deprotected and retained, or deprotected and further elaborated to produce additional compounds of formulae (I, Ia, Ib, Ic, Id, and II).

Scheme 3:

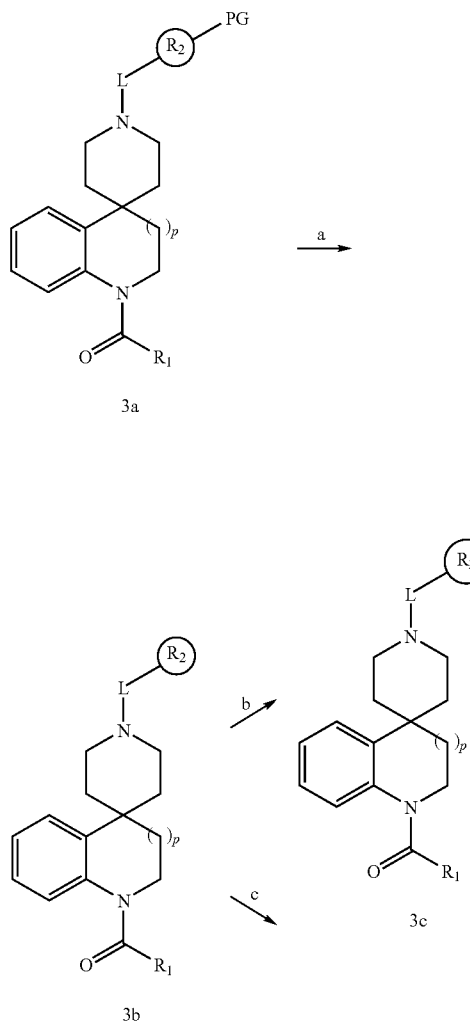

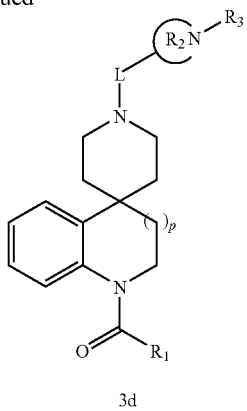

Compound 3a may be produced by methods disclosed above and by those known in the art. Compounds 3b through 3d may be produced from compound 3a using the following exemplary conditions: (a) PG=ketal: $AcOH/H_2O$, heat; or PG=Boc: TFA, $CH_2Cl_2$; (b) if ring $R_2$ is substituted by oxo, the compound of formula 3c may be further elaborated to the oxime: $NH_2$—O—$R_3$, pyridine; (c) if ring $R_2$ contains or is substituted by —NH— or —N($R_3$)—, it may be elaborated with an appropriate electrophile to produce 3d. For example, an acid halide or a dialkyl carbamoyl chloride in the presence of a base, such as triethylamine; or a haloaryl or haloheteroaryl compound under SNAr conditions such as $K_2CO_3$, acetonitrile and heat; a haloaryl or haloheteroaryl compound under Buchwald amination conditions such as a Pd catalyst for example $Pd_2(dba)_3$, a phosphine ligand and a suitable base for example NaOtBu.

Scheme 4 outlines the general preparation of the appropriate aldehydes from the corresponding ketone.

Scheme 4:

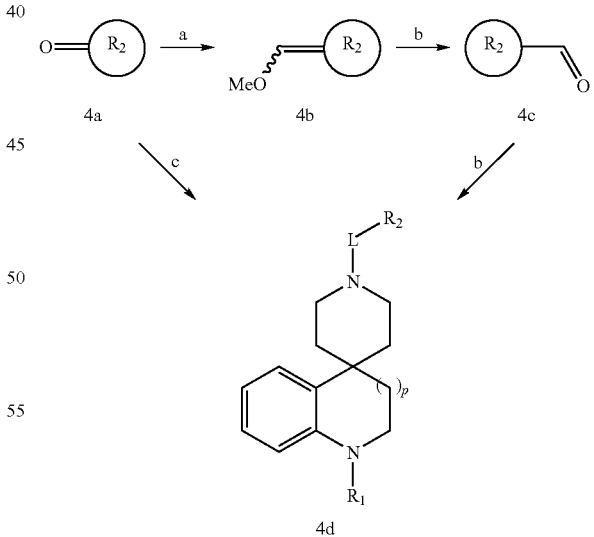

Ketone electrophiles of type 4a may be purchased commercially or produced by methods disclosed above and by those known in the art. Aldehydes of type 4c may be purchased commercially or produced from compounds of type 4a using the following conditions: (a) $Ph_3P^+CH_2OMeCl^-$, $NaN(SiMe_3)_2$; (b) aqueous HCl, $CH_3CN$. The following conditions may be used for the synthesis of compounds of formula I using ketones of type 4a and aldehydes of type 4c: (c) Spiro-amine of type 1a (see Scheme 1), NaBH(OAc)$_3$, DCE, AcOH, TEA, appropriate ketone or aldehyde; or i. neat Ti(O-iPr)$_4$, appropriate ketone; ii. NaBH$_4$, MeOH.

Compounds of the invention may be prepared by known methods or by using methods as described in Scheme 5.

Scheme 5:

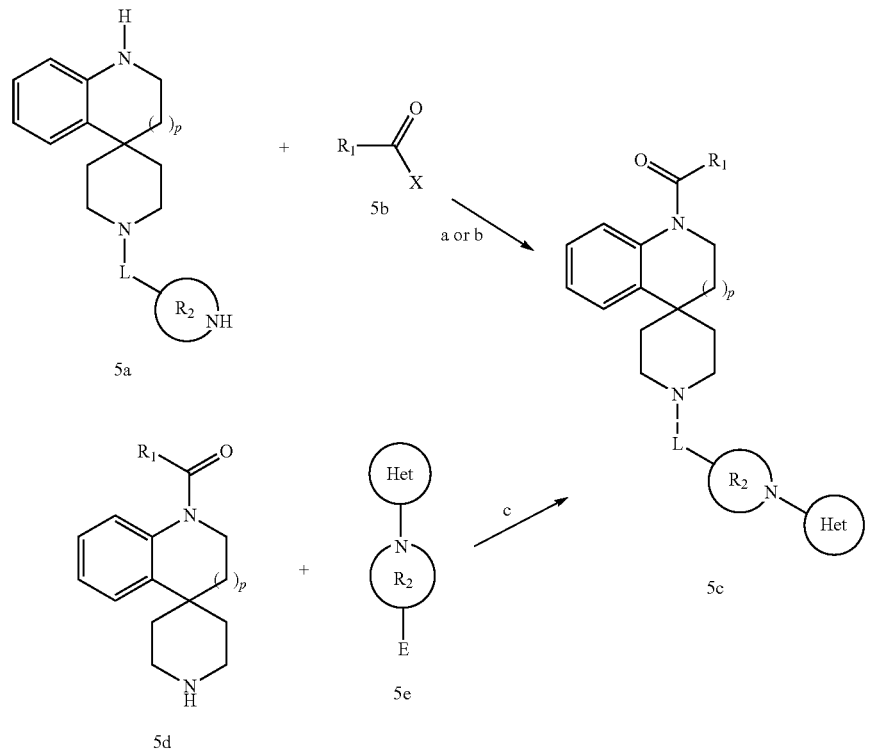

Referring to Scheme 5, compounds of formula 5d can be prepared from compounds of formula 5a using the following conditions: (a) reaction with an activated (aliphatic)carbonyl compound 5b such as, for example an acid halide or a dialkyl carbamoyl chloride in the presence of a base, such as triethylamine; (b) deprotection of the PG group, e.g., if PG=Boc: TFA, CH$_2$Cl$_2$, PG=Bn: H$_2$, Pd/C; (c) reaction with an electrophile of formula 5e wherein E represents a ketone in ring R$_2$ or an aldehyde attached to ring 2 using reductive amination conditions or alkylation conditions.

Compounds of formula 5e may be prepared by methods known in the art, for example, by reaction of an R$_2$ ketone or suitable protected precursor with a halogenated heteroaryl under S$_N$Ar conditions or Buchwald arylation conditions.

III. Formulations Administrations and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, Ia, Ib, Ic, Id, and II) are selective modulators of $M_1$, $M_2$ and $M_4$. More preferably, the compounds of formulae (I, Ia, Ib, Ic, Id, and II) are selective modulators of $M_1$ and/or $M_4$. Yet more preferably, certain compounds of formulae (I, Ia, Ib, Ic, Id, and II) are selective modulators of $M_1$. Or, preferably, certain compounds of formulae (I, Ia, Ib, Ic, Id, and II) are selective modulators of $M_4$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e., an agonist) or inhibits the activity of a muscarinic receptor.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, such as a human, including the step of administering to said mammal a composition comprising a compound of formulae I, Ia, Ib, Ic, or Id, or an embodiment thereof as set forth herein.

According to another embodiment, the present invention provides a method of treating a disease mediated by a muscarinic receptor including the step of administering to said mammal a composition comprising a compound of formulae (I, Ia, Ib, Ic, Id, and II), or other embodiments thereof as set forth above. Preferably, said disease is mediated by $M_1$, or said disease is mediated by $M_4$.

According to yet another embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, sudden infant death syndrome, Parkinson's disease, peripheral disorders such as reduction of intra ocular pressure in Glaucoma and treatment of dry eyes and dry mouth including Sjögren's Syndrome, wherein said method comprises the step of contacting said patient with a compound according to the present invention.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradycardia, gastric acid secretion, asthma, or GI disturbances.

According to a preferred embodiment, the present invention is useful for treating or reducing the severity of psychosis, Alzheimer's disease, pain, or Parkinson's disease.

All references cited within this document are incorporated herein by reference.

IV. Preparations and Examples

In order that the invention described herein may be more fully understood, the following examples are set forth. It should be understood that these examples are for illustrative purposes only and are not to be construed as limiting this invention in any manner.

Preparation A: Synthesis of N-(ethoxycarbonyl)-8-aza-bicyclo[3.2.1]octane-3-carbaldehyde (A3)

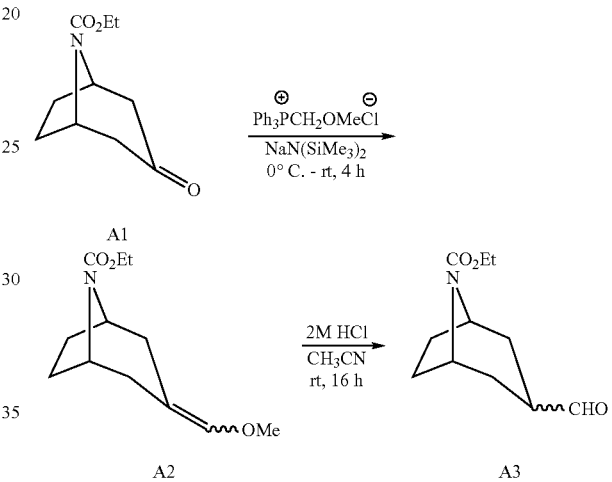

Sodium bis(trimethylsilyl)amide (6 mmol, 6 mL of 1 M solution in THF) was added to a suspension of 2.06 g (6.0 mmol) of methoxymethyltriphenylphosphonium chloride in 6 mL of THF at 0° C. under argon. After stirring at 0° C. for 15 min, the resulting dark red solution was added via syringe to a solution of 0.79 g (4.0 mmol) of N-(ethoxycarbonyl) tropinone (A1) in 8 mL of THF at 0° C. and then stirred at room temperature for 4 hr, and an orange color persisted. The reaction mixture was quenched by adding saturated aqueous NaCl (15 mL) and then extracted with ether (25 mL×3). The combined organic extracts were dried over $Na_2SO_4$. The solid residue obtained after solvent evaporation was loaded onto a short silica gel column (3.5 cm×4 cm) to remove the phosphorous impurities. The product was eluted with ether. After the solvent was evaporated, the product enol ether (A2) was obtained as a brown oil that was used in the next step without further purification.

The enol ether intermediate (A2) was dissolved in a solution of 12 mL of 2 N HCl and 20 mL of acetonitrile, and stirred at room temperature for 16 hrs. After removing the acetonitrile on a rotary evaporator, the aqueous solution was extracted with ether (25 mL×3). The combined organic extracts were washed with saturated aqueous $NaHCO_3$ (15 mL×2), saturated aqueous NaCl (15 mL) and then dried over $Na_2SO_4$. After the solution was evaporated to dryness, the residue was purified by chromatography ($SiO_2$, 10%-20% EtOAc in hexane as eluent). N-(ethoxycarbonyl)-8-aza-bicyclo[3.2.1]octane-3-carbaldehyde (A3) (0.65 g) was obtained as a colorless oil in an approximately 1:1 ratio of endo and exo isomers. ESI-MS m/z 212.1 (MH+); 1H NMR (300 MHz, CDCl3) δ 9.53 (s, 1H), 4.54 (br s, 1H), 4.38 (br s, 1H), 4.16 (m, 2H), 2.72 (m, 2H), 2.38 (s, 1H), 2.32 (s, 1H), 2.10 (m, 3H), 1.69 (m, 2H), 1.29 (m, 3H).

Preparation B: Synthesis of bicyclo[3.2.1]octane-2-carbaldehyde

Bicyclo[3.2.1]octane-2-carbaldehyde was prepared using an analogous procedure as for Preparation A from commercially available bicyclo[3.2.1]octan-2-one. The crude products were used in the next step without further purification.

Preparation C: Synthesis of 7-oxa-bicyclo[2.2.1]hept-5-ene-2-carbaldehyde (C3)

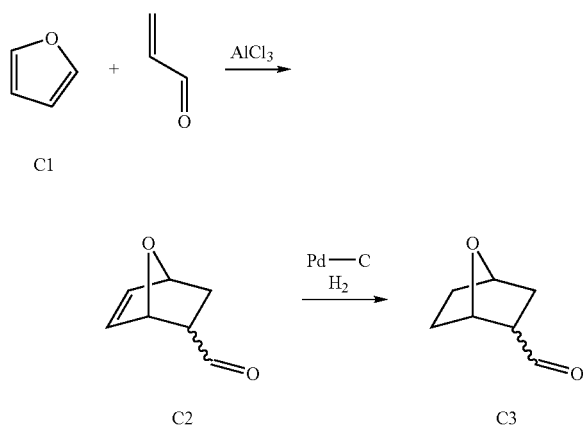

To a stirred solution of furan (C1) (15 mL, 200 mmol) and acrolein (6.7 mL, 100 mmol) in DCM (25 mL) was slowly added AlCl3 (666 mg, 5 mmol) under argon at −43° C. (dry ice/isopropanol bath). The reaction mixture was stirred at −43° C. under argon for 30 min and then quenched with saturated aqueous K2CO3 (50 mL). After the reaction mixture was gradually warmed to room temperature, it was extracted with ether (200 mL×5). The combined ether extracts were washed with saturated aqueous K2CO3 (200 mL×2) and saturated aqueous NaCl (200 mL×2), dried over MgSO4, filtered, and concentrated to give an oily crude product, 7-oxa-bicyclo[2.2.1]hept-5-ene-2-carbaldehyde (C2), which was used in the next step without further purification. See references Laszlo, P.; Lucchetti, J. Tetrahedron Lett. 1984, 25, 4387-4388. Moore, J. A., Partain, E. M. III. J. Org. Chem. 1983, 48, 1105-1106. Dauben, W. G.; Krabbenhoft, H. O. J. Am. Chem. Soc. 1976, 98, 1992-1993. Nelson, W. L.; Allen, D. R.; Vincenzi, F. F. J. Med. Chem. 1971, 14, 698-702.

To a stirred solution of crude product 7-oxa-bicyclo[2.2.1]hept-5-ene-2-carbaldehyde (C2) (2.6 g. 20 mmol) in 95% EtOH (200 mL) was added 10% Pd—C (0.25 g) at room temperature under argon. The mixture was shaken on a Parr hydrogenation apparatus for 4 hrs at room temperature under 30 psi of hydrogen. After the Pd catalyst was removed by filtration through a Celite pad, the Celite was washed with MeOH (15 mL×2), the combined extracts were concentrated under vacuum to crude 7-oxa-bicyclo[2.2.1]hept-5-ene-2-carbaldehyde (C3) as a pale yellow oil, which was used in the next step without further purification.

Preparation D: Synthesis of ethyl 4-formylpiperidine-1-carboxylate

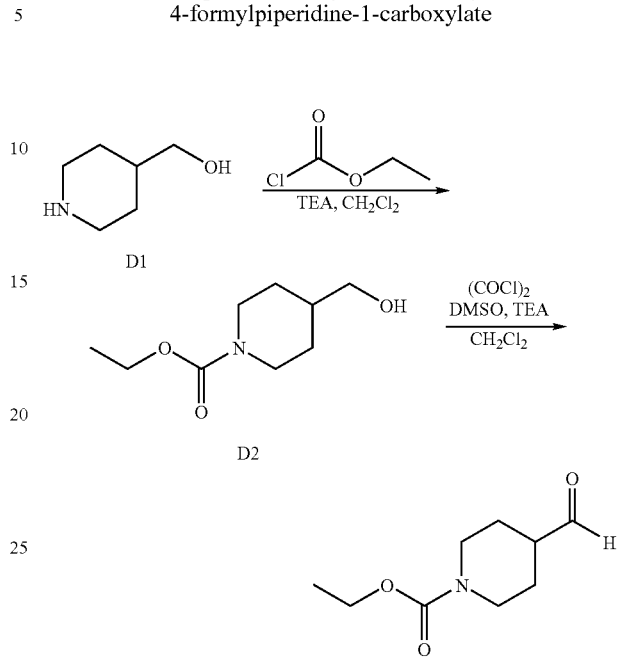

1.0 equivalent 4-piperidinemethanol (D1) (10.00 g, 86.8 mmol) was dissolved in dichloromethane (350 mL), cooled in an ice-H2O bath and treated dropwise with a solution of 1.05 equivalents ethyl chloroformate (9.89 g, 91.1 mmol) in dichloromethane (50 mL), followed by the dropwise addition of a solution of 1.0 equivalents triethylamine (8.78 g) in dichloromethane (50 mL). The reaction was stirred at ≈0° C. for 15 min, then at room temperature for 10 min. The reaction was diluted with dichloromethane (250 mL) and washed successively with (150 mL each) H2O, 0.1 N HCl (aq) (×2), saturated brine, then dried (Na2SO4) and filtered. The filtrate was concentrated in vacuo to give ethyl 4-(hydroxymethyl)-piperidine-1-carboxylate (D2) as a viscous, pale bluish-green oil. 1H-NMR (400 MHz, CDCl3) δ 4.15 (br m, 2H), 4.09 (q, J=7.1 Hz, 2H), 3.46 (d, J=6.4 Hz, 2H), 2.72 (br t, J=12.4 Hz, 2H), 2.07 (s, 1H), 1.70 (m, 2H), 1.63 (m, 1H), 1.23 (t, J=7.2 Hz, 3H), 1.12 (m, 2H); tR=1.56 min [10-99% CH3CN gradient over 5 mins with 0.1% TFA (aq)]; Theoretical (M+H)+ m/z for C9H17NO3=188.1; Found 188.0.

A solution of 1.2 equivalents oxalyl chloride (12.69 g, 0.10 mol) in dichloromethane (150 mL) was cooled to approximately −78° C. and treated dropwise, under nitrogen, with a solution of 2.4 equivalents anhydrous dimethylsulfoxide (15.63 g, 0.20 mol) in dichloromethane (50 mL). 15 minutes after the addition was complete, a solution of 1.0 equivalents ethyl 4-(hydroxymethyl)-piperidine-1-carboxylate (15.60 g, 83.3 mmol) in dichloromethane (50 mL) was added dropwise. 30 minutes after the addition was complete, a solution of 3.0 equivalents triethylamine (25.30 g, 0.25 mol) in dichloromethane (50 mL) was added dropwise and the reaction warmed to room temperature. The reaction was stirred at room temperature for 1 hr, then quenched with saturated sodium bicarbonate (500 mL). The layers were separated and the aqueous layer extracted once with dichloromethane (200 mL). The pooled organic layers were washed with H2O (3×100 mL), saturated sodium bicarbonate (1×100 mL) and saturated brine, then dried (Na$_2$SO$_4$) and filtered. The filtrate was concentrated in vacuo to afford 13.84 g ethyl 4-formylpiperidine-1-carboxylate (D3) as a viscous amber oil. $^1$H-NMR (400 MHz, CDCl$_3$) δ 9.64 (s, 1H), 4.10 (q, J=7.2 Hz, 2H), 4.00 (br m, 2H), 2.97 (m, 2H), 2.40 (m, 1H), 1.87 (br m, 2H), 1.54 (m, 2H), 1.23 (t, J=7.0 Hz, 3H).

Preparation E: Synthesis of ethyl 4-formyl-4-methylpiperidine-1-carboxylate (E6)

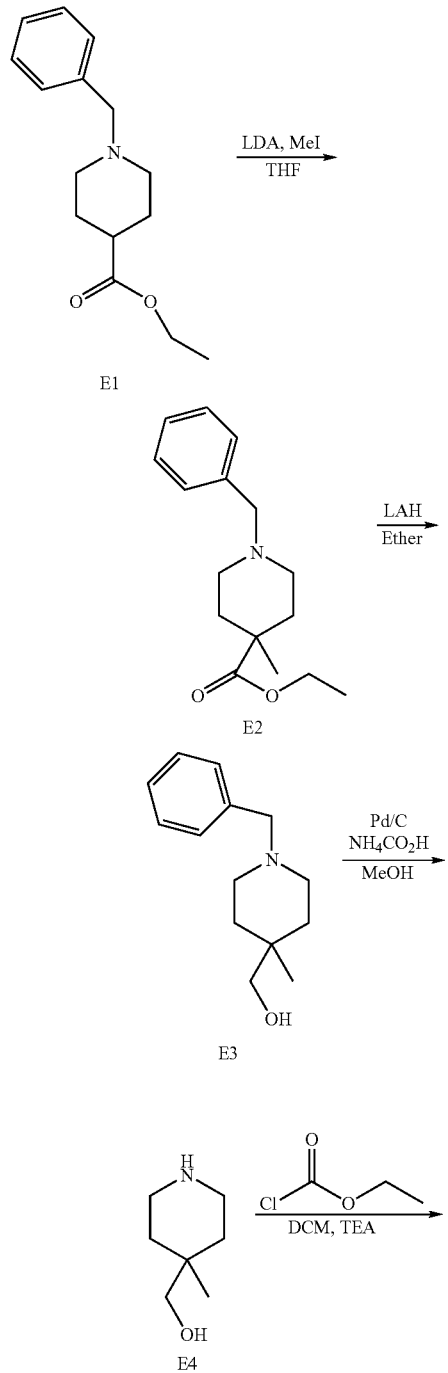

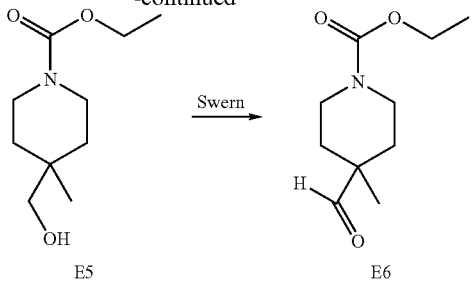

Diisopropylamine (3.14 mL; 22.23 mmol; 1.1 eq.) was dissolved in THF (60 mL) and cooled to −78° C. Butyl lithium (2.5 M in hexane; 8.89 mL; 22.23 mmol; 1.1 eq.) was then added and the solution was stirred for 30 minutes at −78° C. Ethyl 1-benzylpiperidine-4-carboxylate (E1) (5 g; 20.21 mmol; 1 eq.) was dissolved in THF (40 mL) and added to the LDA solution at −78° C. The solution was stirred at −78° C. for 30 min and iodomethane (1.32 mL; 21.22 mmol; 1.05 eq.) was added. The solution was slowly warmed to room temperature and stirred at room temperature for 1 hr. Water (100 mL) was then added to the reaction followed by EtOAc (50 mL). The layers were separated and the aqueous layer was extracted with EtOAc (2×50 mL). The combined organic layers were dried over Na$_2$SO$_4$, filtered, and concentrated under reduced pressure to afford the product (E2) as an oil. The product was analytically pure and used without further purification. LC/MS m/z (M+1) 262.0, Retention time 1.78 minutes; (10-99% CH$_3$CN—H$_2$O gradient with 0.03% TFA, 5 min). $^1$H NMR (400 MHz, CDCl$_3$) δ 7.24-7.14 (m, 5H), 4.08 (q, J=7.1 Hz, 2H), 3.40 (s, 2H), 2.60-2.57 (m, 2H), 2.08-2.02 (m, 4H), 1.47-1.40 (m, 2H), 1.17 (t, J 7.1. Hz, 3H), 1.10 (s, 3H).

1-Benzyl-4-methylpiperidine-4-carboxylate (E2) (5.0 g; 19.15 mmol) was dissolved in Et$_2$O (50 mL) and cooled to 0° C. LiAlH$_4$ (1.0 g; 26.3 mmol) was slowly added portion-wise to the solution. After the addition was complete, the solution was slowly warmed to room temperature and stirred for 1 hr. The solution was then cooled to 0° C. and slowly quenched with 1N NaOH (6 mL). The resultant white precipitates were filtered and washed with EtOAc (100 mL). The combined organic layers were concentrated under reduced pressure to provide the product (E3) as an oil, which was used without further purification. LC/MS m/z M+I 220.0, retention time 0.64 minutes; (10-99% CH$_3$CN—H$_2$O gradient with 0.03% TFA, 5 min). $^1$H NMR (400 MHz, CDCl$_3$) δ 7.25-7.16 (m, 5H), 3.46 (s, 2H), 3.30 (d, J=3.9 Hz, 2H), 2.51-2.46 (m, 2H), 2.26-2.20 (m, 2H), 1.52-1.45 (m, 3H), 1.30-1.25 (m, 2H), 0.87 (s, 3H).

(1-benzyl-4-methylpiperidin-4-yl)methanol (E3) (3.9 g; 17.8 mmol) was dissolved in MeOH (50 mL) and NH$_4$CO$_2$H (12.5 g; 178.0 mmol) was added. Pd/C (10% by weight, wet; 5.5 g) was then added and the system was flushed with nitrogen and then with hydrogen. The reaction was stirred at room temperature overnight (18 hrs) and then filtered through a pad of Celite. The solvent was removed under high vacuum to provide a solid that was a mixture of the amino alcohol and NH$_4$CO$_2$H. The crude product (E4) (2.4 g as a mixture with NH$_4$COOH) was used in the next step without further purification. LC/MS m/z (M+1) 130.0, retention time 0.35 min; (10-99% CH$_3$CN—H$_2$O gradient with 0.03% TFA, 5 min). $^1$H NMR (400 MHz, CDCl$_3$) δ 3.17 (s, 2H), 3.03-2.98 (m, 2H), 2.95-2.88 (m, 2H), 1.64-1.57 (m, 2H), 1.36-1.31 (m, 2H), 0.89 (s, 3H).

(4-methylpiperidin-4-yl)methanol (E4) (2.4 g, a mixture of the amino alcohol and NH₄CO₂H) was suspended in DCM (70 mL). Et₃N (5 mL; 37.2 mmol) was then added followed by the drop-wise addition of ethyl chloroformate (1.05 mL, 13 mmol, 1.4 eq.). After 1 hr at room temperature, 1N HCl (70 mL) was added and the layers were separated. The aqueous layer was extracted with DCM (70 mL) and the combined organic layers were dried over Na₂SO₄, filtered, and concentrated under high vacuum. The product obtained is an analytically pure oil (E5) and used without further purification. LC/MS m/z (M+1) 202.2, retention time 1.89 minutes; (10-99% CH₃CN—H₂O gradient with 0.03% TFA, 5 min). ¹H NMR (400 MHz, DMSO-d₆) δ 4.05 (q, J=7.1 Hz, 2H), 3.66 (dt, J=13.6, 4.7 Hz, 2H), 3.32 (s, 2H), 3.11 (t, J=5.2 Hz, 11H), 3.11 (dd, J=23.9, 3.5 Hz, 1H), 1.44-1.37 (m, 3H), 1.26-1.22 (m, 2H), 1.19 (t, J=7.1 Hz, 3H), 0.93 (s, 3H).

To a 100 mL round bottom flask was added DCM (30 mL) and oxalyl chloride (0.88 mL; 10.13 mmol). The solution was cooled to −78° C. and treated with DMSO (1.19 mL; 16.88 mmol). The solution was stirred at −78° C. for 20 minutes and then treated with ethyl 4-(hydroxymethyl)-4-methylpiperidine-1-carboxylate (E5) (1.7 g; 8.44 mmol, dissolved in 10 mL of DCM). The solution was stirred for 30 min at −78° C. and then treated with Et₃N (3.53 mL; 25.32 mmol). The solution was stirred at −78° C. for 20 min and then slowly warmed to room temperature and stirred at room temperature for an additional 2 hrs. The solution was then treated with saturated aqueous NaHCO₃ (50 mL), diluted with DCM (50 mL), and the layers were separated. The organic layer was washed with brine (50 mL), dried over Na₂SO₄, filtered, and concentrated under reduced pressure to afford the product (E6) as an oil, which was used without further purification. LC/MS m/z (M+1) 200.0, retention time 2.23 minutes; (10-99% CH₃CN—H₂O gradient with 0.03% TFA, 5 min). ¹H NMR (400 MHz, CDCl₃) δ 9.40 (s, 1H), 4.06 (q, J=7.1 Hz, 2H), 3.66 (dt, J=13.6, 4.7 Hz, 2H), 3.09 (dd, J=10.1, 3.5 Hz, 1H), 3.06 (dd, J=10.2, 3.4 Hz, 1H), 1.86 (dt, J=13.6, 4.4 Hz, 2H), 1.42-1.30 (m, 2H), 1.19 (t, J=7.1 Hz, 3H), 1.02 (s, 3H).

Preparation F: Synthesis of benzyl 4-oxotropane-N-carboxylate (F3)

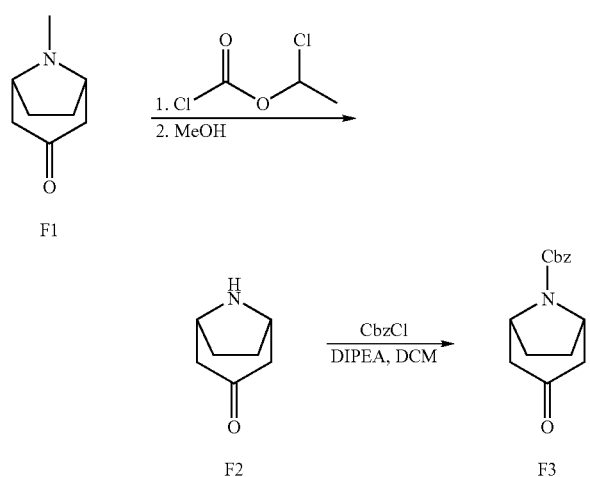

Tropinone (F1) (10.0 g; 71.84 mmol) was dissolved in DCE (60 mL) and treated drop-wise with 1-chloroethyl chloroformate ACE-Cl (14.5 mL; 19.11 g; 133.7 mmol). The reaction was allowed to stir at room temperature overnight and was then diluted with Et₂O (400 mL) and filtered. The filtrate was concentrated under reduced pressure to provide the crude chloroethyl carbamate. This compound was taken in MeOH (200 mL) and stirred at room temperature for 1 hr, then concentrated under reduced pressure (at 55° C.) to provide the crude desmethyltropinone (F2) as the HCl salt, a tan solid. The crude material was recrystallized from acetonitrile to furnish the pure product as a white crystalline solid. ¹H NMR (400 MHz, DMSO-d₆) δ 1.79 (dd, J=15.0, 6.9 Hz, 2H), 2.09 (m, 2H), 2.40 (d, J=16.7 Hz, 2H), 3.02 (dd, J=17.1, 4.3 Hz, 2H), 4.23 (s, 2H), 10.00 (br s, 2H) Des-methyl tropinone (F2) (5.10 g; 31.55 mmol) was dissolved in CH₂Cl₂ (50 mL) and treated with benzyl chloroformate (4.29 mL; 5.11 g; 29.98 mmol) DIPEA (16.48 mL; 12.23 g; 94.66 mmol) was added drop-wise (exothermic reaction). The resulting clear solution was allowed to stir at room temperature for 30 min and was subsequently diluted with 100 mL CH₂Cl₂. The organic phase was washed with 1 N HCl (2×100 mL), dried on Na₂SO₄ and concentrated to provide the crude product (F3). ¹H NMR (400 MHz, CDCl₃) δ 1.71 (dd, J=15.0, 7.2 Hz, 2H), 2.12 (m, 2H), 2.38 (d, J=15.9 Hz, 2H), 2.67 (m, 2H), 4.62 (s, 2H), 5.22 (s, 2H), 7.38 (m, 5H).

Preparation G: Synthesis of 5-chloro-3-methyl-1,2,4-thiadiazole (G2)

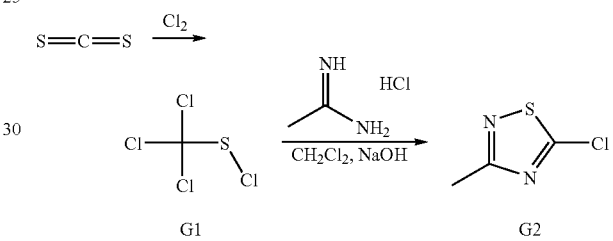

Dry chlorine gas was bubbled into CS₂ (1000 mL, containing about 1.0 g of iodine) at 5° C. for 48 hrs. The excess CS₂ was evaporated and the residue was fractionally distilled to give perchloromethyl mercaptan (G1) (bp 144-145° C./1 atm, 300 g, 10%). ¹³C-NMR (300 MHz, CDCl₃) δ 96.69 (1 C).

To a mixture of perchloromethyl mercaptan (G1) (60 g, 323 mmol) and acetamidine hydrochloride (30.6 g, 323 mmol) in dichloromethane (200 mL) was added dropwise a solution of NaOH (64.8 g in water (200 mL) at −5° C. The resulting mixture was stirred at −5° C. for 30 min and then allowed to warm to room temperature. The organic layer was separated and the aqueous phase was extracted with dichloromethane (30 mL×3). The combined organic layers were washed with water (50 mL×2) and brine (100 mL), dried over Na₂SO₄, and the solvent was removed. The residue was distilled under reduced pressure to give 5-chloro-3-methyl-1,2,4-thiadiazole (G2) (bp 70° C./0.85 Mpa, 18 g, 41.8%). ¹H-NMR (300 MHz, CDCl₃) δ 2.59 (s, 3H).

Preparation H: Synthesis of 1-(3-methyl-1,2,4-thiadiazol-5-yl)piperidin-4-one (H2)

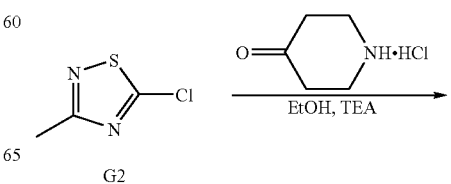

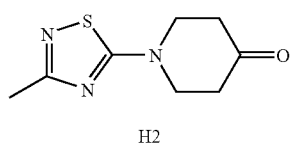

H2

To a mixture of piperidin-4-one HCl salt (4.08 g, 30 mmol) and Et₃N (20 mL, 78.6 mmol) in EtOH (50 mL) was added 5-chloro-3-methyl-1,2,4-thiadiazole (G2) (4.05 g, 30 mmol). The mixture was heated to reflux for 1.5 hours and then concentrated to dryness. The residue was dissolved in EtOAc. The solution was washed with water (30 mL×3) and brine (30 mL), dried over Na₂SO₄, and concentrated to dryness. The residue was recrystalled from ether to give 1-(3-methyl-1,2,4-thiadiazol-5-yl)piperidin-4-one (H2) (510 mg, 8.6%). ¹H-NMR (300 MHz, CDCl₃) δ 3.86 (t, J=6.3 Hz, 4H), 2.62 (t, J=6.3, Hz, 4H), 2.44 (s, 3H).

Preparation I: Synthesis of 1-(3-ethyl-1,2,4-thiadiazol-5-yl)piperidin-4-one (I2)

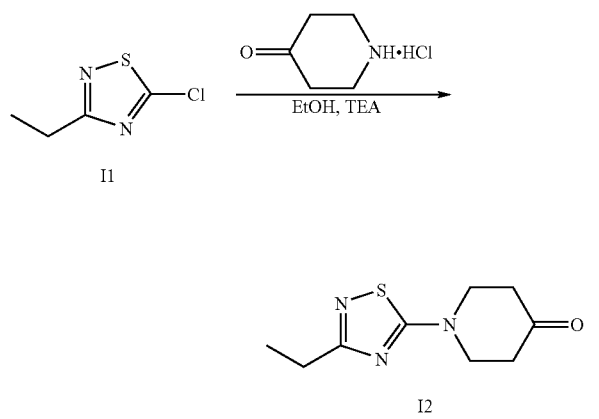

1-(3-ethyl-1,2,4-thiadiazol-5-yl)piperidin-4-one (I2) was made in a manner analogous to that found in Preparation B. ¹HNMR (400 MHz, CDCl₃) δ 3.95 (t, J=6.4 Hz, 4H), 2.84 (q, J=7.6 Hz, 2H), 2.68 (t, J=6.4, Hz, 4H), 1.36 (t, J=7.6 Hz, 3H).

Preparation J: Synthesis of 5-chloro-1,2,4-thiadiazole (J2)

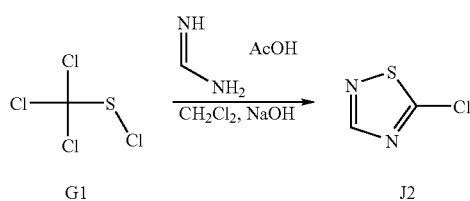

5-chloro-1,2,4-thiadiazole (J2) was made in a manner analogous to that found in Preparation A after distillation (bp 124° C./1 atm). ¹H-NMR (300 MHz, CDCl₃) δ 8.45 (s, 1H).

Preparation K: Synthesis of 1-(1,2,4-thiadiazol-5-yl)piperidin-4-one (K2)

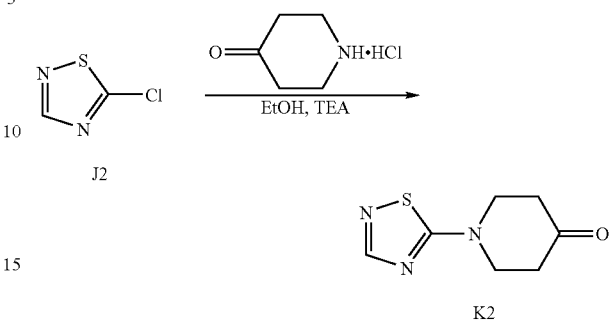

1-(1,2,4-thiadiazol-5-yl)piperidin-4-one (K2) was made in a manner analogous to that found in Preparation B. ¹H-NMR (300 MHz, CDCl₃) δ 8.00 (s, 1H), 3.92 (t, J=4.5 Hz, 4H), 2.65 (t, J=4.8 Hz, 4H).

Preparation L: Synthesis of 5-chloro-2,3-dimethylpyrazine (L3)

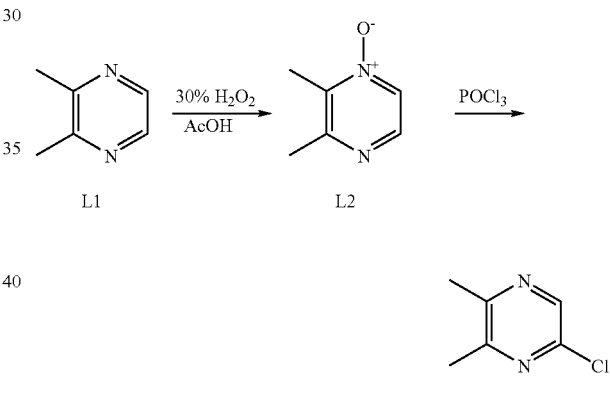

A mixture of 2,3-dimethylpyrazine (L1) (25 g, 0.23 mol) and 30% H₂O₂ (52.4 g, 0.46 mol) in acetic acid (74 mL) was stirred for two days at 35° C. The solvent was removed under vacuum. Water was added and the mixture evaporated again. The residue was basified with aqueous K₂CO₃ and extracted with EtOAc. The organic phases were dried over Na₂SO₄ and concentrated. The resulting solid combined from two batches was recrystallized from cyclohexane to give 2,3-dimethylpyrazine 1-oxide (L2) (27 g). ¹HNMR (CDCl₃, 300 MHz) δ 8.18 (d, J=3.9 Hz, 1H), 8.02 (d, J=4.2 Hz, 1H), 2.58 (s, 3H), 2.48 (s, 3H).

2,3-Dimethyl-pyrazine 1-oxide (L2) (25 g, 0.2 mol) was dissolved in POCl₃ (200 mL) under cooling. The mixture was gradually heated to reflux and stirred for 2 hrs. After cooling, the reaction mixture was poured onto ice, basified to pH 8 with a saturated KOH solution under cooling and extracted with EtOAc. The combined organics were dried over Na₂SO₄ and concentrated. The residue was purified by column (P. E./EtOAc 100:1-60:1) to obtain 5-chloro-2,3-dimethylpyrazine (L3). ¹HNMR (CDCl₃, 300 MHz) δ 8.31 (s, 1H), 2.53 (s, 6H). MS (ESI) m/e (M+H⁺) 143.2.

Preparation M: Synthesis of (S)-tert-butyl 3-formylpyrrolidine-1-carboxylate (M4)

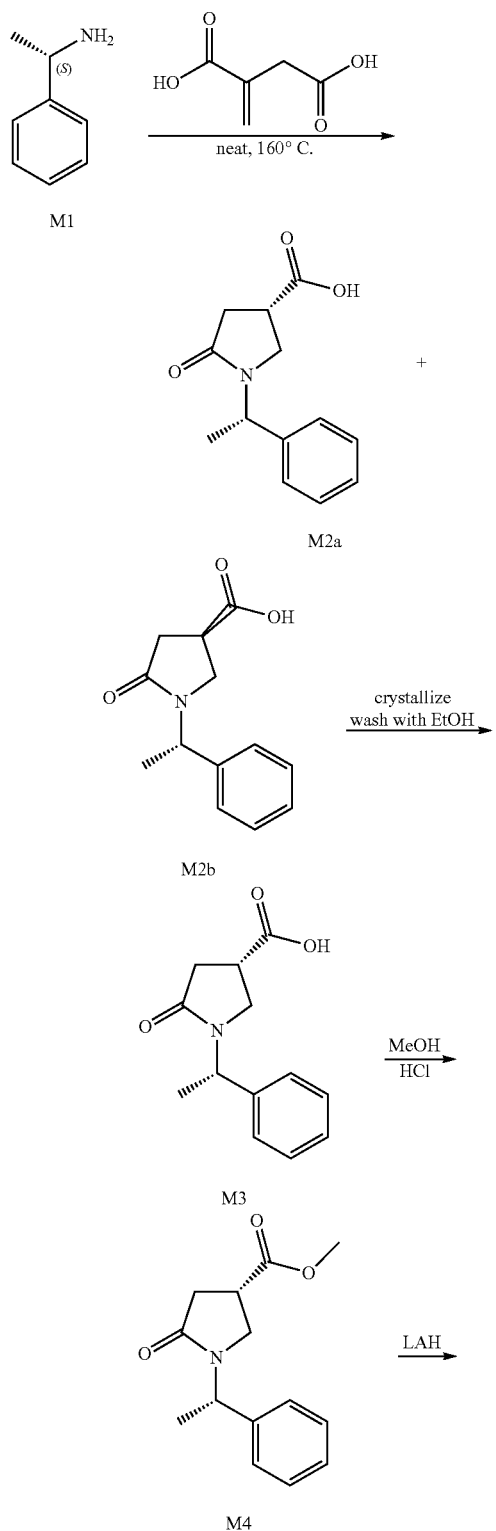

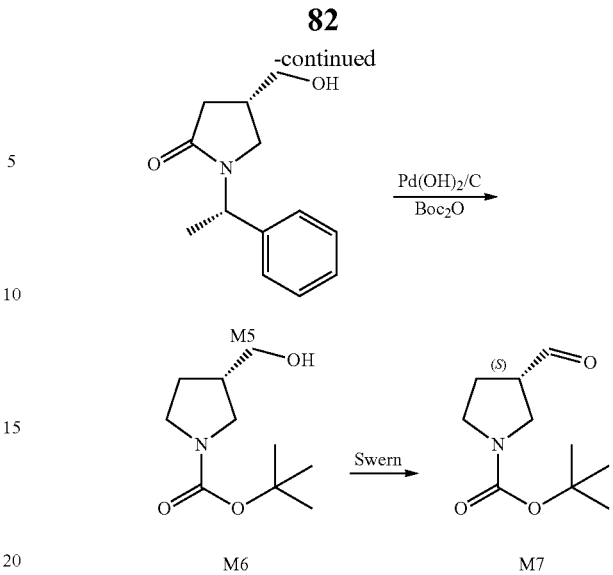

A mixture of itaconic acid (6.5 g, 50 mmol) and S-(−)-α-methylbenzylamine (M1) (6.05 g, 50 mmol) was heated at 160° C. (oil bath) for 4 hrs. Upon cooling, methanol (25 mL) was added and the resulting solid was collected by filtration. The solid was treated with ethanol (75 mL) and warmed using a steam bath until ≈40 mL solvent remained. After cooling to room temperature, the solid was collected and dried to afford (S)-5-oxo-1-((S)-1-phenylethyl)pyrrolidine-3-carboxylic acid (M3) as a white crystalline solid. ¹H NMR (300 MHz, DMSO-d₆) δ 12.6 (br s, 1H), 7.23-7.36 (m, 5H), 5.21 (q, J=6.9 Hz, 1H), 3.43-3.48 (m, 1H), 3.11-3.19 (m, 2H), 2.41-2.58 (m, 2H), 1.43 (d, J=6.9 Hz, 3H).

(S)-5-oxo-1-((S)-1-phenylethyl)pyrrolidine-3-carboxylic acid (M3) (1.16 g, 5 mmol) was treated with CH₃OH/HCl (10 mL, 1 M) for 3 h. The excess CH₃OH/HCl was removed under reduced pressure. The residue was basified with saturated aqueous NaHCO₃ to pH 8. The aqueous phase was extracted with ethyl acetate (50 mL×3). The combined organics were washed with brine, dried over Na₂SO₄ and evaporated under reduced pressure to give (S)-methyl 5-oxo-1-((S)-1-phenylethyl)pyrrolidine-3-carboxylate (M4), which was used directly in the next step. ¹H NMR (300 MHz, CDCl₃) δ 7.24-7.37 (m, 5H), 5.48 (q, J=7.2 Hz, 1H), 3.72 (s, 3H), 3.51-3.56 (m, 1H), 3.03-3.21 (m, 2H), 2.62-2.79 (m, 2H), 1.53 (d, J=7.2 Hz, 3H).

To a suspension of LAH (20 g, 0.526 mol) in dried THF (400 mL) was added dropwise a solution of (S)-methyl 5-oxo-1-((S)-1-phenylethyl)pyrrolidine-3-carboxylate (M4) (50 g, 0.202 mol) in dried THF (50 mL) at 0° C. The mixture was heated to reflux overnight. The reaction mixture was cooled to 0° C. and treated with water (20 mL) and aqueous NaOH (10%, 20 mL). The slurry formed was filtered off and washed with THF. The combined filtrate was evaporated to give compound ((S)-1-((S)-1-phenylethyl)pyrrolidin-3-yl)methanol (M5), which was used directly in the next step.

To a solution of ((S)-1-((S)-1-phenylethyl)pyrrolidin-3-yl)methanol (M5) (42.2 g, 0.194 mol) and (Boc)₂O (69.4 g, 0.292 mol) in methanol (300 mL) was added Pd(OH)₂/C (5 g). The resultant mixture was heated to 50° C. at 50 psi under H₂ and stirred overnight then cooled to room temperature. Pd(OH)₂/C was filtered and the filtrate was evaporated under reduced pressure to give a residue which was purified by column chromatography (P.E./EtOAc 5:1) to give (S)-tert-butyl 3-(hydroxymethyl)pyrrolidine-1-carboxylate (M6). ¹H NMR (300 MHz, CDCl₃) δ 3.60-3.63 (m, 2H), 3.29-3.52 (m, 3H), 3.07-3.13 (m, 1H), 2.37-2.42 (m, 1H), 1.94-1.98 (m, 1H), 1.62-1.70 (m, 1H), 1.45 (s, 9H).

To a solution of oxalyl chloride (22.17 g, 0.176 mol) in $CH_2Cl_2$ (200 mL) was added dropwise a solution of DMSO (20.59 g, 0.264 mol) in $CH_2Cl_2$ (50 mL) at −78° C. The mixture was stirred for 0.5 hrs at this temperature. A solution of (S)-tert-butyl 3-(hydroxymethyl)pyrrolidine-1-carboxylate (M6) (11.8 g, 58.7 mmol) in $CH_2Cl_2$ (50 mL) was added dropwise to the reaction mixture at −78° C. The mixture continued to stir for 1 hr at that temperature. $Et_3N$ (29.7 g, 0.294 mol) was added at −78° C. The resultant mixture was warmed to room temperature and stirred for 3 hrs. The mixture was poured into saturated aqueous $NaHCO_3$ and shaken. The organic layer was separated, washed twice with water, dried and evaporated to give a residue, which was purified by column chromatography (P.E./EtOAc 5:1) to give (S)-tert-butyl 3-formylpyrrolidine-1-carboxylate (M7). $^1H$ NMR ($CDCl_3$, 300 MHz): δ 9.68 (d, J=1.8 Hz, 1H), 3.67-3.68 (m, 1H), 3.51-3.55 (m, 1H), 3.35-3.40 (m, 2H), 2.99-3.04 (m, 1H), 2.04-2.18 (m, 2H), 1.46 (s, 9H).

Preparation N: Synthesis of (R)-tert-butyl 3-formylpyrrolidine-1-carboxylate (R)-tert-butyl 3-formylpyrrolidine-1-carboxylate was synthesized in a manner analogous to that of (S)-tert-butyl 3-formylpyrrolidine-1-carboxylate above by using the R-(+)-α-methyl benzylamine chiral auxiliary. Intermediates are characterized below:

(R)-5-oxo-1-((R)-1-phenylethyl)pyrrolidine-3-carboxylic acid: $^1H$ NMR (300 MHz, DMSO-$d_6$) δ 12.6 (br s, 1H), 7.25-7.36 (m, 5H), 5.21 (q, J=7.2 Hz, 1H), 3.43-3.51 (m, 1H), 3.08-3.19 (m, 2H), 2.48-2.58 (m, 2H), 1.43 (d, J=7.2 Hz, 3H).

(R)-methyl 5-oxo-1-((R)-1-phenylethyl)pyrrolidine-3-carboxylate: $^1H$ NMR (300 MHz, $CDCl_3$) δ 7.23-7.35 (m, 5H), 5.47 (q, J=7.2 Hz, 1H), 3.70 (s, 3H), 3.50-3.55 (m, 1H), 3.02-3.20 (m, 2H), 2.60-2.78 (m, 2H), 1.51 (d, J=7.2 Hz, 3H).

Preparation O: Synthesis of 1-benzylazocan-5-one (O3)

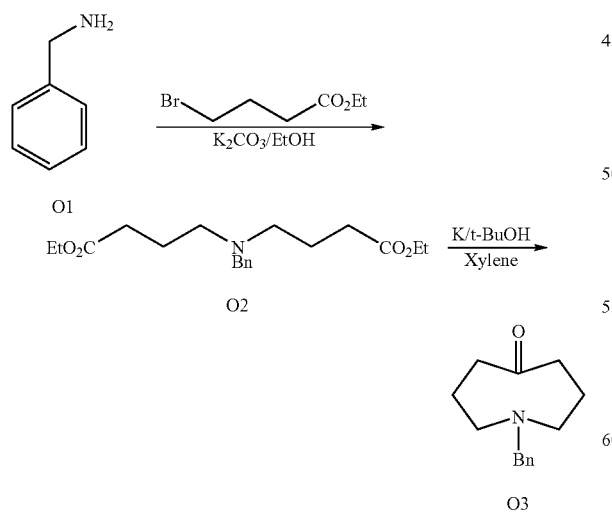

A mixture of benzylamine (O1) (83.7 g, 0.78 mol), 4-bromo-butyric acid ethyl ester (304.6 g, 1.56 mol) and $K_2CO_3$ (215.8 g, 1.56 mol) in anhydrous EtOH (970 mL) was refluxed overnight. The mixture was filtered, and the filtrate was concentrated and dissolved into dichloromethane, which was washed with water, dried over $Na_2SO_4$ and concentrated. The residue was purified by column chromatoghraphy (P.E.) to provide diethyl 4,4'-(benzylazanediyl)dibutanoate (O2) (123 g). $^1H$ NMR ($CDCl_3$, 400 MHz) δ 7.16-7.22 (m, 5H), 4.03 (q, J=7.2, 14.4 Hz, 4H), 3.47 (s, 2H), 2.36 (br s, 4H), 2.24 (t, J=7.6 Hz, 4H), 1.71 (br s, 4H), 1.17 (t, J=7.2 Hz, 6H).

To a stirred boiling slurry made from potassium (1.28 g, 32.8 mmol) and t-BuOH (2.43 g, 32.8 mmol) in xylene (182.5 mL) under $N_2$ was added diethyl 4,4'-(benzylazanediyl)dibutanoate (O2) (5 g, 14.9 mmol) over 5 hrs in xylene (37.25 mL). The mixture was stirred and heated at reflux for 1 hr. After being cooled, the reaction mixture was neutralized with 6N HCl (100 mL) and then was extracted with 6N HCl (3×50 mL). The combined acid solutions were filtered and the filtrate was heated under reflux for 1 hr. After cooling, the mixture was basified with concentrated KOH solution to pH 10 with cooling and extracted with dichloromethane. The combined organics were dried over $Na_2SO_4$ and concentrated to give a residue. Another 17 batches were done in parallel. The combined residue from 18 batches was purified together by column (P.E./EtOAc 5:1) to give 1-benzylazocan-5-one (O3). $^1H$ NMR ($CDCl_3$, 400 MHz) δ 7.30-7.33 (m, 2H), 7.21-7.25 (m, 3H), 3.56 (s, 2H), 2.55 (t, J=6.0, 4H), 2.24 (t, J=6.4 Hz, 4H), 1.86-1.91 (m, 4H).

Example 1 ethyl 4-(1'-acetyl-2',3'-dihydro-1'H-spiro[piperidine-4,4'-quinoline]-1-yl)piperidine-1-carboxylate (Compound No. 11)

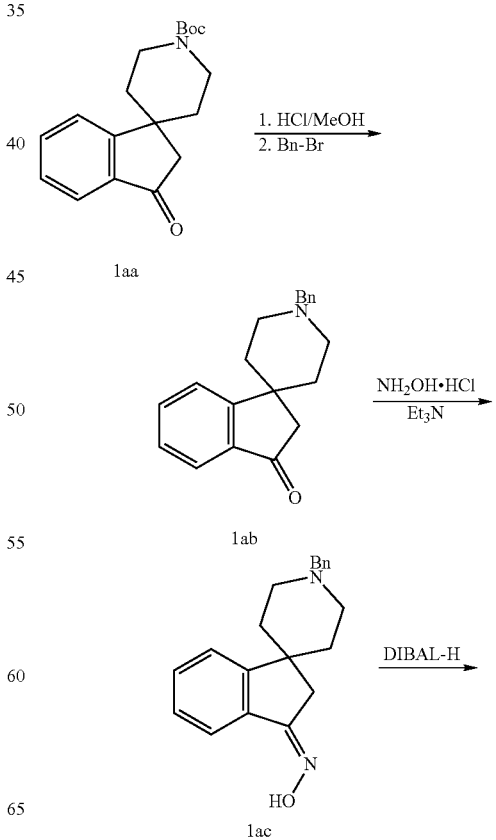

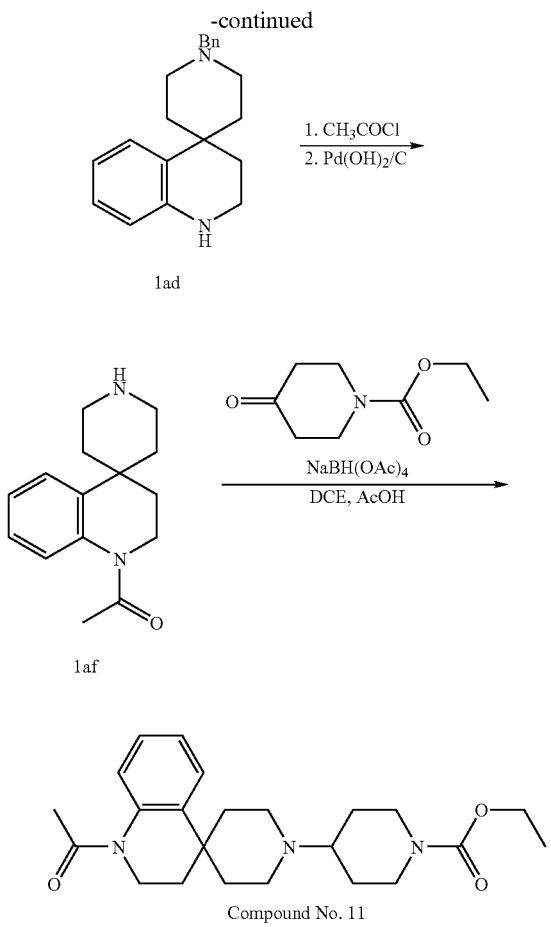

A mixture of tert-butyl 3-oxo-2,3-dihydrospiro[indene-1,4'-piperidine]-1'-carboxylate 1aa (40 g, 0.154 mol) in HCl/MeOH (700 mL, 2.5 M) was stirred over night at room temperature. The solvent was removed under reduced pressure to give 31 g of off-white solid. The solid (31 g) was dissolved in dry CH$_3$CN (400 mL). To this solution was added Et$_3$N (26.5 g, 0.262 mol). After the suspension was stirred for 10 min, benzyl bromide (24.6 g, 0.167 mol) was added dropwise at room temperature. After stirring for 2 hours at room temperature, the mixture was poured into ice-water and extracted with CH$_2$Cl$_2$. The organic layers were washed with brine and dried over Na$_2$SO$_4$. The solvent was evaporated under reduced pressure to give 1'-benzylspiro[indene-1,4'-piperidin]-3(2H)-one 1ab, which was used in the next step without further purification. $^1$H NMR (CD$_3$OD, 400 MHz) δ 7.32-7.42 (m, 3H), 6.98-7.15 (m, 6H), 3.40 (s, 2H), 2.75 (d, J=10.8 Hz, 2H), 2.34 (s, 2H), 1.94-2.11 (m, 2 μl), 1.84-1.92 (m, 2H), 1.26 (d, J=12.4 Hz, 2H).

To a solution of 1'-benzylspiro[indene-1,4'-piperidin]-3(2H)-one 1ab (38 g, 0.15 mol) in EtOH (300 mL), hydroxylamine hydrochloride (18 g, 0.30 mol) and sodium acetate (19.5 g, 0.275 mol) were added. The mixture was refluxed for 4 hours and the solvent removed under reduced pressure. The residue was diluted with 150 mL water and 100 mL CH$_2$Cl$_2$. After the mixture was stirred for 10 min, the resulting white solid was collected by filtration. The organic phase in the filtrate was separated and the aqueous layer was extracted with CH$_2$Cl$_2$. The combined organic layers were washed with brine and dried over Na$_2$SO$_4$. After evaporation of the solvent under reduced pressure, a yellow oil was obtained. The oil was crystallized from EtOAc to yield 1'-benzylspiro[indene-1,4'-piperidin]-3(2H)-one oxime 1ac as an off-white solid. $^1$H NMR (CD$_3$OD, 400 MHz) δ 7.64 (d, J=8.0 Hz, 1H), 7.55-7.57 (m, 2H), 7.38-7.50 (m, 5H), 7.29-7.33 (m, 1H), 4.25 (s, 2H), 3.41 (d, J=12.4 Hz, 2H), 3.08 (t, J=12.0 Hz, 2H), 2.95 (s, 2H), 2.20-2.28 (m, 2H), 1.68 (d, J=14.4 Hz, 2H).

To a solution of 1-benzylspiro[indene-1,4'-piperidin]-3(2H)-one oxime 1ac (6.4 g, 0.021 mol) in anhydrous CH$_2$Cl$_2$ (60 mL), DIBAL-H (108 mL, 1 M in toluene) was added dropwise at 0° C. The mixture was stirred for 3 hours at 0° C. The reaction was quenched by dilution with CH$_2$Cl$_2$ (30 mL), followed by successive treatment with NaF (16.2 g, 0.372 mol) and water (5.2 g, 0.288 mol) in ice-water bath. Vigorous stirring of resulting suspension was continued at 0° C. for 30 min. After filtration, the filter cake was washed with CH$_2$Cl$_2$. The solvent of the collected organic filtrates was removed under reduced pressure to give a brown oil. Another four batches on the same scale were done in parallel. The combined brown oil was purified by column chromatography on silica gel (CH$_2$Cl$_2$) to yield 1-benzyl-2',3'-dihydro-1'H-spiro[piperidine-4,4'-quinoline] 1ad (9.5 g, 31%). $^1$H NMR (CDCl$_3$, 400 MHz) δ 7.25-7.37 (m, 6H), 6.95-6.99 (m, 1H), 6.66-6.70 (m, 1H), 6.49 (dd, J=8.0 Hz, 1.6 Hz, 1H), 3.86 (s, 1H), 3.58 (s, 2H), 3.23 (t, J=5.6 Hz, 2H), 2.76 (d, J=11.6 Hz, 2H), 2.29 (t, J=12.0 Hz, 2H), 2.13-2.19 (m, 2H), 1.93 (t, J=5.6 Hz, 2H), 1.61 (d, J=11.6 Hz, 2H). MS (ESI) m/e (M+H$^+$) 293.2.

To a solution of 1-benzyl-2',3'-dihydro-1'H-spiro[piperidine-4,4'-quinoline] 1ad (4.5 g, 15.4 mmol) in dry CH$_2$Cl$_2$ (35 mL) was added NaHCO$_3$ (6.47 g, 77 mmol) at room temperature. Then acetyl chloride (1.2 g, 15.4 mmol) was added dropwise at ambient temperature. The mixture was stirred for 2 hours at room temperature. After filtration, the filtrate was washed with brine, dried over Na$_2$SO$_4$ and evaporated under reduced pressure to give a white solid, which was washed with ether and filtered to afford the pure product 1-(1-benzyl-2',3'-dihydro-1'H-spiro[piperidine-4,4'-quinoline]-1'-yl)ethanone 1ae (not shown). The solid (5.2 g, 15.6 mmol) was dissolved in MeOH (50 mL), then Pd(OH)$_2$/C (0.25 g) was added under Ar. The suspension was hydrogenated under H$_2$ (50 psi) at 50-55° C. overnight. After cooling and filtration, the filtrate was evaporated under reduced pressure to give 1-(2',3'-dihydro-1'H-spiro[piperidine-4,4'-quinoline]-1'-yl)ethanone 1ae (3.12 g, 83%, two steps). $^1$H NMR (CDCl$_3$, 300 MHz) δ 7.46-7.49 (m, 2H), 7.21-7.26 (m, 3H), 3.82 (t, J=5.7 Hz, 2H), 3.38 (d, J=12.9 Hz, 2H), 3.08-3.16 (m, 2H), 2.38-2.48 (m, 2H), 2.24 (s, 3H), 1.97 (t, J=6.0 Hz, 2H), 1.77 (d, J=14.7 Hz, 2H). MS (ESI) m/z (M+H$^+$) 245.2.

1-(2',3'-dihydro-1'H-spiro[piperidine-4,4'-quinoline]-1'-yl)ethanone 1af (500 mg, 2.05 mmol) and ethyl 4-oxopiperidine-1-carboxylate (420 mg, 2.46 mmol) were dissolved in 1,2-dichloroethane (10 mL) and glacial acetic acid (369 mg, 6.15 mmol) then treated with NaBH(OAc)$_3$ (869 mg, 4.1 mmol). The reaction was heated at 35° C. for 48 hours under nitrogen. The reaction was diluted with 1N HCL (100 mL) and washed with ethyl acetate (3×30 mL). The aqueous layer was basified with 5N NaOH and the product extracted into dichlromethane (3×50 mL). The organic layer was washed with brine, dried over Na$_2$SO$_4$, filtered and concentrated to yield the crude product as a colorless oil. The oil was chromatographed (silica, 3-10% MeOH/dichloromethane) to yield compound no. 11. LC/MS (10-99% CH$_3$CN/0.05% TFA gradient over 5 min): m/z 400.2, retention time 1.80 minutes.

Example 2 but-2-ynyl 4-(1'-(dimethylcarbamoyl)-2',3'-dihydro-1'H-spiro[piperidine-4,4'-quinoline]-1-yl)piperidine-1-carboxylate (Compound No. 5)

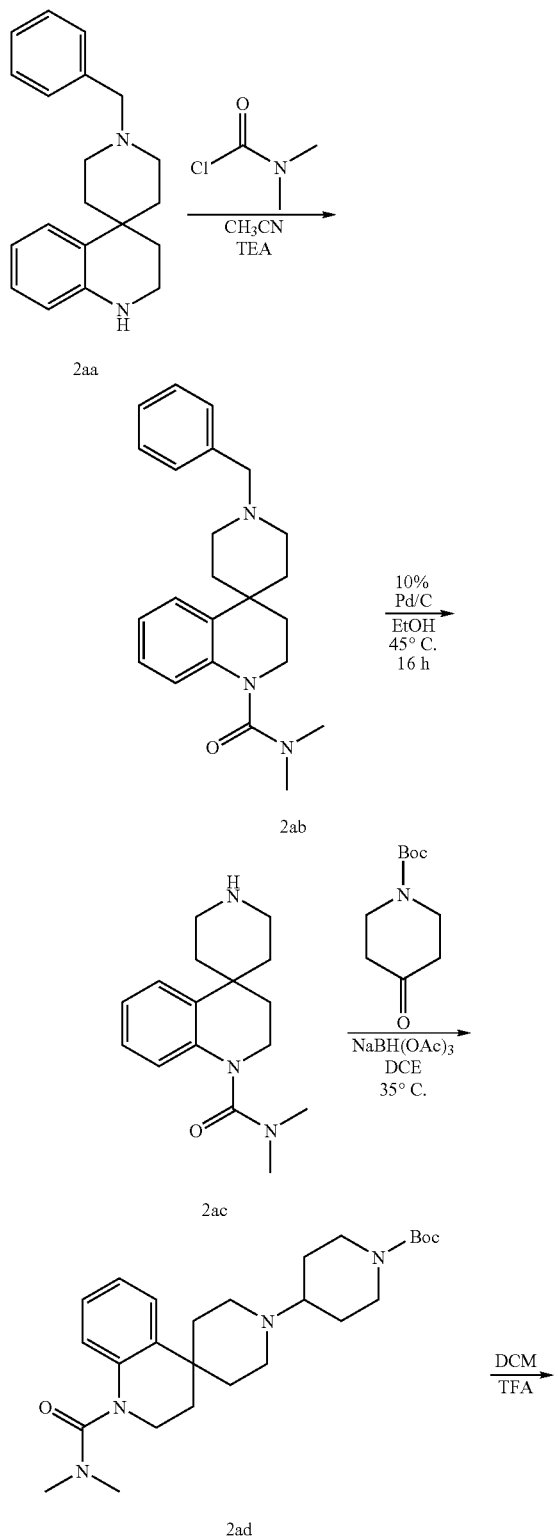

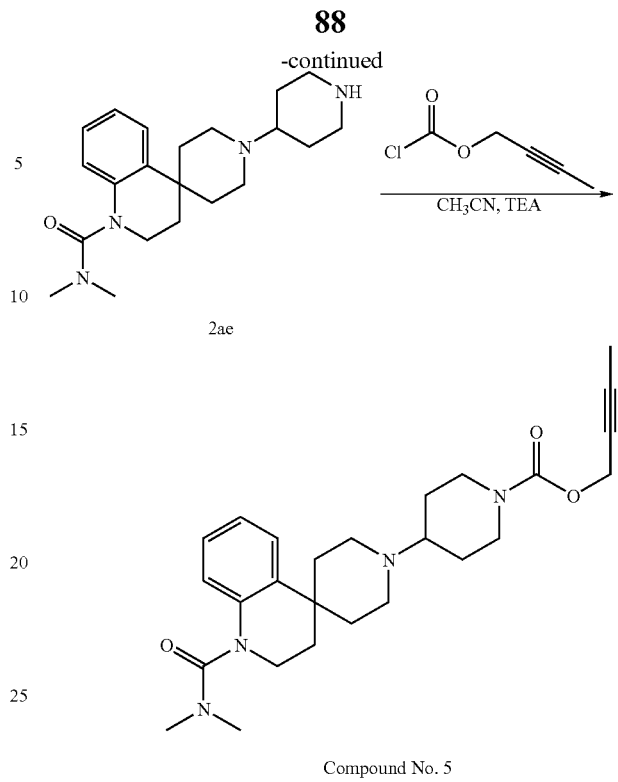

Compound No. 5

1-benzyl-2',3'-dihydro-1'H-spiro[piperidine-4,4'-quinoline]2aa was suspended in 30 mL acetonitrile and treated with 2 eq of dimethylcarbamoyl chloride, followed by the dropwise addition of triethylamine (2.38 mL, 17.1 mmol). The reaction was stirred at room temperature for 16 hours, then treated with 8 eq of dimethylcarbamoyl chloride heated to 45° C. for an additional 16 hours. The reaction was cooled, diluted with 100 mL 1.0 N HCL, and washed with ether (3×25 mL) and ethyl acetate (2×25 mL). The aqueous layer was basified and the product extracted into DCM. The organic layer was washed with brine, dried over $Na_2SO_4$, filtered and dried down. The crude product was filtered through a plug of silica (4-10% MeOH/DCM gradient) to yield crude 1-benzyl-N,N-dimethyl-2',3'-dihydro-1'H-spiro [piperidine-4,4'-quinoline]-1'-carboxamide 2ab. The product was carried on to the debenzylation step without further purification. LC/MS (10-99% $CH_3CN$/0.05% TFA gradient over 5 min): m/z 364.4, retention time 1.85 minutes.

The crude 1-benzyl-N,N-dimethyl-2',3'-dihydro-1'H-spiro [piperidine-4,4'-quinoline]-1'-carboxamide 2ab (3.1 g, 8.01 mmol) was dissolved in 30 mL absolute ethanol, flushed with nitrogen, and treated with 500 mg of 10% Pd/C. The flask was flushed with nitrogen then fitted with an H2 balloon. The rapidly stirring solution was heated to 45° C. overnight. The reaction was filtered through Celite and concentrated to yield N,N-dimethyl-2',3'-dihydro-1'H-spiro[piperidine-4,4'-quinoline]-1'-carboxamide 2ac as an amber oil. LC/MS (10-99% $CH_3CN$/0.05% TFA gradient over 5 min): m/z 274.2, retention time 1.39 minutes.

N,N-dimethyl-2',3'-dihydro-1'H-spiro[piperidine-4,4'-quinoline]-1'-carboxamide 2ac (800 mg, 2.93 mmol) and ethyl 4-oxopiperidine-1-carboxylate (875 mg, 4.40 mmol) were dissolved in 5.0 mL anhydrous dichloroethane and glacial acetic acid (351 mg, 5.86 mmol) then treated with NaBH(OAc)$_3$ (931 mg, 4.40 mmol). The flask was flushed with nitrogen and stirred for 18 hours at 35° C. The reaction was diluted with dichloromethane (50 mL) and washed with 1.0 N NaOH (50 mL), 50% saturated sodium bicarbonate (50 mL), and brine (100 mL). The organic phase was dried over $Na_2SO_4$, filtered and concentrated to yield 1.34 g of tert-butyl 4-(1'-(dimethylcarbamoyl)-2',3'-dihydro-1'H-spiro[piperidine-4,4'-quinoline]-1-yl)piperidine-1-carboxylate 2ad as a colorless oil. LC/MS (10-99% CH$_3$CN/0.05% TFA gradient over 5 min): m/z 457.4, retention time 2.00 minutes.

The tert-butyl 4-(1'-(dimethylcarbamoyl)-2',3'-dihydro-1'H-spiro[piperidine-4,4'-quinoline]-1-yl)piperidine-1-carboxylate 2ad (1.34 g, 2.93 mmol) was dissolved in 40 mL anhydrous dichloromethane and cooled to 0° C. The rapidly stirring solution was treated with TFA (20 mL) and allowed to come to room temperature over 2 hours. The reaction was diluted with ~20 mL acetonitrile and concentrated to an oil. The oil was brought up in 100 mL 1.0 N HCL and washed with diethyl ether (3×30 mL). The aqueous solution was then basified with 5 N NaOH and the product extracted into dichloromethane (3×50 mL). The organic layer was washed with brine (100 mL), dried over Na$_2$SO$_4$, filtered and concentrated to yield N,N-dimethyl-1-(piperidin-4-yl)-2',3'-dihydrospiro[piperidine-4,4'-quinoline]-1'-carboxamide 2ae as a colorless oil. LC/MS (10-99% CH$_3$CN/0.05% TFA gradient over 5 min): m/z 357.2, retention time 0.78 minutes. $^1$H NMR (400 MHz, DMSO-d$_6$) δ 7.35 (d, J=7.8 Hz, 1H), 7.06 (t, J=7.3 Hz, 1H), 6.90 (t, J=7.5 Hz, 1H), 6.75 (d, J=8.0 Hz, 1H), 3.40 (t, J=5.8 Hz, 2H), 3.13 (d, J=12.4 Hz, 2H), 2.77 (s, 6H), 2.71-2.61 (m, 5H), 2.42 (t, J=10.8 Hz, 3H), 1.92 (t, J=10.7 Hz, 2H), 1.86-1.78 (m, 5H), 1.58-1.45 (m, 4H).

N,N-dimethyl-1-(piperidin-4-yl)-2',3'-dihydrospiro[piperidine-4,4'-quinoline]-1'-carboxamide 2ae (35.7 mg, 0.1 mmol) was dissolved in acetonitrile (1 mL) and triethylamine (100 uL) and treated with but-2-ynyl carbonochloridate (26.5 mg, 0.2 mmol). The reaction was stirred for 1 hour, then diluted with methanol (0.5 mL) and purified by HPLC (2-99% CH$_3$CN gradient, 0.05% TFA) to yield compound no. 5. LC/MS (10-99% CH$_3$CN/0.05% TFA gradient over 5 min): m/z 453.2, retention time 2.31 minutes. $^1$H-NMR (CDCl$_3$, 400 MHz): δ 12.65 (br s, 1H), 7.69 (d, J=6.9 Hz, 1H), 7.13 (t, J=8.3 Hz, 1H), 7.02 (t, J=8.1 Hz, 1H), 6.83 (d, J=9.2 Hz, 1H), 4.66 (s, 2H), 4.38 (br s, 2H), 3.58 (m, 2H), 3.45 (m, 2H), 3.31 (m, 1H), 3.08 (m, 5H), 2.85 (s, 6H), 2.37 (m, 2H), 1.97 (m, 2H), 1.86 (t, J=2.3 Hz, 3H), 1.81 (m, 3H), 1.42 (t, J=7.3 Hz, 2H).

Example 3

N,N-dimethyl-1-(1-(6-methylpyrazin-2-yl)piperidin-4-yl)-2',31-dihydrospiro[piperidine-4,4'-quinoline]-1'-carboxamide (Compound No. 9)

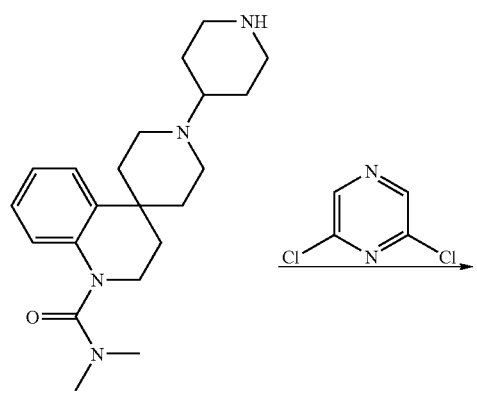

3aa

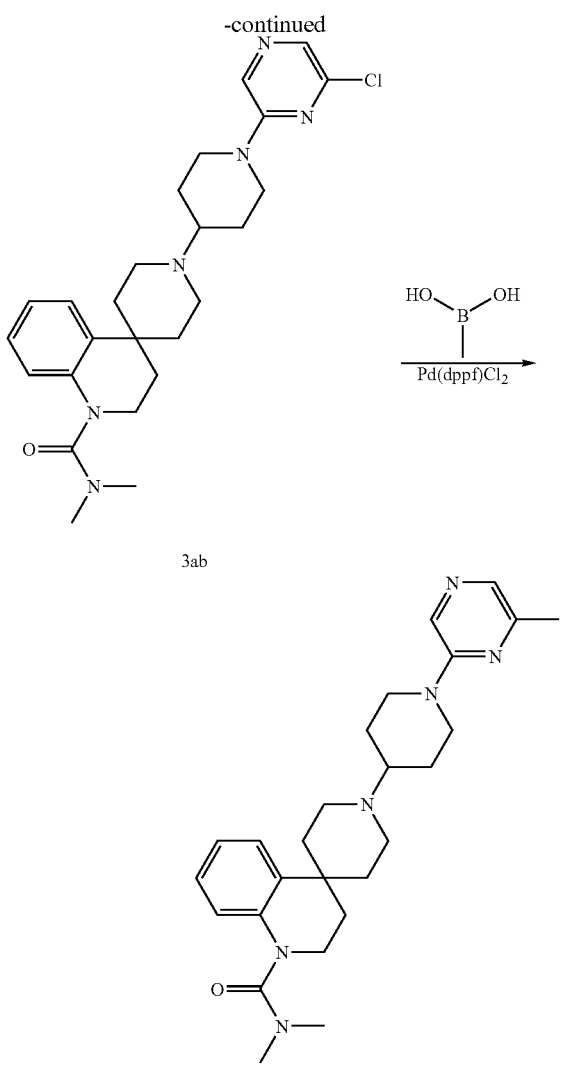

3ab

Compound No. 9

N,N-dimethyl-1-piperidin-4-yl)-2',3'-dihydrospiro[piperidine-4,4'-quinoline]-1'-carboxamide 3aa (620 mg, 1.75 mmol), potassium carbonate (725 mg, 5.25 mmol) and 2,6-dichloropyrazine (260 mg, 1.75 mmol) were dissolved in acetonitrile and heated with microwave irradiation to 150° C. for 20 min. The reaction was diluted with EtOAc (100 mL) and washed with 1.0 N NaOH (2×25 mL) and brine (1×25 mL). The organic layer was dried over Na$_2$SO$_4$, filtered and concentrated to yield crude 1-(1-(6-chloropyrazin-2-yl)piperidin-4-yl)-N,N-dimethyl-2',3'-dihydrospiro[piperidine-4,4'-quinoline]-1'-carboxamide 3ab. LC/MS (10-99% CH$_3$CN/0.05% TFA gradient over 5 min): m/z 469.3, retention time 2.45 minutes.

1-(1-(6-chloropyrazin-2-yl)piperidin-4-yl)-N,N-dimethyl-2',3'-dihydrospiro[piperidine-4,4'-quinoline]-1'-carboxamide 3ab (120 mg, 0.26 mmol), methyl boronic acid (46 mg, 0.78 mmol), and Pd(dppf)Cl$_2$ (12 mg) were dissolved in CH$_3$CN (2 mL) and 2 M Na$_2$CO$_3$ (3 mL) in a 20 mL microwave tube to form a biphasic mixture. The mixture was microwaved at 150° C. for 20 min. The crude reaction was purified by HPLC (2-99% CH$_3$CN gradient, 0.05% TFA) to yield compound no. 9. LC/MS (10-99% CH$_3$CN/0.05% TFA gradient over 5 min): m/z 449.2, retention time 1.75 minutes.

Example 4a 1-(1-(5,6-dimethylpyrazin-2-yl)piperidin-4-yl)-N,N-dimethyl-2',3'-dihydrospiro[piperidine-4,4'-quinoline]-1'-carboxamide (Compound No. 20)

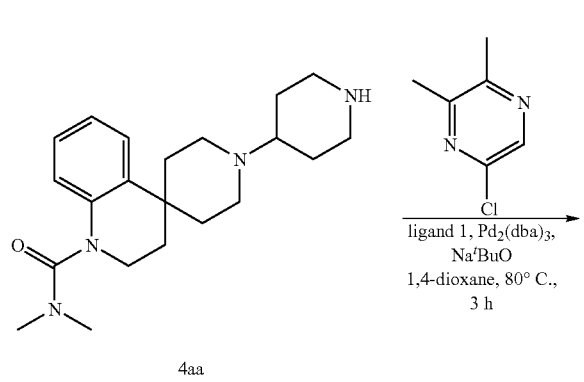

4aa

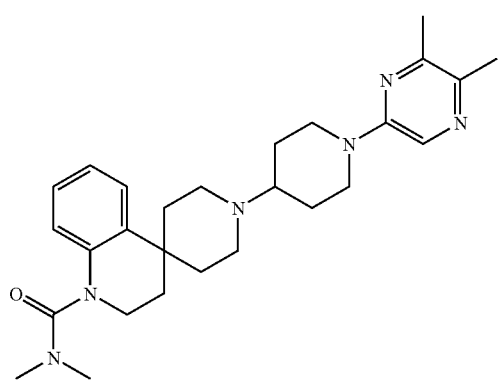

Compound No. 20

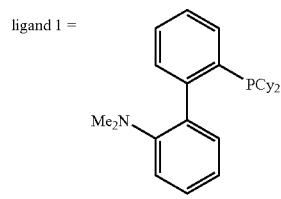

ligand 1 =

Pd$_2$(dba)$_3$-CHCl$_3$ (5 mg, 0.5 mol %), ligand 1 (8 mg, 2 mol %) and 1.4 eq sodium tert-butoxide (13 mg, 0.14 mmol) were weighed in air and transferred into a microwave tube, followed by dioxane (750 µL), 1.0 eq N,N-dimethyl-1-(piperidin-4-yl)-2'H-spiro[piperidine-4,4'-quinoline]-1'(3'H)-carboxamide (36 mg, 0.10 mmol) and 1.0 eq 5-chloro-2,3-dimethylpyrazine (14 mg). The tube was flushed with nitrogen, capped and stirred at 80° C. for 3 hours. The reaction was cooled to room temperature, diluted with methanol (500 µL), filtered (Whatman 0.45 µm PTFE) and subjected to reverse-phase HPLC purification (2-40% CH$_3$CN gradient [w/0.1% TFA (aq)] over t=10 minutes, 750 µL injected, 35 mL/min) to yield compound no. 20. LC/MS (10-99% CH$_3$CN/0.05% TFA gradient over 5 min): m/z 463.4, retention time 2.13 minutes.

Example 4b 5-fluoro-N,N-dimethyl-1'-(1-(pyrazin-2-yl)piperidin-4-yl)spiro[indoline-3,4'-piperidine]-1-carboxamide (Compound No. 52)

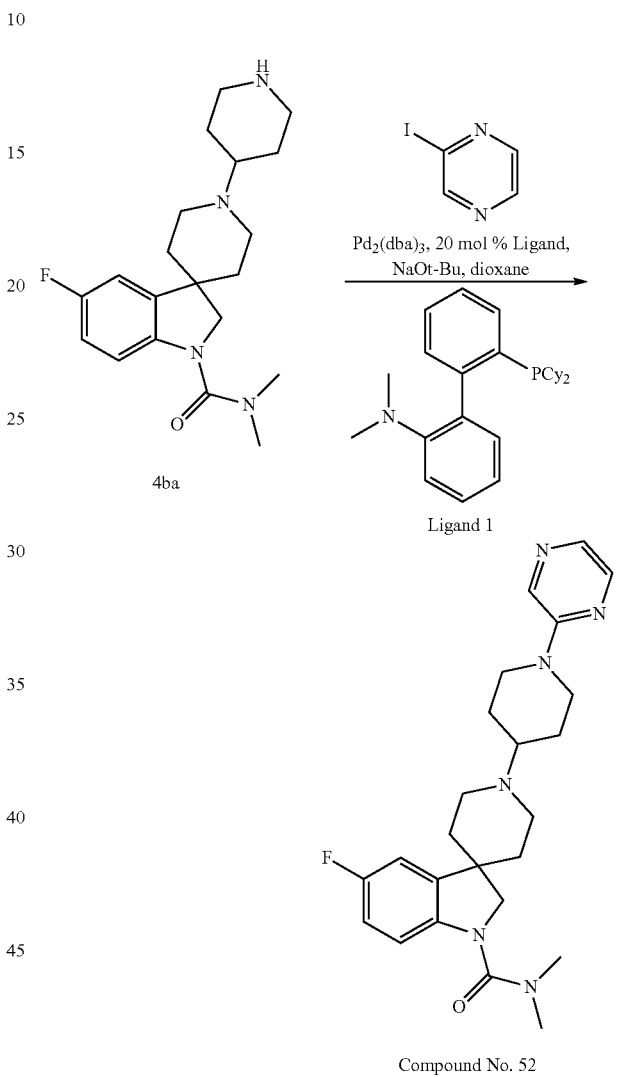

Pd$_2$(dba)$_3$ (0.5 mol %, 5.175 mg), ligand 12-(dicyclohexylphosphino)-2'-(N,N-dimethylamino) biphenyl (7.86 mg, 20 mol %), and sodium tert-butoxide (13.45 mg, 0.14 mmol) were weighed in air and transferred into a microwave tube. 5-fluoro-N,N-dimethyl-1'-(piperidin-4-yl)spiro[indoline-3,4'-piperidine]-1-carboxamide 4ba (36.0 mg, 0.1 mmol) and 2-iodo pyrazine (20.5 mg, 0.1 µmol) and 1 mL of dioxane were added. The tube was purged with N$_2$ and stirred at 80° C. for 16 hours. The reaction was diluted with methanol, filtered (Whatman 0.2 µm PTFE) and subjected to reverse-phase HPLC purification [2-50% CH$_3$CN gradient over 13 min with 0.1% TFA (aq), 35 mL/min, 1.5 mL injected] to provide compound no. 52. $^1$H NMR (400 MHz, MeOD) 8.63 (d, J=2.6 Hz, 1H), 8.52 (s, 1H), 7.92 (d, J=3.0 Hz, 1H), 7.28-7.23 (m, 2H), 7.03-6.98 (m, 2H), 4.75-7.72 (m, 2H), 3.93 (s, 2H), 3.70-3.78 (m, 3H), 3.33-3.18 (m, 4H), 3.00 (s, 6H), 2.42-2.35 (m, 4H), 2.05-1.92 (m, 4H). LC/MS (10-99% CH$_3$CN/0.05% TFA gradient over 5 min): m/z 421.1, retention time 2.03 minutes.

Example 5

N,N-dimethyl-1'-(8-(3-methyl-1,2,4-thiadiazol-5-yl)-8-azabicyclo[3.2.1]octan-3-yl)spiro[indoline-3,4'-piperidine]-1-carboxamide (Compound No. 65)

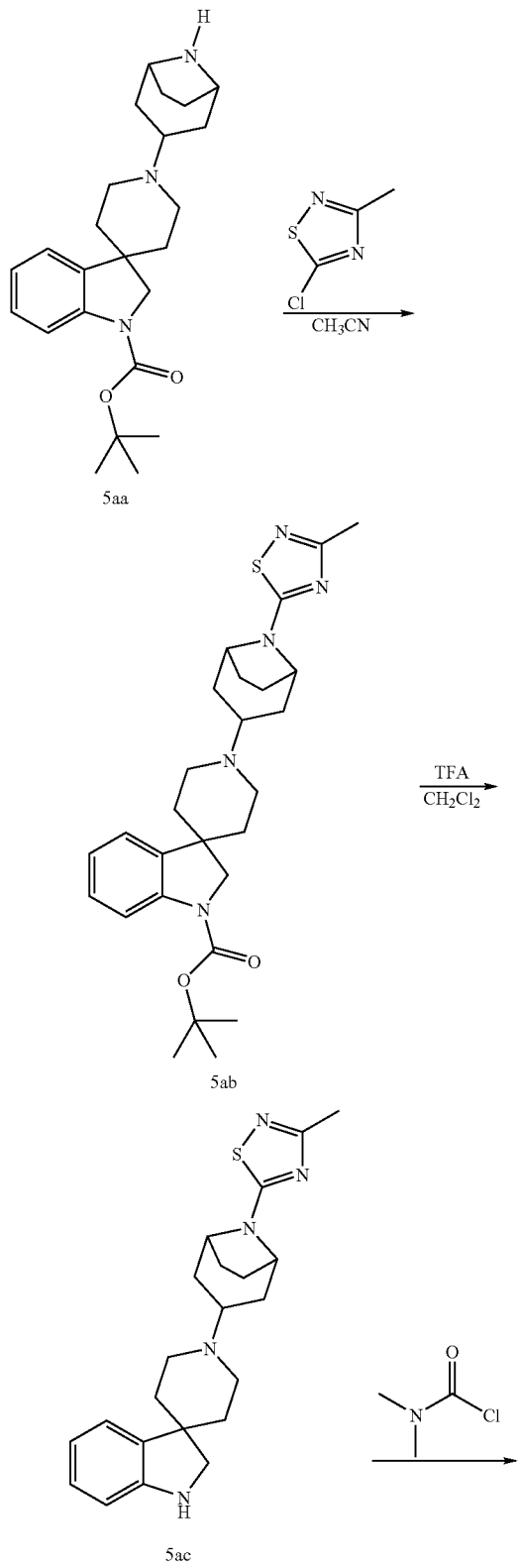

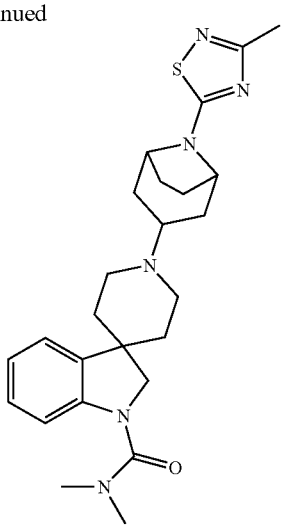

Compound No. 65 tert-butyl 1'-(8-azabicyclo[3.2.1]octan-3-yl)spiro[indoline-3,4'-piperidine]-1-carboxylate 5aa (350 mg, 0.88 mmol) was dissolved in 3 ml of acetonitrille in microwave tube. 3 eq (362.27 mg, 2.64 mmol) of $K_2CO_3$ was added followed by addition of 5 eq of 5-chloro-3-methyl-1,2,4-thiadiazole (592.2 mg, 4.4 mmol). The mixture was microwaved for 30 min at 160° C. The crude reaction was filtered to remove $K_2CO_3$ and the acetonitrille evaporated to provide crude product 5ab. LC/MS (10-99% $CH_3CN$/0.05% TFA gradient over 5 min): m/z 496.4, retention time 2.29 minutes.

Crude tert-butyl 1'-(8-(3-methyl-1,2,4-thiadiazol-5-yl)-8-azabicyclo[3.2.1]octan-3-yl)spiro[indoline-3,4'-piperidine]-1-carboxylate 5ab was dissolved in 1:1 mixture of $CH_2Cl_2$/TFA and stirred for 1 hour. The solvent was evaporated to give the crude 5ac TFA salt. The TFA salt 5ac was dissolved in 20 ml of $H_2O$ and stirred for 5 min. EtOAc 50 ml was added to the mixture and stirred for additional 15 min. The layers were separated, and the water layer was treated with 5 ml of 5N NaOH. The mixture was extracted with $CH_2Cl_2$ (3×50 mL). The organic layers were collected, combined, dried over $Na_2SO_4$, and concentrated to give crude free amine 5ac. Crude 5ac was purified by Preparative HPLC [2-50% $CH_3CN$ gradient over 13 mins with 0.1% TFA (aq), 35 mL/min, 1.5 mL injected] to give pure material as TFA salt. Pure TFA salt of 5ac was converted to free amine as described above, to give 0.7 mmol, 276 mg of 3-methyl-5-(3-(spiro[indoline-3,4'-piperidine]-1'-yl)-8-azabicyclo[3.2.1]octan-8-yl)-1,2,4-thiadiazole 5ac. LC/MS (10-99% $CH_3CN$/0.05% TFA gradient over 5 min): m/z 396.0, retention time 0.68 minutes.

5ac (276 mg, 0.7 mmol) was dissolved in 20 ml of $CH_2Cl_2$ and treated with 10 eq (747 mg, 6.98 mmol) of dimethylcarbamoyl chloride followed by addition of 3 eq (214 mg, 2.1 mmol) of triethylamine. The mixture was stirred under nitrogen for 16 hours to provide crude compound no. 65. The reaction mixture was concentrated, diluted with acetonitrille and purified by preparative HPLC[2-50% $CH_3CN$ gradient over 13 min with 0.1% TFA (aq), 35 mL/min, 1.5 mL injected] to give pure TFA salt of compound no. 65. $^1$H NMR (400 MHz, MeOD) 7.12-7.10 (m, 2H), 6.89-6.86 (m, 2H), 4.45 (s, 2H), 3.87 (bs, 1H), 3.80 (s, 2H), 3.60-3.79 (m, 2H), 3.09 (bs, 2H), 2.88-2.83 (m, 6H), 2.37 (s, 3H), 2.27-1.94 (m, 8H), 1.95-1.86 (m, 4H). LC/MS (RP—$C_{18}$, 10-99% $CH_3CN$/ 0.05% TFA gradient over 5 min): m/z 467.4, retention time 1.79 minutes.

Example 6

N,N-dimethyl-1'-(8-(pyrazin-2-yl)-8-azabicyclo[3.2.1]octan-3-yl)spiro[indoline-3,4'-piperidine]-1-carboxamide (Compound No. 103)

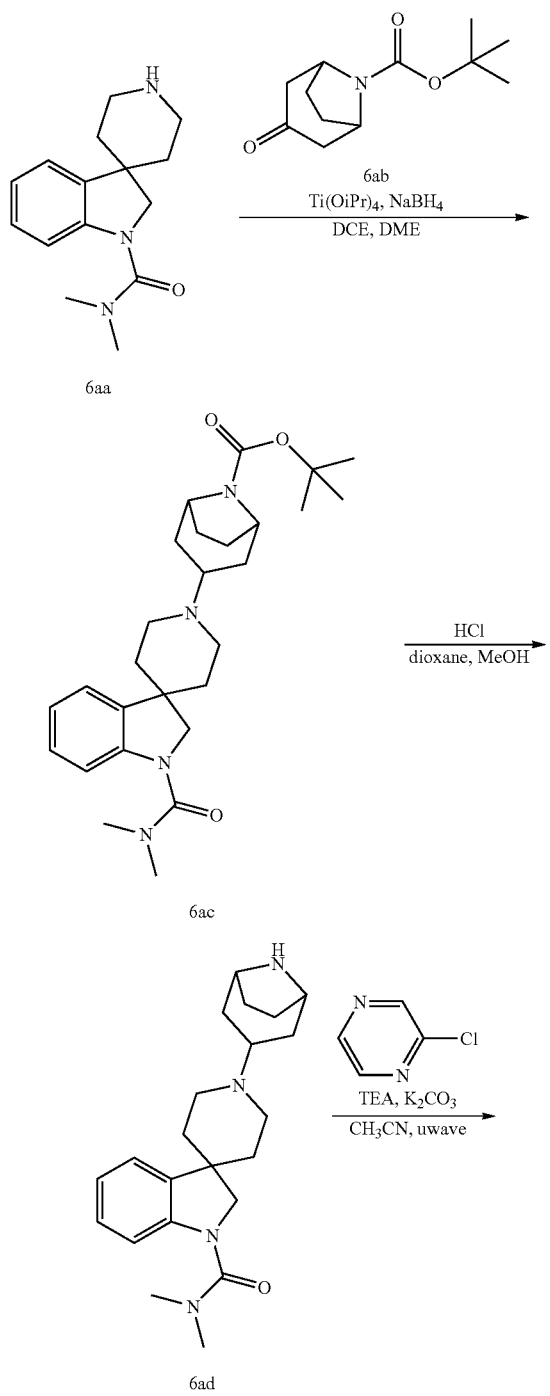

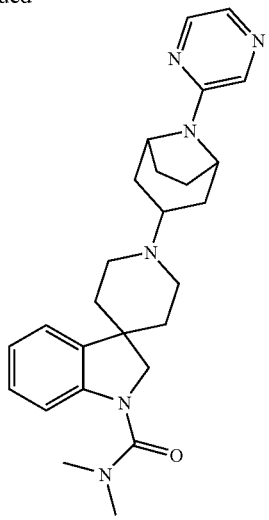

Compound No. 103

N,N-dimethylspiro[indoline-3,4'-piperidine]-1-carboxamide 6aa (500 mg, 1928 μmol) was suspended in a mixture of DCE (1.5 mL) and DME (1.5 mL) and treated with tert-butyl 3-oxo-8-azabicyclo[3.2.1]octane-8-carboxylate 6ab (651 mg, 2892 μmol) followed by titanium(IV) isopropoxide (2.260 ml, 7712 μmol). The tube was flushed with nitrogen, capped and allowed to stir under nitrogen at 35° C. for 50 hours. The reaction was quenched with MeOH (10 mL) and cooled to −40° C. Sodium triacetoxyborohydride (817 mg, 3856 μmol) was added portionwise, and the reaction was allowed to proceed at −40° C. until vigorous bubbling subsided, and the mixture was then slowly warmed up to room temperature and allowed to stir overnight. 1N NaOH (10 mL) was added, followed by acetone (50 mL) and the suspension was stirred for 2 hours to effect complete precipitation of the titanium salts. The suspension was filtered and the filter cake was rinsed with acetone (5×20 mL). The filtrate was concentrated to evaporate most of the organic solvents and the remaining aqueous phase diluted with 1N NaOH and extracted with dichloromethane (3×75 mL). The combined organic extracts were dried on $Na_2SO_4$ and concentrated to provide the crude product. To eliminate remaining traces of starting material, the crude product was dissolved in dichloromethane (20 mL) and treated with ethyl chloroformate (1 mL) and triethyl amine (1 mL). After 30 minutes, the solution was washed with 1N NaOH (30 mL). The aqueous layer was extracted with DCM (2×50 mL) and the combined organic extracts were dried on $Na_2SO_4$ and concentrated under reduced pressure. The free base was dissolved in diethyl ether (20 mL) and treated with excess 1N HCl in ether (5 mL). The resulting suspension was filtered under nitrogen, washed with diethyl ether (3×20 mL) and vacuum dried to provide tert-butyl 3-(1-(dimethylcarbamoyl)spiro[indoline-3,4'-piperidine]-1'-yl)-8-azabicyclo[3.2.1]octane-8-carboxylate hydrochloride 6ac as a white solid (90% purity by LC/MS). LC/MS m/z 469.4 [M+H]$^+$ retention time 2.12 minutes (10-99% $CH_3CN$—$H_2O$ gradient with 0.03% TFA, 5 min)

Tert-butyl 3-(1-(dimethylcarbamoyl)spiro[indoline-3,4'-piperidine]-1'-yl)-8-azabicyclo[3.2.1]octane-8-carboxylate hydrochloride 6ac (0.850 g, 1.683 mmol) was dissolved in MeOH (5 mL) followed by dioxane (40 mL) and treated with 4N HCl in dioxane (4.21 mL, 16.83 mmol). The reaction was allowed to stir overnight (complete conversion). The mixture was diluted with $Et_2O$ (150 mL) and filtered. The precipitate was washed with EtOAc (3×30 mL) and dried to provide 1'-(8-azabicyclo[3.2.1]octan-3-yl)-N,N-dimethylspiro[indoline-3,4'-piperidine]-1-carboxamide 6ad bis-hydrochloride as an off white solid (95% purity by LC/MS). This material was used for the next step without further purification. LC/MS m/z 369.0 [M+H]+ retention time 1.04 minutes (10-99% CH₃CN—H₂O gradient with 0.03% TFA, 5 min)

1'-(8-Azabicyclo[3.2.1]octan-3-yl)-N,N-dimethylspiro[indoline-3,4'-piperidine]-1-carboxamide (free base) 6ad (300 mg, 680 μmol) was dissolved in acetonitrile (3 mL) and treated with 2-chloropyrazine (312 mg, 2.7 mmol), followed by K₂CO₃ (564 mg, 4.08 mmol) and 400 uL of triethylamine. The reaction mixture was microwaved at 160° C. for 2×2 hours. The crude reaction mixture was concentrated under reduced pressure, then suspended in DCM (50 mL) and washed with 1N NaOH. The organic layer was dried on Na₂SO₄ and concentrated. The crude product was purified by silica gel chromatography on a 40 g column, using 1-5% dichloromethane-methanol gradient over 60 min. The pure fractions were concentrated and the free base was dissolved in diethyl ether (20 mL) and treated with excess 1N HCl in ether (5 mL). The resulting suspension was filtered under nitrogen, washed with diethyl ether (3×20 mL) and vacuum dried to provide the bis-hydrochloride of compound no. 103 as a yellow solid. LC/MS m/z 447.4 [M+H]+ retention time 1.80 minutes (10-99% CH₃CN—H₂O gradient with 0.03% TFA, 5 min). ¹H NMR (freebase) (400 MHz, CDCl₃) δ 8.07 (d, J=4.1 Hz, 2H), 7.81 (s, 1H), 7.16 (t, J=7.7 Hz, 2H), 6.91 (m, 2H), 4.65 (s, 2H), 3.74 (s, 2H), 2.94 (s, 6H), 2.90 (m, 2H), 2.20-2.12 (m, 4H), 1.93-1.60 (m, 11H).

Example 7 ethyl 4-(1-(dimethylcarbamoyl)spiro[indoline-3,4'-piperidine]-1'-yl)piperidine-1-carboxylate (Compound No. 39)

Compound no. 39 was synthesized using known methods and those described above. ¹H NMR (400 MHz; DMSO) δ 10.88 (s, 1H), 7.18 (td, J=7.7, 2.9 Hz, 1H), 7.12 (d, J=7.2 Hz, 1H), 6.94 (t, J=7.7 Hz, 2H), 4.12 (d, J=11.9 Hz, 2H), 4.05 (q, J=7.1 Hz, 2H), 3.81 (s, 2H), 3.45 (d, J=12.2 Hz, 2H), 3.16-3.05 (m, 2H), 2.87 (s, 6H), 2.83 (m, 2H), 2.39 (dd, J=10.7, 13.5 Hz, 2H), 2.16 (d, J=11.2 Hz, 2H), 1.82 (d, J=13.9 Hz, 2H), 1.66-1.57 (m, 2H), 1.20 (t, J=7.1 Hz, 3H).

Example 8 prop-2-ynyl 3-(1'-(dimethylcarbamoyl)-2',3'-dihydro-1'H-spiro[piperidine-4,4'-quinoline]-1-yl)-8-azabicyclo[3.2.1]octane-8-carboxylate (Compound No. 28)

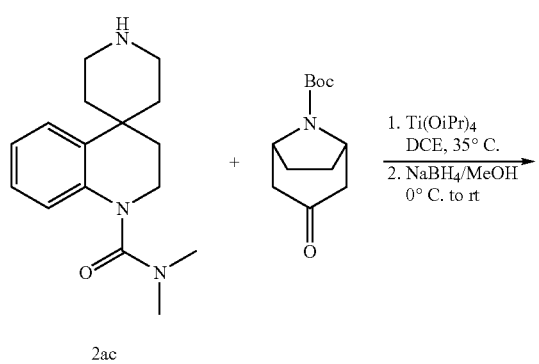

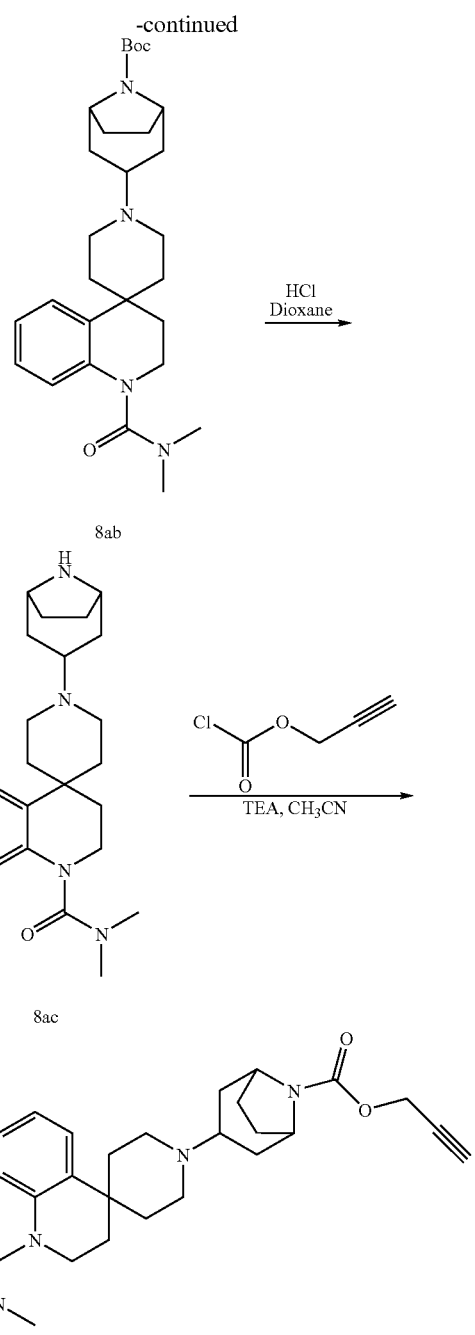

N,N-dimethyl-2',3'-dihydro-1'H-spiro[piperidine-4,4'-quinoline]-1'-carboxamide 2ac (400 mg, 1.47 mmol) and ethyl 4-oxopiperidine-1-carboxylate (658 mg, 2.92 mmol) were dissolved in 9.0 mL anhydrous dichloroethane. To this was then added titanium (IV) isopropoxide (1.25 g, 4.38 mmol). The flask was flushed with nitrogen and stirred for 60 hours at 35° C. The reaction was diluted with 30 mL of methanol and cooled to –20° C. whereupon NaBH₄ (110 mg, 2.92 mmol) was added portion-wise. After 20 min, the ice bath was removed and the suspension stirred at room temperature for 1 hour. To this was then added 1.0 N NaOH (25 mL) and after stirring for 20 min at room temperature, the suspension was filtered through a pad of Celite and the filter cake rinsed with methanol. The filtrate was evaporated and the remaining brown residue was extracted into 300 mL of dichloromethane. The solution was washed with 50% saturated sodium bicarbonate (50 mL), and brine (100 mL). The organic phase was dried over MgSO$_4$, filtered and concentrated to yield 875 mg of the crude product as a light brown foam. The material was purified on a small plug of silica eluting with a solution of 5% methanol (containing 5% NH$_4$OH) in dichloromethane to yield 388 mg. (55%) of pure tert-butyl 3-(1'-(dimethylcarbamoyl)-2',3'-dihydro-1'H-spiro [piperidine-4,4'-quinoline]-1-yl)-8-azabicyclo[3.2.1]octane-8-carboxylate 8ab (HCl salt) as a yellow solid. LC/MS (10-99% CH$_3$CN/0.05% TFA gradient over 5 min): m/z 483.4 [M+H]$^+$, retention time 2.34 minutes.

The intermediate 8ab (HCl Salt) (388 mg, 0.805 mmol) was dissolved in 5 mL of anhydrous dioxane and cooled to 0° C. The rapidly stirring solution was then treated with a solution of 4N HCl in dioxane and allowed to come to room temperature. The reaction was stirred overnight and then concentrated to yield 1-(8-azabicyclo[3.2.1]octane-3-yl)-N,N-dimethyl-2',3'-dihydro-1'H-spiro[piperidine-4,4'-quinoline]-1'-carboxamide 8ac as a light brown oil. LC/MS (10-99% CH$_3$CN/0.05% TFA gradient over 5 min): m/z 383.2 [M+H]$^+$, retention time 1.83 minutes.

The intermediate 8ac (HCl salt) (25 mg, 0.065 mmol) was dissolved in acetonitrile (2 mL) and triethylamine (100 uL) and treated with propargyl chloroformate (16 mg, 0.13 mmol). The reaction was stirred for 1 hour, then diluted with methanol (0.5 mL) and purified by HPLC (2-99% CH$_3$CN gradient, 0.05% TFA) to yield compound no. 28. LC/MS (10-99% CH$_3$CN/0.05% TFA gradient over 5 min): m/z 465.2 [M+H]$^+$, retention time 1.93 minutes.

Example 9

1-(8-(3-ethyl-1,2,4-thiadiazol-5-yl)-8-azabicyclo [3.2.1]octan-3-yl)-N,N-dimethyl-2',3'-dihydro-1' H-spiro[piperidine-4,4'-quinoline]-1'-carboxamide (Compound No. 32)

The intermediate 8ac (HCl salt) (25 mg, 0.065 mmol) was placed in a microwave vial and dissolved in acetonitrile (2 mL). The salt was then neutralized by addition of triethylamine (100 uL). To this solution was then added K$_2$CO$_3$ (16.4 mg, 0.118 mmol) followed by 5-chloro-3-ethyl-1,2,4-thiadiazole (132 mg, 0.89 mmol). The reaction was heated in the microwave at 160° C. for 20 min. After cooling to room temperature, the solution was diluted with methanol and filtered through a syringe filter. The filtrate was concentrated and the crude product purified by reverse phase HPLC (2-99% CH$_3$CN gradient, 0.05% TFA) to provide compound no. 32. LC/MS (10-99% CH$_3$CN/0.05% TFA gradient over 5 min): m/z 495.4 [M+H]$^+$, retention time 1.92 minutes.

Example 10

3-((S)-1'-((1R,2S,4S)-bicyclo[2.2.1]heptan-2-yl)-2,3-dihydrospiro[indene-1,4'-piperidine]-3-yl)-1,1-dimethylurea (Compound No. 119)

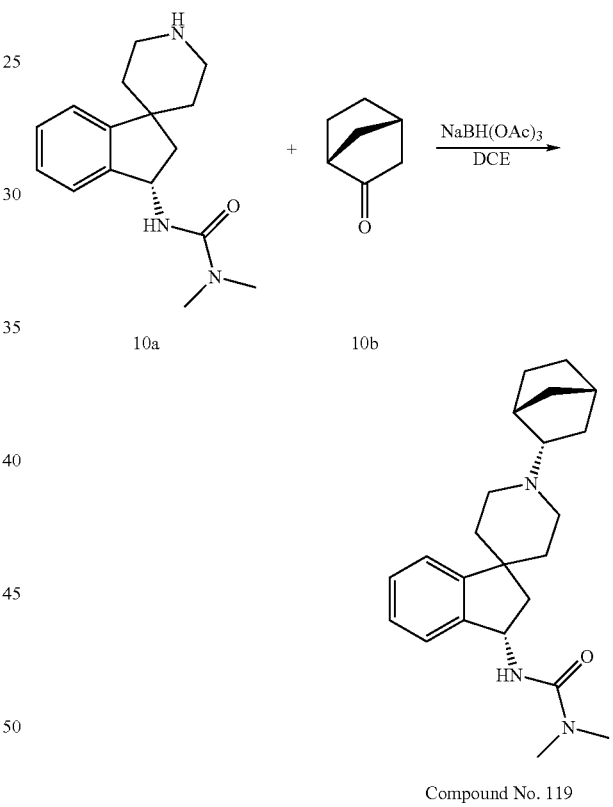

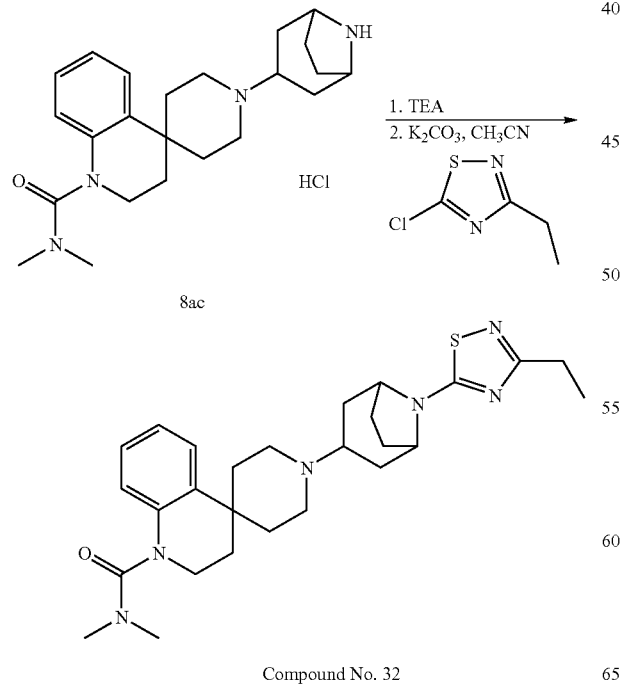

Compound No. 32

The starting material 10a (47.7 mg, 0.128 mmol, 1.0 eq) was suspended in DCE (1 mL) and treated with (−)-2-norcamphor 10b (21.1 mg, 0.192 mmol, 1.5 eq), followed by portion-wise addition of NaBH(OAc)$_3$ (81.4 mg, 0.384 mmol, 3.0 eq) and glacial acetic acid (3 eq). The reaction was stirred at room temperature for 72 h and was then quenched with MeOH (2 mL) and allowed to stir for another hour (until gas evolution stopped). The reaction mixture was then concentrated under reduced pressure and the residue obtained dissolved in DCM. The mixture was purified by normal-phase HPLC. The combined pure fractions were concentrated under reduced pressure to afford compound no 119 as a white foam. The pure fractions were dissolved in CH$_2$Cl$_2$ (1 mL)

and of ethyl acetate (5 mL). The mixture was stirred at 0° C. for 30 min and hydrochloric acid (1 eq) was added dropwise. The mixture was stirred in the ice bath for 30 min and then concentrated to dryness to provide the product as the HCl salt. $^1$H NMR (500 MHz, DMSO) 9.36 (s, 1H), 7.32-7.19 (m, 4H), 6.53 (d, J=8.3 Hz, 1H), 5.27 (q, J=8.3 Hz, 1H), 3.50-3.37 (m, 3H), 3.17 (d, J=12.3 Hz, 1H), 2.98 (d, J=10.0 Hz, 1H), 2.83 (s; 6H), 2.74-2.66 (m, 2H), 2.59 (s, 1H), 2.29 (s, 1H), 1.99 (d, J=10.6 Hz, 2H), 1.78-1.63 (m, 4H), 1.56-1.47 (m, 3H), 1.41 (d, J=11.7 Hz, 2H), 1.30 (d, J=9.1 Hz, 1H). LC/MS (10-90% over 3 min) m/z 368.2, retention time 1.5 minutes.

Example 11

Physical Characteristics of Compounds of Formulae (I, Ia, Ib, Ic, Id, and II)

Additional compounds having the structures shown in Table 1 were synthesized using known methods and those described above.

TABLE 2

Physical characteristics of compounds in Table 1.

| Cmd No. | LCMS Plus | LCMS RT |
|---|---|---|
| 1 | 426.5 | 2.09 |
| 2 | 415.5 | 2.00 |
| 3 | 429.5 | 2.12 |
| 4 | 439.5 | 2.13 |
| 5 | 453.5 | 2.24 |
| 6 | 455.5 | 2.09 |
| 7 | 469.5 | 2.21 |
| 8 | 435.3 | 2.05 |
| 9 | 449.5 | 1.85 |
| 10 | 386 | 1.51 |
| 11 | 400 | 1.69 |
| 12 | 410.2 | 1.68 |
| 13 | 424.2 | 1.81 |
| 14 | 438.2 | 1.97 |
| 15 | 426 | 1.62 |
| 16 | 440 | 1.75 |
| 17 | 406.4 | 1.58 |
| 18 | 456.2 | 1.92 |
| 19 | 454.2 | 1.69 |
| 20 | 463.4 | 2.13 |
| 21 | 441.4 | 2.16 |
| 22 | 454.2 | 2.08 |
| 23 | 412 | 2.12 |
| 24 | 411.2 | 2.01 |
| 25 | 425.2 | 2.01 |
| 26 | 441.4 | 1.8 |
| 27 | 455.4 | 1.92 |
| 28 | 465.2 | 1.93 |
| 29 | 479.2 | 2.04 |
| 30 | 461.4 | 1.78 |
| 31 | 481.2 | 1.77 |
| 32 | 495.4 | 1.92 |
| 33 | 357.2 | 0.76 |
| 34 | 328.2 | 0.51 |
| 35 | 440.4 | 2.07 |
| 36 | 454.2 | 2.09 |
| 37 | 425.2 | 2.05 |
| 38 | 401.2 | 1.64 |
| 39 | 415 | 1.74 |
| 40 | 429.2 | 1.88 |
| 41 | 429.4 | 1.91 |
| 42 | 451.4 | 1.84 |
| 43 | 445.6 | 1.68 |
| 44 | 439 | 1.84 |
| 45 | 427.2 | 1.74 |
| 46 | 441.4 | 1.87 |
| 47 | 455.4 | 1.98 |
| 48 | 455.2 | 1.87 |
| 49 | 477.4 | 1.93 |
| 50 | 471.6 | 1.79 |
| 51 | 465.2 | 1.95 |
| 52 | 421.2 | 1.70 |
| 53 | 441.4 | 1.76 |
| 54 | 401.2 | 2.02 |
| 55 | 429.4 | 2.17 |
| 56 | 429.4 | 2.27 |
| 57 | 451.2 | 2.21 |
| 58 | 445.4 | 2.07 |
| 59 | 401.2 | 2.03 |
| 60 | 415.4 | 2.14 |
| 61 | 429.4 | 2.29 |
| 62 | 429.4 | 2.26 |
| 63 | 451.2 | 2.22 |
| 64 | 445.4 | 2.09 |
| 65 | 467.2 | 2.14 |
| 66 | 481.2 | 2.27 |
| 67 | 415.4 | 2.03 |
| 68 | 429.4 | 2.14 |
| 69 | 443.4 | 2.27 |
| 70 | 443.4 | 2.26 |
| 71 | 465.4 | 2.22 |
| 72 | 459.4 | 2.07 |
| 73 | 471.2 | 2.05 |
| 74 | 440.4 | 1.86 |
| 75 | 427.2 | 1.72 |
| 76 | 455.4 | 1.88 |
| 77 | 455 | 2 |
| 78 | 471.4 | 1.98 |
| 79 | 435.2 | 1.71 |
| 80 | 429.5 | 2.15 |
| 81 | 429.4 | 2.13 |
| 82 | 435.2 | 2.04 |
| 83 | 441.5 | 1.90 |
| 84 | 455.5 | 2.00 |
| 85 | 441.5 | 1.93 |
| 86 | 455.5 | 2.01 |
| 87 | 449.2 | 2.13 |
| 88 | 449.2 | 2.16 |
| 89 | 427.2 | 2.16 |
| 90 | 426.2 | 2.07 |
| 91 | 440.4 | 2.07 |
| 92 | 425.2 | 1.78 |
| 93 | 453.4 | 2.06 |
| 94 | 451.4 | 1.87 |
| 95 | 465.2 | 2.01 |
| 96 | 415.4 | 2.16 |
| 97 | 425.2 | 2.16 |
| 98 | 439.4 | 2.25 |
| 99 | 453.2 | 2.39 |
| 100 | 425.2 | 2.16 |
| 101 | 439.4 | 2.26 |
| 102 | 453.2 | 2.38 |
| 103 | 447.4 | 2.1 |
| 104 | 439.4 | 2.16 |
| 105 | 453.2 | 2.26 |
| 106 | 467.4 | 2.4 |
| 107 | 443.5 | 2.27 |
| 108 | 421.2 | 1.66 |
| 109 | 421.2 | 1.66 |
| 110 | 457.4 | 2.06 |
| 111 | 457.4 | 2.08 |
| 112 | 426.2 | 1.82 |
| 113 | 513.4 | 2.2 |
| 114 | 447.2 | 1.94 |
| 115 | 455.4 | 2.07 |
| 116 | 440 | 2.09 |
| 117 | 476.2 | 2.43 |
| 118 | 460.4 | 2.42 |
| 119 | 368.5 | 1.9 |

V. Assays

Functional Mobilization of Intracellular Calcium to Determine Muscarinic Receptor Activity:

CHO cells expressing muscarinic receptors ($M_1$ to $M_5$) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat#12430-054), containing 25 mM Hepes and supplemented with Fetal Bovine Serum (Hyclone, cat# SH30071.03), 0.1 mM of MEM non-essential amino acids (GIBCO, Cat#11140-050), 1 mM MEM Sodium Pyruvate (GIBCO Cat#11360-070) and 100 units/ml of Penicillin G and 100 µg/ml of Streptomycin (GIBCO Cat#15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat#15040-066), collected by centrifugation and seeded 18-24 hours prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instrunents, ELX 405) using bath 1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat # R7181) adding 5 µl of a 5× solution dye in Bath 1 containing 1 mM Probenecid (10 ml per dye flask cat# R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat#3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family ($M_1$ to $M_5$ cells). Compounds were also screened for activity on other proteins such as other GPCRs and ion channels to determine selectivity on M4 receptors.

The compounds of the present invention were found to modulate the $M_1$ and/or $M_4$ muscarinic receptors selectively over the other receptor types.

Examples of activities and efficacies of the muscarinic compounds of formulae (I, Ia, Ib, Ic, Id, and Ie) on modulating $M_1$ and $M_4$ receptors are shown below in Table 4. The compound activity for the $M_1$ and $M_4$ is illustrated with "+++" if activity was measured to be less than 2.0 µM, "++" if activity was measured to be from 2.0 µM to 10.0 µM, "+" if activity was measured to be greater than 10.0 µM, and "−" if no data was available. The efficacy for $M_1$ and $M_4$ modulation is illustrated with "+++" if efficacy was calculated to be greater than 100%, "++" if efficacy was calculated to be from 100% to 25%, "+" if efficacy was calculated to be less than 25%, and "−" if no data was available. It should be noted that 100% efficacy is the maximum response obtained with the Carbachol control.

| Cmd No. | $M_1$ Activity | $M_4$ Activity | $M_1$ Efficacy | $M_4$ Efficacy |
|---|---|---|---|---|
| 1 | +++ | +++ | ++ | ++ |
| 2 | +++ | +++ | ++ | ++ |
| 3 | +++ | +++ | ++ | +++ |
| 4 | +++ | +++ | ++ | ++ |
| 5 | +++ | +++ | ++ | ++ |
| 6 | +++ | +++ | ++ | ++ |
| 7 | +++ | +++ | ++ | ++ |
| 8 | +++ | +++ | ++ | ++ |
| 9 | +++ | +++ | ++ | ++ |
| 10 | +++ | +++ | ++ | ++ |
| 11 | +++ | +++ | +++ | +++ |
| 12 | +++ | +++ | +++ | ++ |
| 13 | +++ | +++ | ++ | ++ |
| 14 | +++ | +++ | ++ | ++ |
| 15 | +++ | +++ | ++ | ++ |
| 16 | +++ | +++ | ++ | ++ |
| 17 | +++ | +++ | ++ | ++ |
| 18 | ++ | +++ | ++ | ++ |
| 19 | ++ | +++ | + | ++ |
| 20 | ++ | +++ | ++ | ++ |
| 21 | ++ | ++ | ++ | + |
| 22 | ++ | ++ | ++ | ++ |
| 23 | ++ | ++ | ++ | ++ |
| 24 | ++ | ++ | ++ | + |
| 25 | ++ | ++ | ++ | ++ |
| 26 | ++ | +++ | ++ | ++ |
| 27 | +++ | +++ | ++ | ++ |
| 28 | +++ | +++ | ++ | ++ |
| 29 | +++ | +++ | +++ | ++ |
| 30 | +++ | +++ | ++ | ++ |
| 31 | +++ | +++ | ++ | ++ |
| 32 | +++ | +++ | ++ | ++ |
| 33 | + | + | + | + |
| 34 | + | ++ | + | + |
| 35 | ++ | ++ | + | + |
| 36 | + | + | + | + |
| 37 | + | + | + | + |
| 38 | ++ | +++ | ++ | ++ |
| 39 | +++ | +++ | ++ | ++ |
| 40 | +++ | +++ | ++ | ++ |
| 41 | +++ | +++ | ++ | ++ |
| 42 | +++ | +++ | ++ | ++ |
| 43 | +++ | +++ | ++ | ++ |
| 44 | +++ | +++ | ++ | ++ |
| 45 | ++ | +++ | ++ | ++ |
| 46 | +++ | +++ | ++ | ++ |
| 47 | +++ | +++ | ++ | ++ |
| 48 | +++ | +++ | ++ | ++ |
| 49 | +++ | +++ | ++ | ++ |
| 50 | +++ | +++ | ++ | ++ |
| 51 | +++ | +++ | ++ | ++ |

-continued

| Cmd No. | M₁ Activity | M₄ Activity | M₁ Efficacy | M₄ Efficacy |
|---|---|---|---|---|
| 52 | +++ | +++ | ++ | +++ |
| 53 | +++ | +++ | ++ | +++ |
| 54 | +++ | +++ | ++ | ++ |
| 55 | ++ | +++ | + | ++ |
| 56 | ++ | +++ | ++ | ++ |
| 57 | +++ | +++ | ++ | ++ |
| 58 | ++ | +++ | ++ | ++ |
| 59 | +++ | +++ | ++ | ++ |
| 60 | +++ | +++ | ++ | ++ |
| 61 | ++ | +++ | + | ++ |
| 62 | ++ | +++ | ++ | ++ |
| 63 | +++ | +++ | ++ | ++ |
| 64 | ++ | +++ | ++ | ++ |
| 65 | +++ | +++ | ++ | ++ |
| 66 | − | − | − | − |
| 67 | +++ | +++ | ++ | ++ |
| 68 | +++ | +++ | ++ | +++ |
| 69 | +++ | +++ | ++ | ++ |
| 70 | ++ | +++ | ++ | ++ |
| 71 | +++ | +++ | ++ | ++ |
| 72 | +++ | +++ | ++ | ++ |
| 73 | ++ | +++ | + | ++ |
| 74 | +++ | +++ | ++ | ++ |
| 75 | ++ | +++ | ++ | ++ |
| 76 | +++ | +++ | +++ | +++ |
| 77 | +++ | +++ | ++ | ++ |
| 78 | +++ | +++ | ++ | ++ |
| 79 | +++ | +++ | ++ | ++ |
| 80 | +++ | +++ | ++ | +++ |
| 81 | +++ | +++ | ++ | ++ |
| 82 | ++ | +++ | ++ | ++ |
| 83 | ++ | +++ | ++ | ++ |
| 84 | +++ | +++ | ++ | ++ |
| 85 | +++ | +++ | ++ | +++ |
| 86 | +++ | +++ | ++ | ++ |
| 87 | + | +++ | + | ++ |
| 88 | ++ | +++ | ++ | ++ |
| 89 | ++ | ++ | + | ++ |
| 90 | ++ | ++ | ++ | ++ |
| 91 | ++ | +++ | ++ | ++ |
| 92 | +++ | +++ | +++ | +++ |
| 93 | +++ | +++ | ++ | ++ |
| 94 | +++ | +++ | ++ | ++ |
| 95 | +++ | +++ | ++ | ++ |
| 96 | +++ | +++ | ++ | +++ |
| 97 | +++ | +++ | ++ | ++ |
| 98 | +++ | +++ | ++ | ++ |
| 99 | +++ | +++ | ++ | +++ |
| 100 | +++ | +++ | ++ | ++ |
| 101 | +++ | +++ | ++ | +++ |
| 102 | +++ | +++ | ++ | +++ |
| 103 | +++ | +++ | ++ | +++ |
| 104 | +++ | +++ | +++ | +++ |
| 105 | +++ | +++ | +++ | +++ |
| 106 | +++ | +++ | ++ | ++ |
| 107 | +++ | +++ | +++ | +++ |
| 108 | +++ | +++ | ++ | +++ |
| 109 | +++ | +++ | ++ | +++ |
| 110 | ++ | ++ | + | + |
| 111 | ++ | ++ | + | + |
| 112 | ++ | + | + | + |
| 113 | +++ | + | ++ | + |
| 114 | + | +++ | + | ++ |
| 115 | + | +++ | + | + |
| 116 | + | + | + | + |
| 117 | + | ++ | + | + |
| 118 | ++ | ++ | ++ | + |
| 119 | + | +++ | + | ++ |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound of formula I

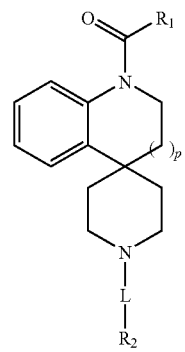

or a pharmaceutically acceptable salt thereof, wherein
  $R_1$ is an optionally substituted aliphatic or $-NR_6R'_6$;
    Each of $R_6$ and $R'_6$ is independently hydrogen or an optionally substituted $C_{1-4}$ aliphatic, or
    $R_6$ and $R'_6$ together with the nitrogen atom to which they are attached form an optionally substituted 4-7 membered heterocycloaliphatic;
  L is a bond or an unsubstituted methylene group;
    $R_2$ is an optionally substituted bicyclic cycloaliphatic; or
    $R_2$ is a monocyclic cycloaliphatic optionally substituted with a heteroaryl; or
    $R_2$ is pyrrolidine-yl, 1,3-dioxolane-yl, imidazolidine-yl, 2-pyrazoline-yl, pyrazolidine-yl, piperidine-yl, 1,4-dioxane-yl, morpholine-yl, azepane-yl, azocane-yl, or piperazine-yl, each of which is optionally substituted with 1 to 3 of halo, or aliphatic, alkoxy, (aliphatic(oxy))carbonyl, (alkoxy(alkoxy))carbonyl, cycloaliphatic, heterocycloaliphatic, heteroaryl, amido, amino, (heterocycloaliphatic)oxy, or (heterocycloaliphatic(oxy))carbonyl, each of which is optionally substituted; or
    $R_2$ is an optionally substituted bicyclic heterocycloaliphatic that has 1-3 heteroatoms independently selected from N, O, and S;
  Each p is 0 or 1; and
  When p is 0, then $R_1$ is an optionally substituted $C_{2-8}$ alkyl, an optionally substituted alkenyl, an optionally substituted alkynyl, N,N-dimethylamino, or $R_6$ and $R'_6$ together with the nitrogen atom to which they are attached form an optionally substituted 4-7 membered heterocycloaliphatic.

2. The compound of claim 1, wherein $R_1$ is an optionally substituted aliphatic.

3. The compound of claim 2, wherein $R_1$ is a methyl, ethyl, propyl, isopropyl, or butyl, each of which is optionally substituted.

4. The compound of claim 3, wherein $R_1$ is a methyl that is optionally substituted with 1-3 of halo, oxo, cyano, cycloaliphatic, heterocycloaliphatic, aryl, or heteroaryl.

5. The compound of claim 4, wherein $R_1$ is an unsubstituted methyl.

6. The compound of claim 1, wherein $R_1$ is $-NR_6R'_6$ and each of $R_6$ and $R'_6$ is independently hydrogen or an optionally substituted $C_{1-4}$ aliphatic.

7. The compound of claim 6, wherein each $R_6$ and $R'_6$ is independently hydrogen or $C_{1-4}$ aliphatic that is that is optionally substituted with 1-3 of hydroxy, oxo, halo, cyano, nitro, or optionally substituted cycloaliphatic, optionally substituted heterocycloaliphatic, optionally substituted aryl, optionally substituted heteroaryl, or combinations thereof.

8. The compound of claim 6, wherein each $R_6$ and $R'_6$ is independently hydrogen, optionally substituted methyl, optionally substituted ethyl, or optionally substituted propyl.

9. The compound of claim 8, wherein both $R_6$ and $R'_6$ are methyl.

10. A compound of formula I

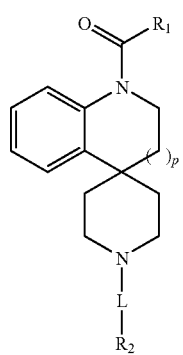

I or a pharmaceutically acceptable salt thereof, wherein
$R_1$ is $-NR_6R'_6$;
  $R_6$ and $R'_6$ together with the nitrogen atom to which they are attached form an optionally substituted 4-7 membered heterocycloaliphatic;
L is $-(CH_2)_n-$, wherein n is 0-2;
$R_2$ is a cycloaliphatic or a heterocycloaliphatic, each of which is optionally substituted with 1-3 of $R_3$;
  Each $R_3$ is $-Z^A R_4$, wherein each $Z^A$ is independently a bond or an optionally substituted branched or straight $C_{1-6}$ aliphatic chain wherein up to two carbon units of $Z^A$ are optionally and independently replaced by $-CO-$, $-CS-$, $-CONR^A-$, $-CONR^A NR^A-$, $-CO_2-$, $-OCO-$, $-NR^A CO_2-$, $-O-$, $-NR^A CONR^A-$, $-OCONR^A-$, $-NR^A NR^A-$, $-NR^A CO-$, $-S-$, $-SO-$, $-SO_2-$, $-NR^A-$, $-SO_2 NR^A-$, $-NR^A SO_2-$, or $-NR^A SO_2 NR^A-$;
  Each $R_4$ is independently $R^A$, halo, $-OH$, $-NH_2$, $-NO_2$, $-CN$, or $-OCF_3$;
  Each $R^A$ is independently hydrogen, an optionally substituted aliphatic, an optionally substituted cycloaliphatic, an optionally substituted heterocycloaliphatic, an optionally substituted aryl, or an optionally substituted heteroaryl; and
  Each p is 0 or 1.

11. The compound of claim 1, wherein $R_2$ is an optionally substituted bicyclic heterocycloaliphatic that has 1-3 heteroatoms independently selected from N, O, and S.

12. The compound of claim 11, wherein $R_2$ is an optionally substituted 7-10 membered bridged bicyclic heterocycloaliphatic or a fused bicyclic heterocycloaliphatic, each of which is optionally substituted.

13. The compound of claim 12, wherein $R_2$ is 5-azabicyclo[2.1.1]hexane-yl, 7-azabicyclo[2.2.1]heptane-yl, or 8-azabicyclo[3.2.1]octane-yl, each of which is optionally substituted with 1-3 of halo, or aliphatic, alkoxy, (aliphatic(oxy))carbonyl, (alkoxy(alkoxy))carbonyl, cycloaliphatic, heterocycloaliphatic, aryl, heteroaryl, acyl, amido, amino, (heterocycloaliphatic)oxy, (heterocycloaliphatic(oxy))carbonyl.

14. The compound of claim 1, wherein $R_2$ is one selected from 1-methoxycarbonylpiperidine-4-yl; 1-ethoxycarbonylpiperidine-4-yl; propoxycarbonylpiperidine-4-yl; 1-isopropoxycarbonylpiperidine-4-yl; 1-((2,2-difluoroethoxy)carbonyl)piperidine-4-yl; 1-(2-methoxy(ethoxy)carbonyl)piperidine-4-yl; 1-((3-butynoxy)carbonyl)piperidine-4-yl; 8-(methoxy(carbonyl))-8-azabicyclo[3.2.1]octane-3-yl; 8-(ethoxy(carbonyl))-8-azabicyclo[3.2.1]octane-3-yl; 8-(propoxy(carbonyl))-8-azabicyclo[3.2.1]octane-3-yl; 8-(isopropoxycarbonyl)-8-azabicyclo[3.2.1]octane-3-yl; 8-((2,2-difluoroethoxy)carbonyl)-8-azabicyclo[3.2.1]octane-3-yl; 8-(methoxy(ethoxy)carbonyl)-8-azabicyclo[3.2.1]octane-3-yl; 8-(3-butynyloxy(carbonyl))-8-azabicyclo[3.2.1]octane-3-yl; 1-(pyrazine-2-yl)piperidine-4-yl; 1-(1,2,4-thiadiazole-5-yl)piperidine-4-yl; 1-(methoxy(carbonyl))pyrrolidine-3-yl; 1-(ethoxy(carbonyl))pyrrolidine-3-yl; 1-(isopropoxy(carbonyl))pyrrolidine-3-yl; 1-((2,2-difluoroethoxy)carbonyl)pyrrolidine-3-yl; 1-(2-(methoxy(ethoxy))carbonyl)pyrrolidone-3-yl; 1-(propoxy(carbonyl))pyrrolidine-3-yl; 1-((2,2-difluoroethoxy)carbonyl)pyrrolidone-3-yl; 8-(3-methyl(1,2,4-thiadiazole-5-yl))-8-azabicyclo[3.2.1]octane-3-yl; 8-(3-ethyl(1,2,4-thiadiazole-5-yl))-8-azabicyclo[3.2.1]octane-3-yl; 1-(methoxy(carbonyl))azepane-4-yl; 1-(ethoxy(carbonyl))azepane-4-yl; 1-(propoxy(carbonyl))azepane-4-yl; 1-(isopropoxy(carbonyl))azepane-4-yl; 1-((2,2-difluoroethoxy)carbonyl)azepane-4-yl; 1-(2-(methoxy(ethoxy))carbonyl)azepane-4-yl; (tetrahydrofuran-3-yl(oxy(carbonyl)))azepane-4-yl; (tetrahydrofuran-3-yl(oxy(carbonyl)))pyrrolidine-3-yl; 4-(3-methyl(1,2,4-thiadiazole-5-yl))cyclohexane-1-yl; 1-(1,2,4-thiadiazole-5-yl)piperidine-4-yl; 1-(3-ethyl(1,2,4-thiadiazole-5-yl))piperidine-4-yl; 1-(6-chloro(pyrazine-2-yl))piperidine-4-yl; 1-(quinoxaline-2-yl)piperidine-4-yl; 1-(6-methyl(pyrazine-2-yl))piperidine-4-yl; 1-(methoxy(carbonyl))azocane-5-yl; 1-(ethoxy(carbonyl))-4-methylpiperidine-4-yl; 1-(pyrazine-2-yl-(4-methyl))piperidine-4-yl; 1-(3-methyl-(1,2,4-thiadiazole-5-yl))pyrrolidine-3-yl; 1-(3-ethyl-(1,2,4-thiadiazole-5-yl))pyrrolidine-3-yl; 1-((5,6-dimethyl(pyrazine-2-yl)))pyrrolidine-3-yl; 1-((5,6-dimethyl(pyrazine-2-yl)))piperidine-4-yl; 1-(1,2,4-thiadiazole-5-yl)piperidine-4-yl; 1-(thiazole-2-yl)piperidine-4-yl; 1-(4-methyl(thiazole-2-yl))piperidine-4-yl; 4-(1,2,4-thiadiazole-5-yl)cyclohexane-1-yl; 1-(2-hydroxy-(6-phenyl-(pyrazine-6-yl)))piperidine-4-yl; 1-(6-(2-hydroxyphenyl)pyrazine-2-yl)piperidin-4-yl; 1-(5-methyl(thiazole-2-yl))piperidine-4-yl; 1-(benzo(d)thiazole-2-yl)piperidine-4-yl; 1-(benzo(d)oxazole-2-yl)piperidine-4-yl; 1-(prop-2-ynyl(oxy(carbonyl)))piperidine-4-yl; 1-(pent-2-ynyl(oxy(carbonyl)))piperidine-4-yl; 8-(prop-2-ynyl(oxy(carbonyl)))-8-azabicyclo[3.2.1]octane-3-yl; 8-(but-2-ynyl(oxy(carbonyl)))-8-azabicyclo[3.2.1]octane-3-yl; 1-(prop-2-ynyl(oxy(carbonyl)))pyrrolidine-3-yl; 1-(but-2-ynyl(oxy(carbonyl)))pyrrolidine-3-yl; 1-(pent-2-ynyl(oxy(carbonyl)))pyrrolidine-3-yl; 8-(pyrazine-2-yl)-8-azabicyclo[3.2.1]octane-3-yl; 1-(prop-2-ynyl(oxy(carbonyl)))azepane-4-yl; 1-(but-2-ynyl(oxy(carbonyl)))azepane-4-yl; 1-(pent-2-ynyl(oxy(carbonyl)))azepane-4-yl; 1-(ethoxy(carbonyl))azocane-5-yl; 1-(pyrazine-2-yl)pyrrolidone-3-yl; and piperidine-4-yl.

15. A pharmaceutical composition comprising a compound according to claim 1 and a pharmaceutical carrier.

16. A compound selected from
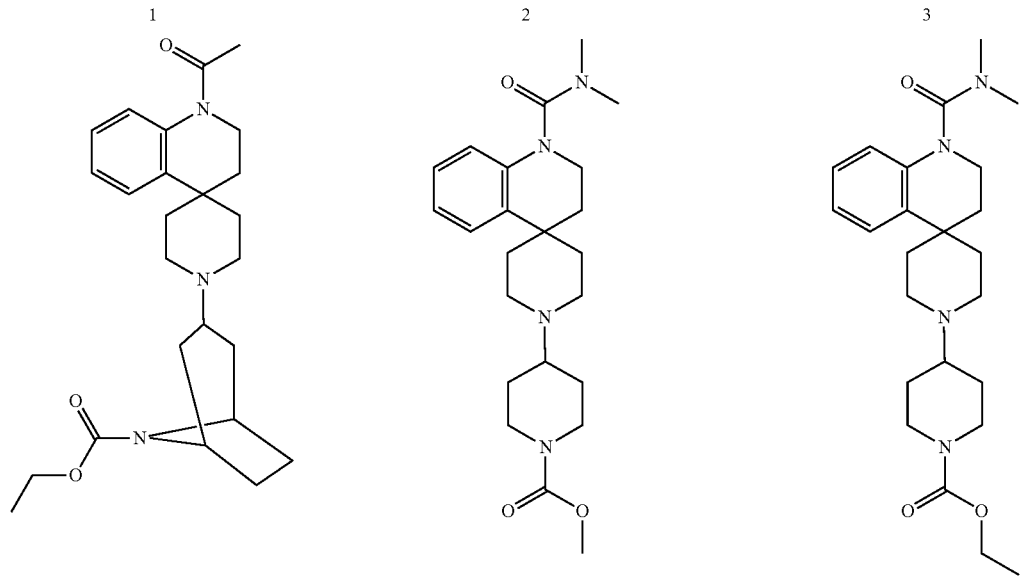
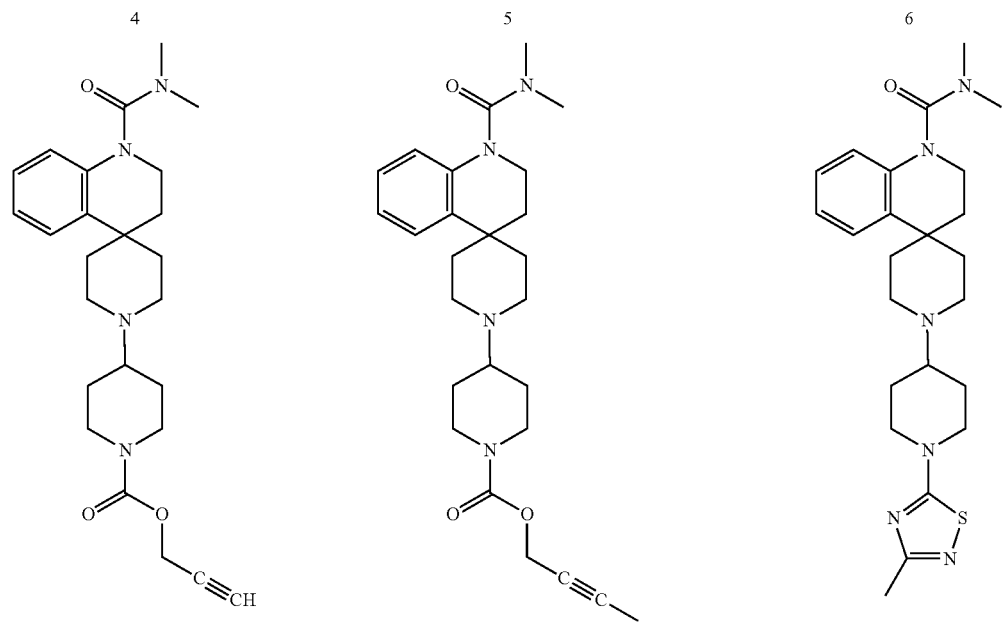

| 111 | | 112 |
|---|---|---|
| -continued | | |
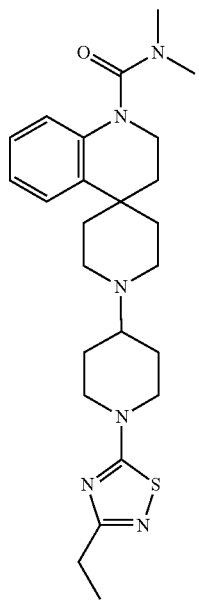 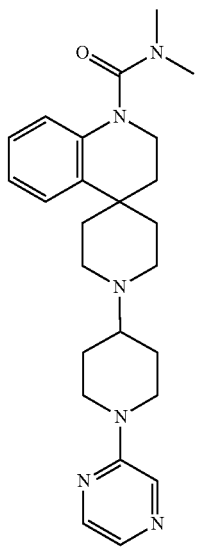 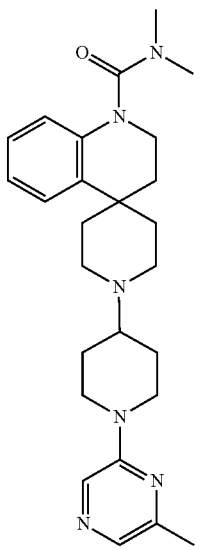
| 10 | 11 | 12 |
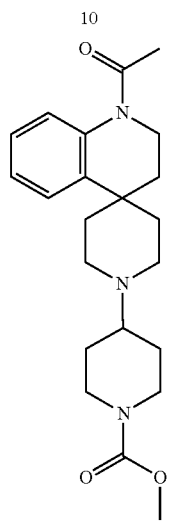 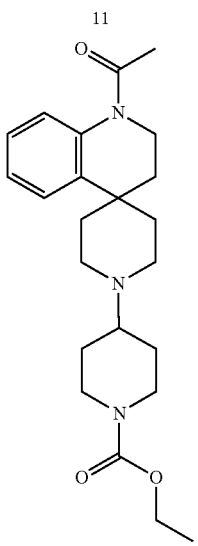 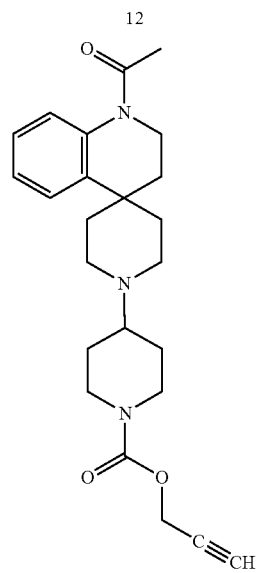
| 13 | 14 | 15 |

| 113 | | 114 |
|---|---|---|
| 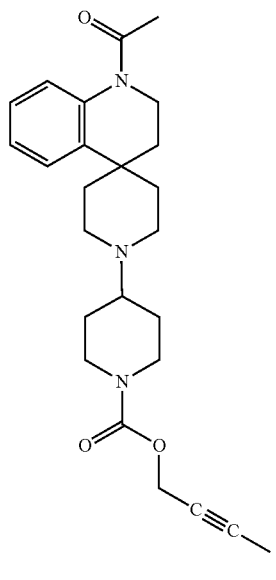 | 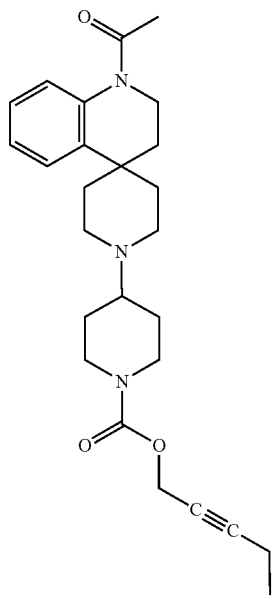 | 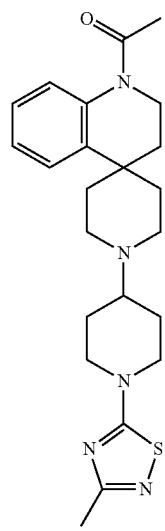 |
| 16 | 17 | 18 |
| 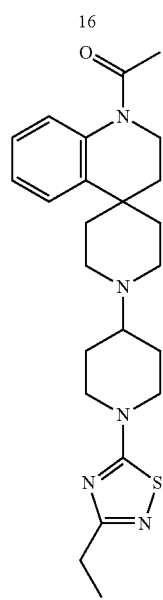 | 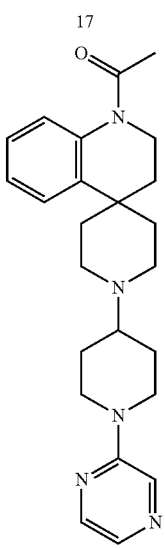 | 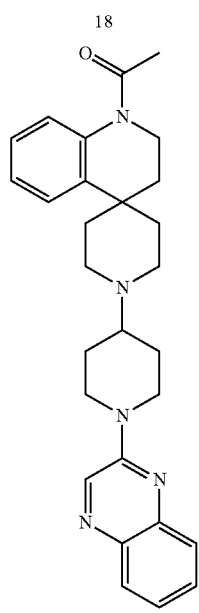 |
| 19 | 20 | 21 |

| 115 | | 116 |
|---|---|---|
| 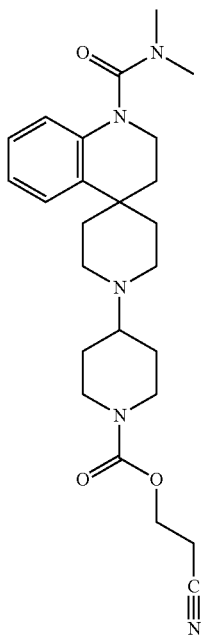 | 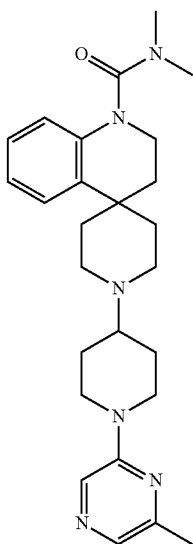 | 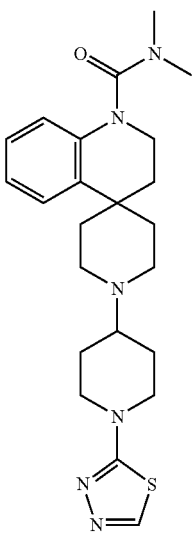 |
| 22 | 23 | 24 |
| 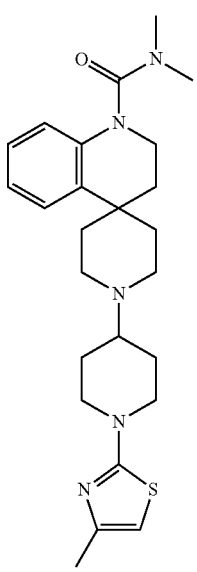 | 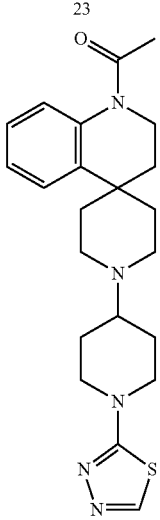 | 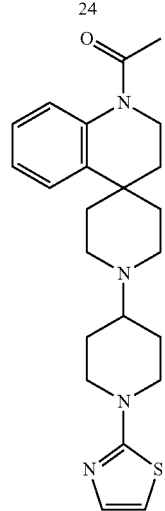 |
| 25 | 26 | 27 |

| 28 | 29 | 30 |
|---|---|---|
| 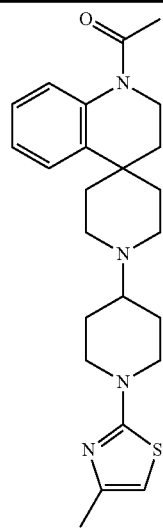 | 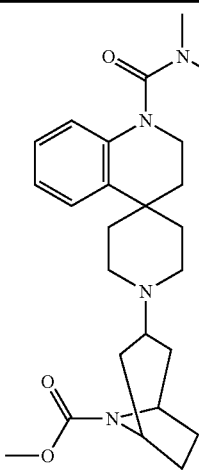 | 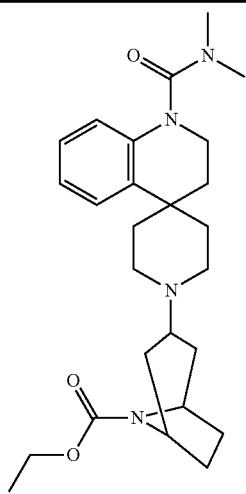 |
| 31 | 32 | 33 |
| 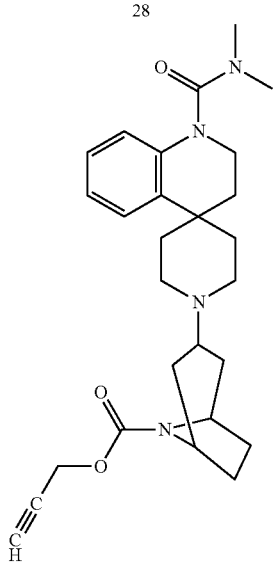 | 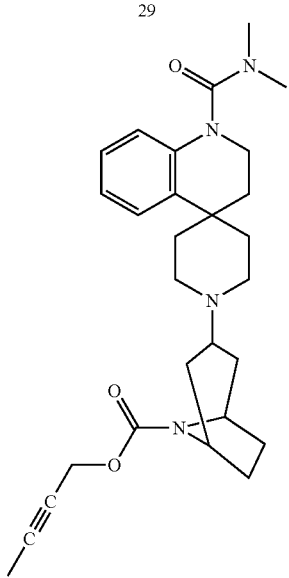 | 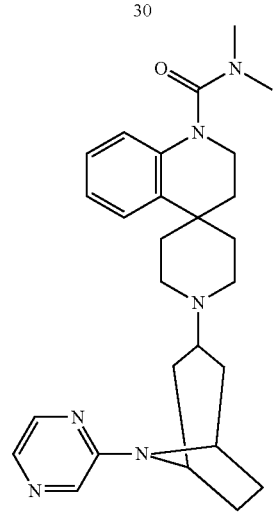 |
| 34 | 35 | 36 |
| 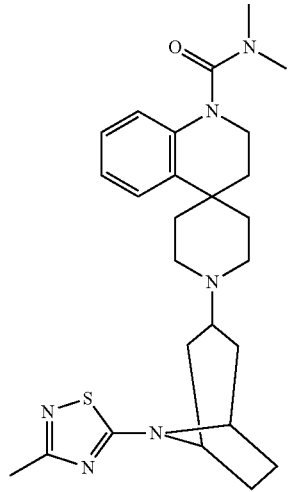 | 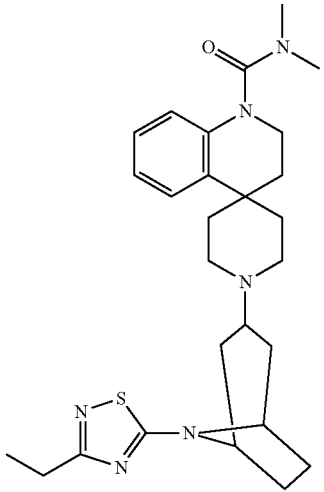 | 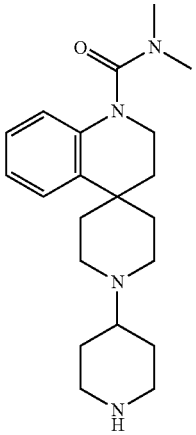 |

-continued
| 37 | 38 | 39 |
|---|---|---|
| 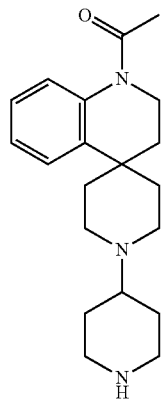 | 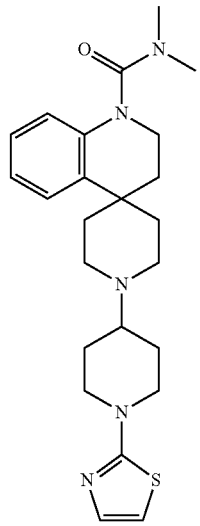 | 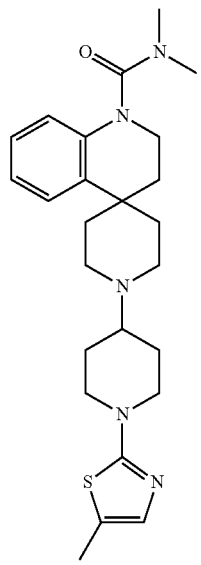 |
| 40 | 41 | 42 |
| 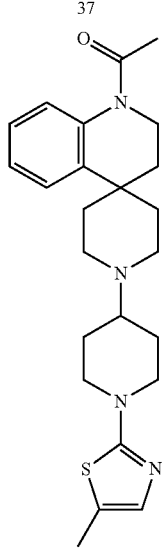 | 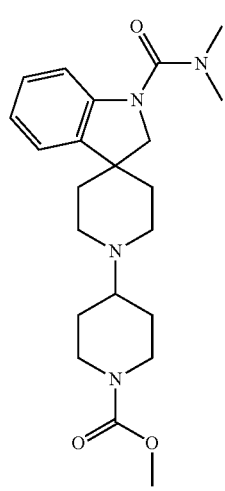 | 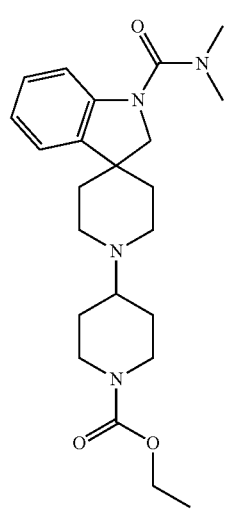 |

-continued
| 121 | | 122 |
|---|---|---|
| 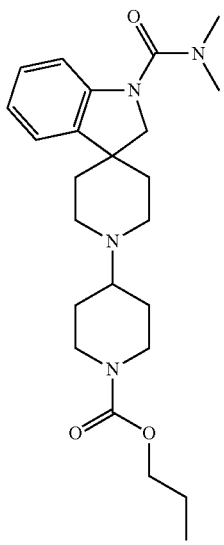 | 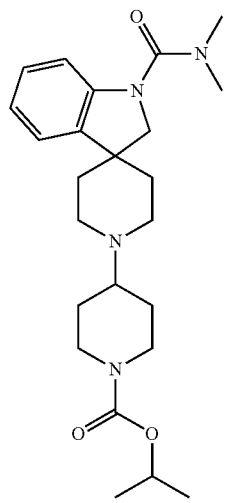 | 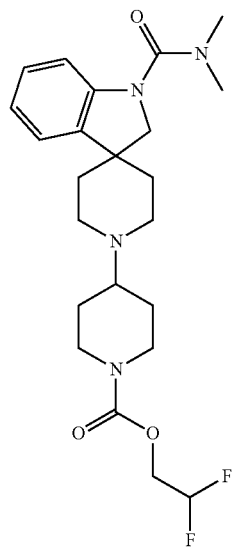 |
| 43 | 44 | 45 |
| 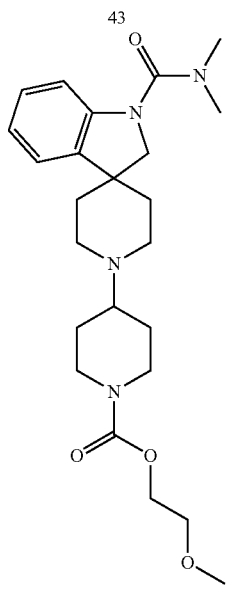 | 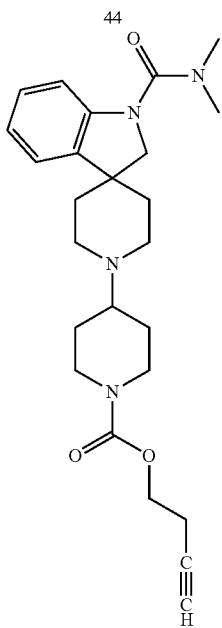 | 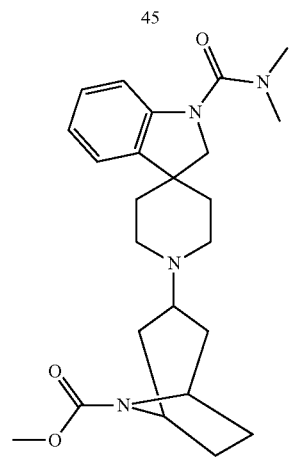 |
| 46 | 47 | 48 |
| 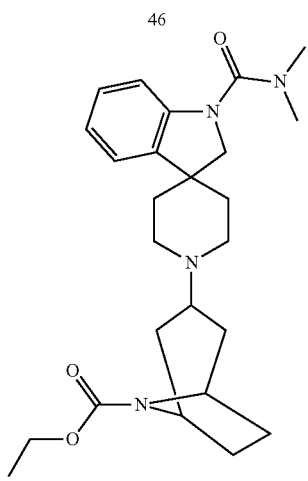 | 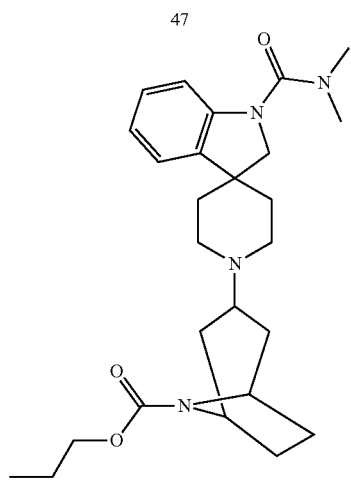 | 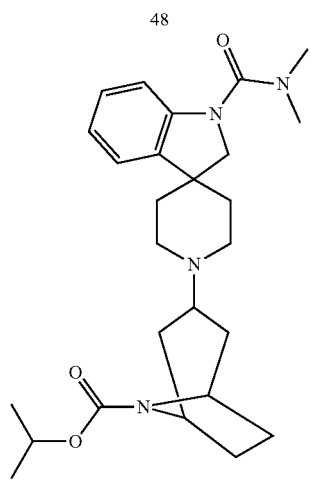 |
| 49 | 50 | 51 |

-continued
| 123 | | 124 |
|---|---|---|
| 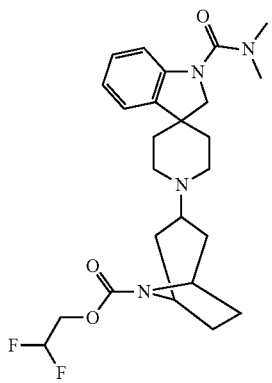 | 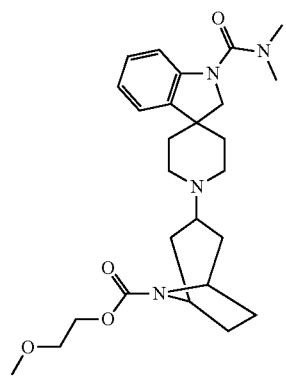 | 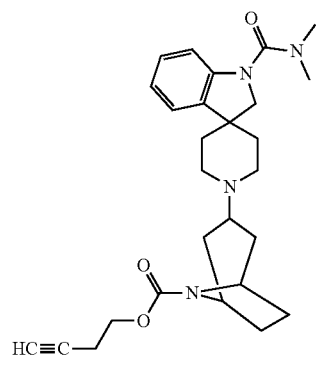 |
| 52 | 53 | 54 |
| 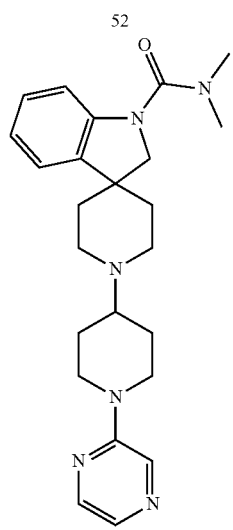 | 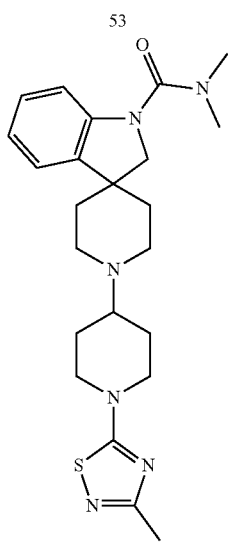 | 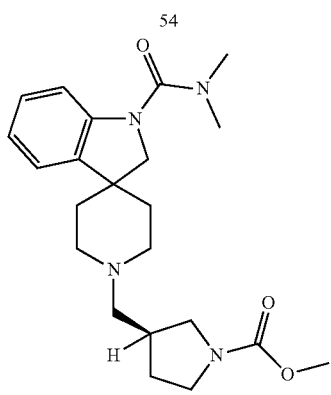 |
| 55 | 56 | 57 |
| 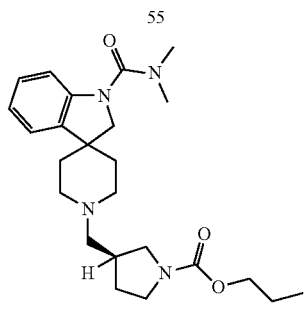 | 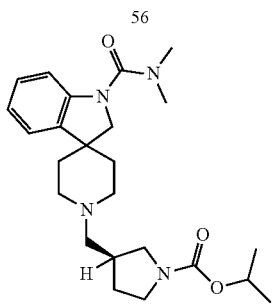 | 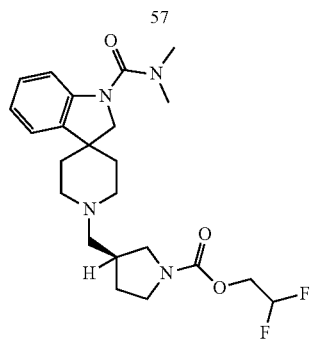 |
| 58 | 59 | 60 |
| 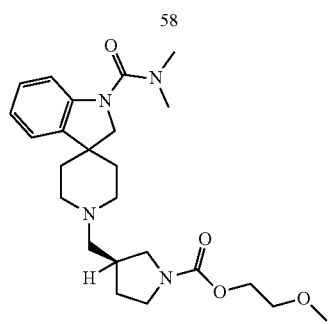 | 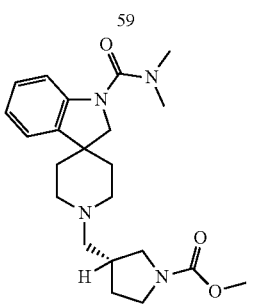 | 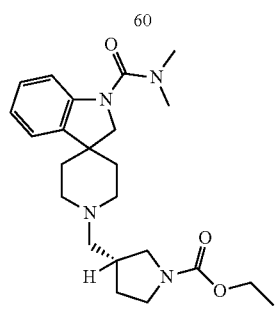 |
| 61 | 62 | 63 |

| 125 | | 126 |
|---|---|---|
| 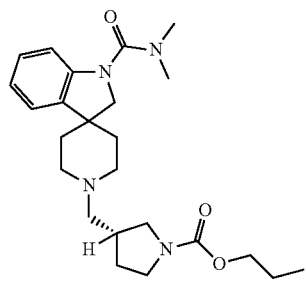 | 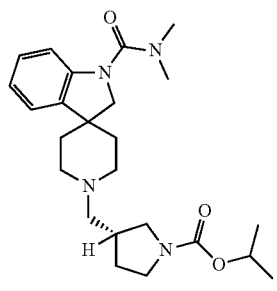 | 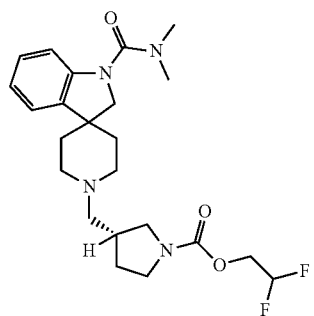 |
| 64 | 65 | 66 |
| 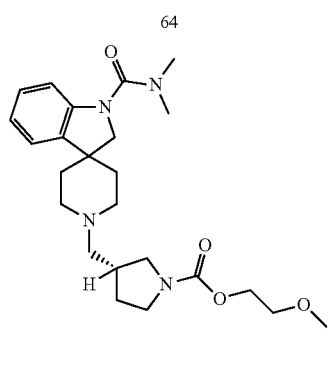 | 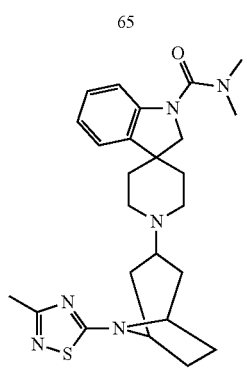 | 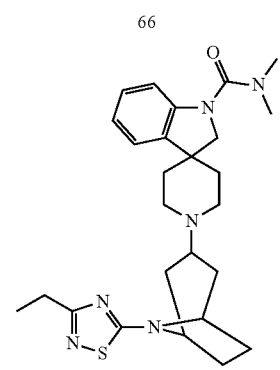 |
| 67 | 68 | 69 |
| 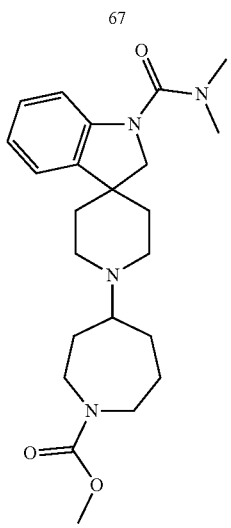 | 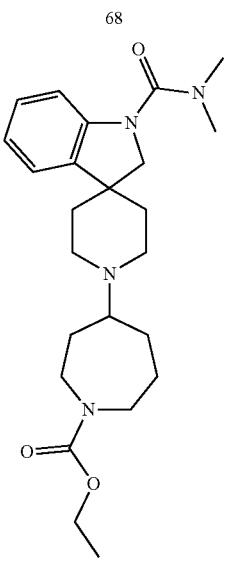 | 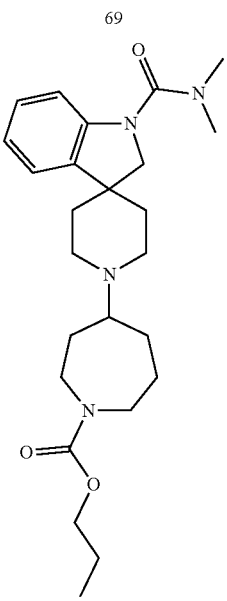 |
| 70 | 71 | 72 |

| 126 | 127 | 128 |
|---|---|---|
| 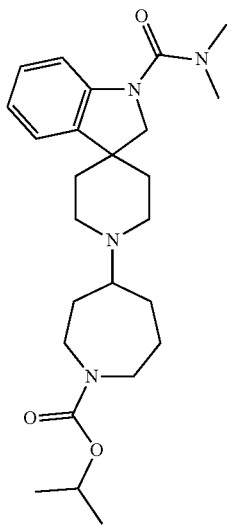 | 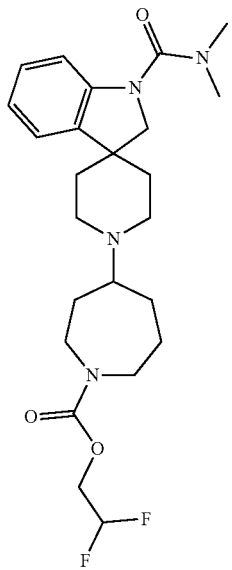 | 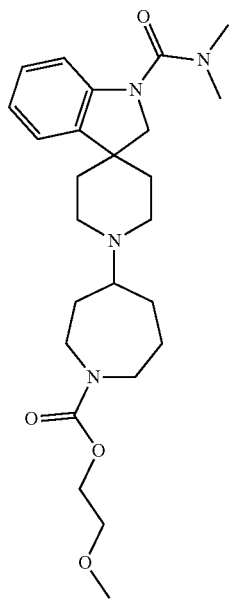 |
| 73 | 74 | 75 |
|---|---|---|
| 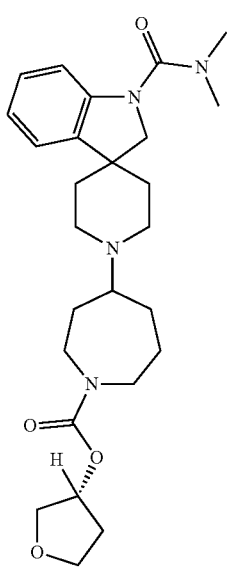 | 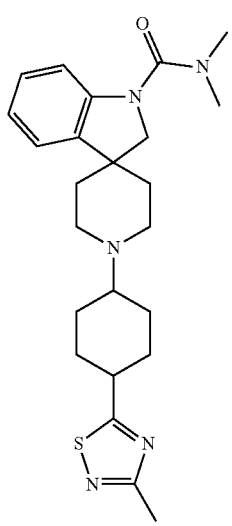 | 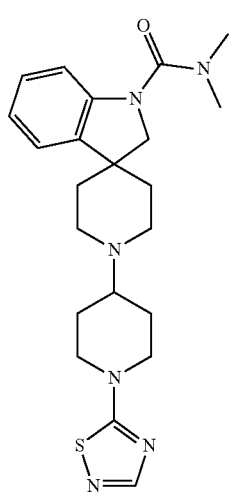 |
| 76 | 77 | 78 |

US 8,263,605 B2
129 130
-continued
| 79 | 80 | 81 |
|---|---|---|
| 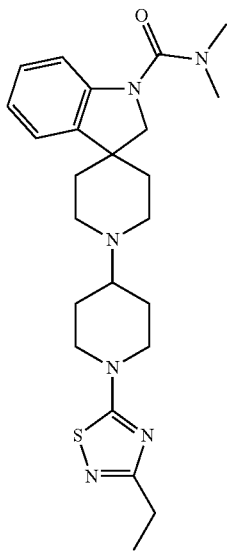 | 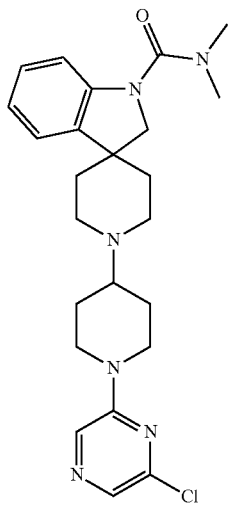 | 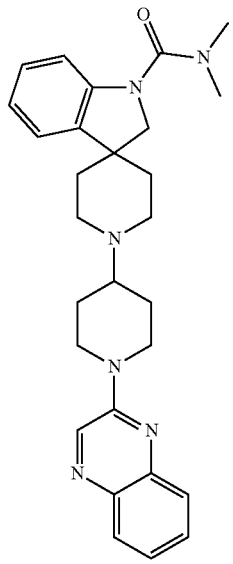 |
| 82 | 83 | 84 |
| 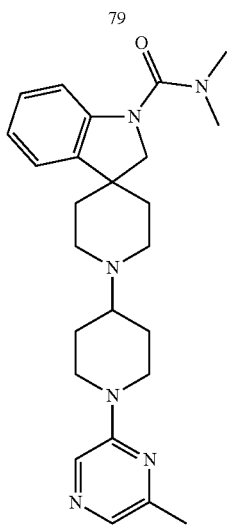 | 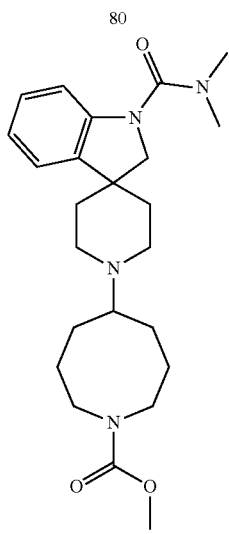 | 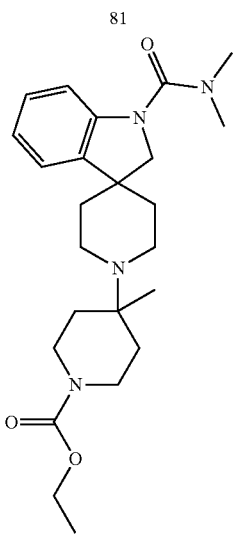 |
| 85 | 86 | 87 |
| 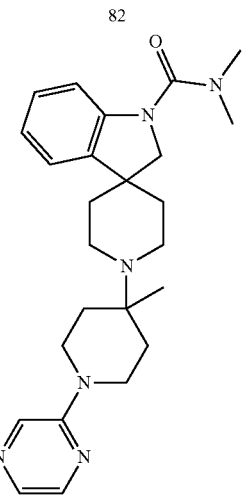 | 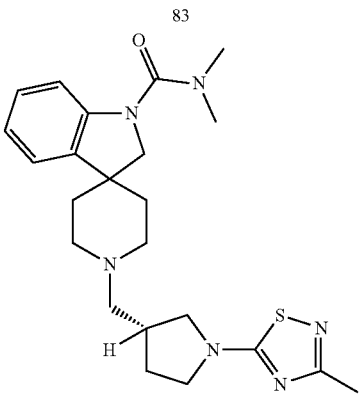 | 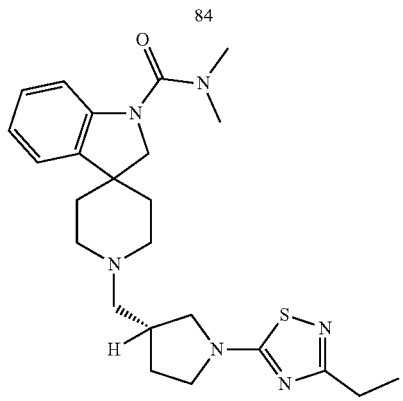 |

| 131 | | 132 |
|---|---|---|
| 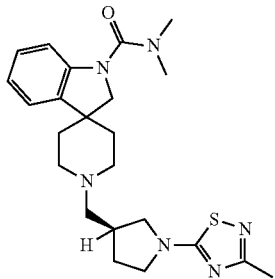 | 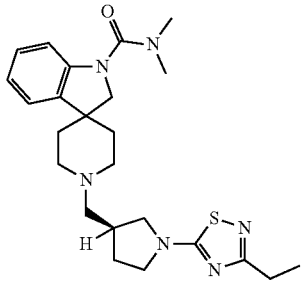 | 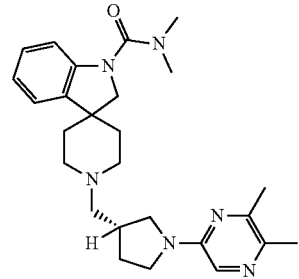 |
| 88 | 89 | 90 |
| 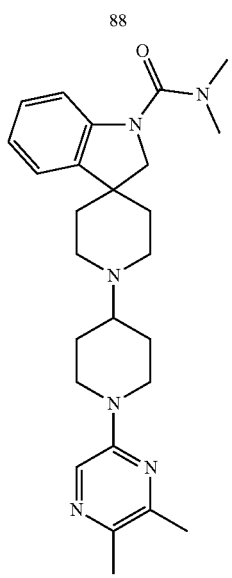 | 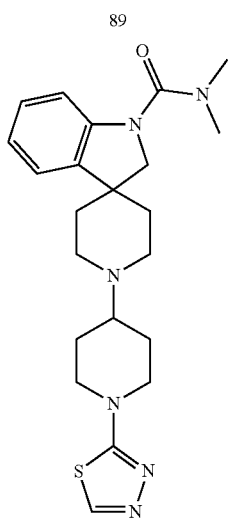 | 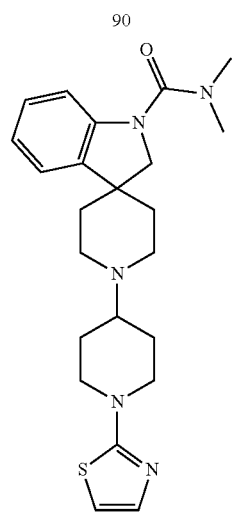 |
| 91 | 92 | 93 |
| 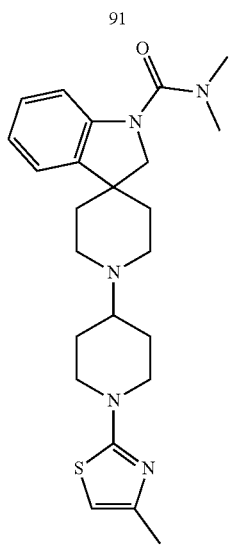 | 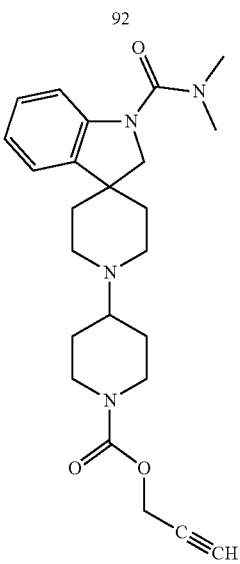 | 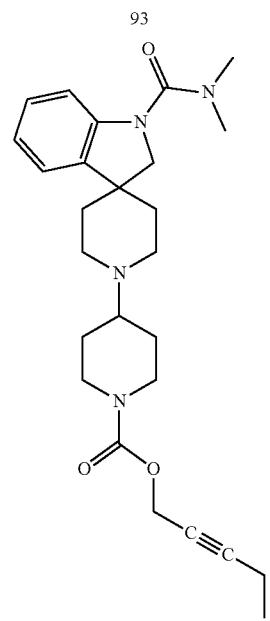 |
| 94 | 95 | 96 |

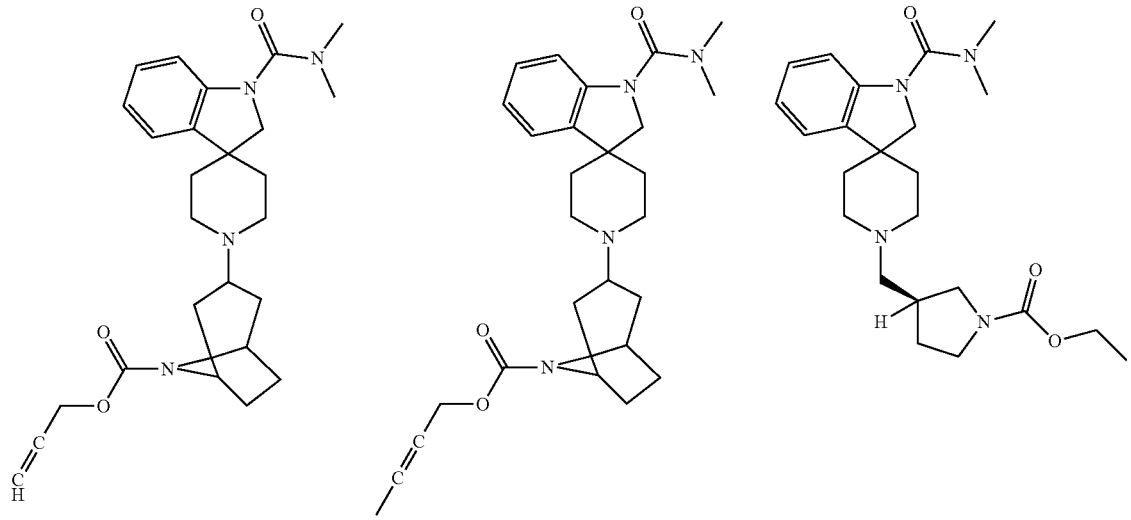
97  98  99
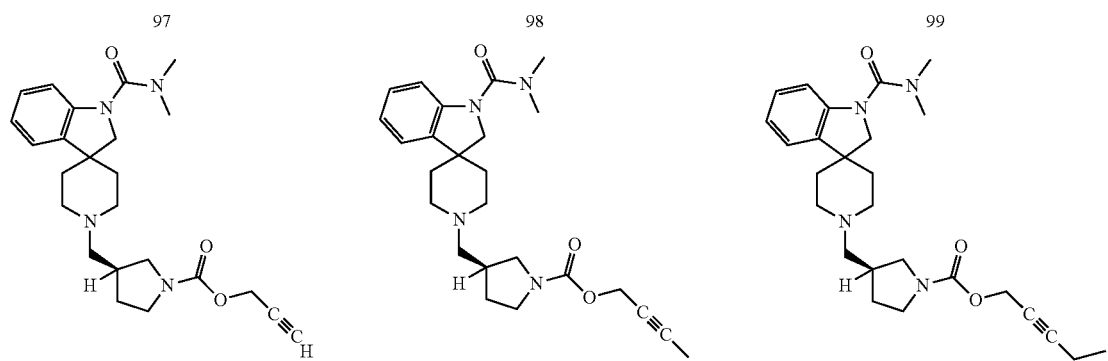
100  101  102
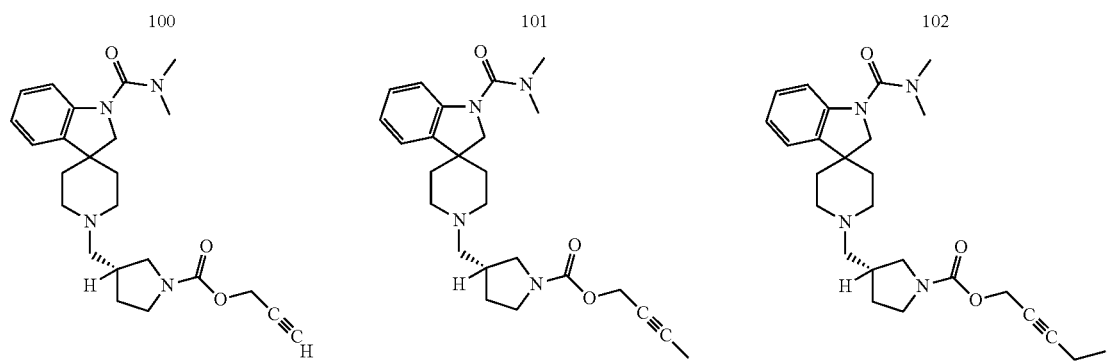
103  104  105

-continued
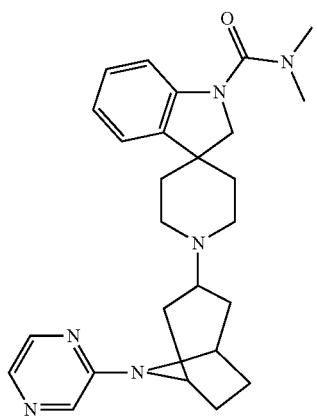
106
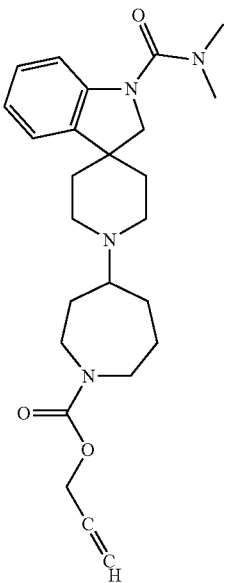
107
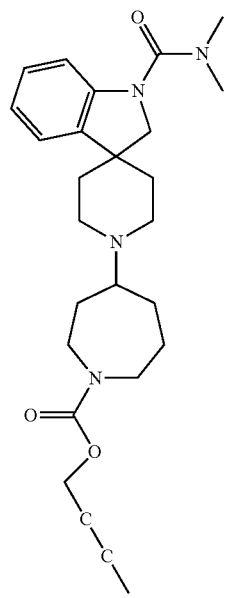
108
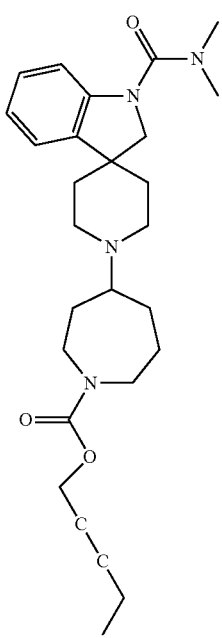
109
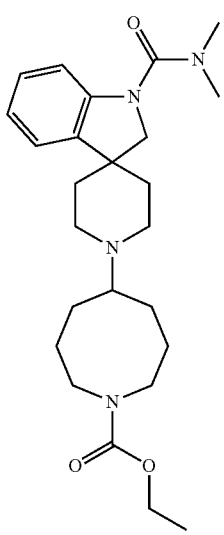
110
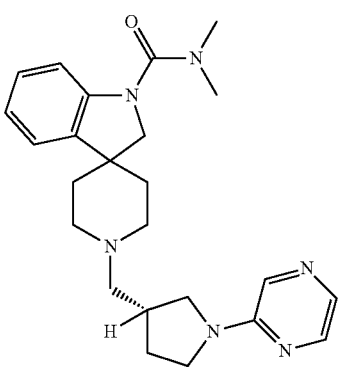
111
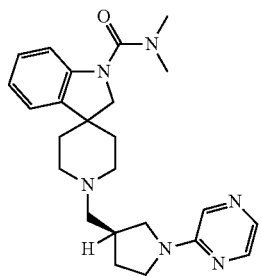
112
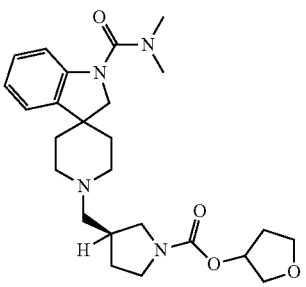
113
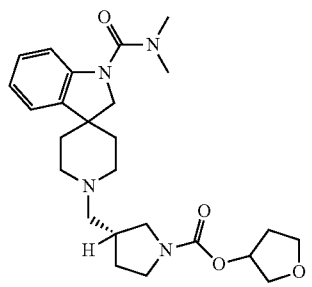
114

137 138
-continued
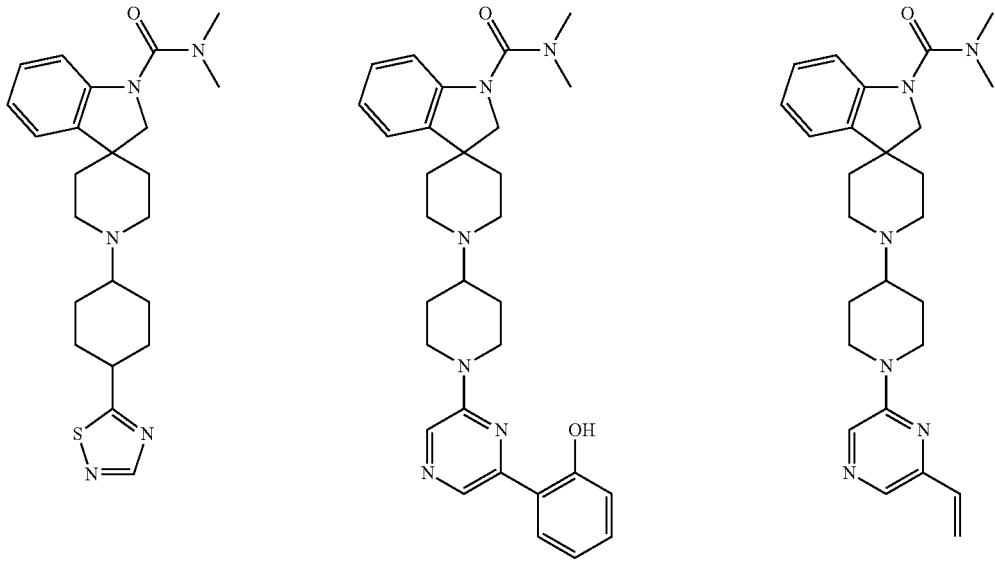
115 116 117
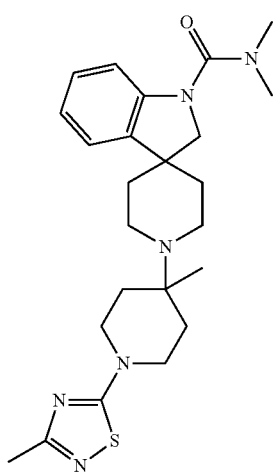 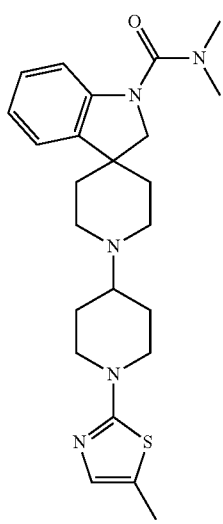 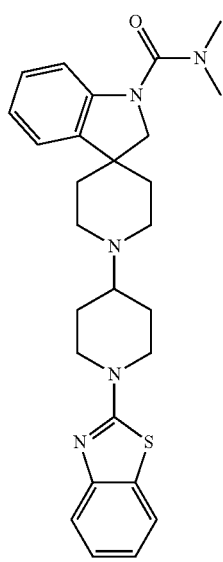
118 119

-continued

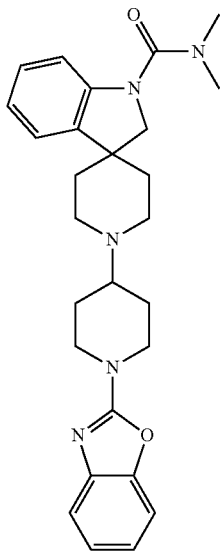
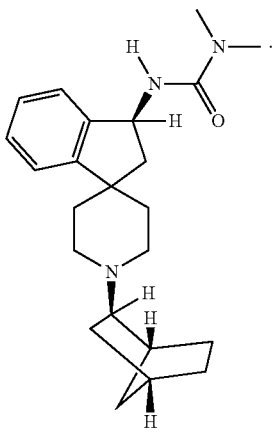

17. A compound of formula I

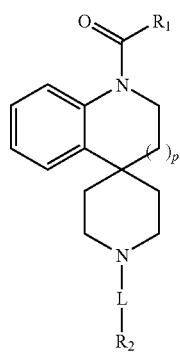

I or a pharmaceutically acceptable salt thereof, wherein
$R_1$ is —$NR_6R'_6$;
  Each of $R_6$ and $R'_6$ is independently hydrogen or an optionally substituted $C_{1-4}$ aliphatic, or
  $R_6$ and $R'_6$ together with the nitrogen atom to which they are attached form an optionally substituted 4-7 membered heterocycloaliphatic;
L is a bond or an unsubstituted methylene group;
$R_2$ is an optionally substituted bicyclic cycloaliphatic; or
$R_2$ is a monocyclic cycloaliphatic optionally substituted with a heteroaryl; or
$R_2$ is pyrrolidine-yl, 1,3-dioxolane-yl, imidazolidine-yl, 2-pyrazoline-yl, pyrazolidine-yl, piperidine-yl, 1,4-dioxane-yl, morpholine-yl, azepane-yl, azocane-yl, or piperazine-yl, each of which is optionally substituted with 1 to 3 of halo, or aliphatic, alkoxy, (aliphatic(oxy))carbonyl, (alkoxy(alkoxy))carbonyl, cycloaliphatic, heterocycloaliphatic, heteroaryl, amido, amino, (heterocycloaliphatic)oxy, or (heterocycloaliphatic(oxy))carbonyl, each of which is optionally substituted; or
$R_2$ is an optionally substituted bicyclic heterocycloaliphatic that has 1-3 heteroatoms independently selected from N, O, and S;
Each p is 0 or 1; and
When p is 0, then $R_1$ is an optionally substituted $C_{2-8}$ alkyl, an optionally substituted alkenyl, an optionally substituted alkynyl, N,N-dimethylamino, or $R_6$ and $R'_6$ together with the nitrogen atom to which they are attached form an optionally substituted 4-7 membered heterocycloaliphatic.

18. A pharmaceutical composition comprising a compound according to claim 17 and a pharmaceutical carrier.

* * * * *